United States Patent
Jung et al.

(10) Patent No.: US 9,499,524 B2
(45) Date of Patent: Nov. 22, 2016

(54) INSECTICIDAL COMPOUNDS

(75) Inventors: Pierre Joseph Marcel Jung, Stein (FR); Peter Danko, Bratislava (SK); Christopher Richard Ayles Godfrey, Stein (CH); Peter Renold, Stein (CH); Ottmar Franz Hueter, Stein (CH)

(73) Assignee: Syngenta Participations AG, Basel (CH)

( * ) Notice: Subject to any disclaimer, the term of this patent is extended or adjusted under 35 U.S.C. 154(b) by 328 days.

(21) Appl. No.: 13/634,750

(22) PCT Filed: Mar. 11, 2011

(86) PCT No.: PCT/EP2011/053681
§ 371 (c)(1),
(2), (4) Date: Sep. 13, 2012

(87) PCT Pub. No.: WO2011/113756
PCT Pub. Date: Sep. 22, 2011

(65) Prior Publication Data
US 2013/0012547 A1    Jan. 10, 2013

(30) Foreign Application Priority Data

Mar. 18, 2010 (EP) .................................... 10156847
Nov. 29, 2010 (EP) .................................... 10192952

(51) Int. Cl.
| | | |
|---|---|---|
| *C07D 249/06* | (2006.01) | |
| *C07D 401/12* | (2006.01) | |
| *C07D 405/12* | (2006.01) | |
| *C07D 417/12* | (2006.01) | |
| *C07D 407/12* | (2006.01) | |
| *A01P 9/00* | (2006.01) | |
| *A01N 43/828* | (2006.01) | |
| *A01P 7/04* | (2006.01) | |
| *A01P 7/02* | (2006.01) | |
| *A01P 5/00* | (2006.01) | |
| *A01N 43/647* | (2006.01) | |

(52) U.S. Cl.
CPC ........... *C07D 407/12* (2013.01); *C07D 249/06* (2013.01); *C07D 417/12* (2013.01)

(58) Field of Classification Search
CPC  C07D 249/06; C07D 401/12; C07D 405/12; C07D 417/12; C07D 407/12; A01P 9/00; A01P 7/04; A01P 7/02; A01P 5/00; A01N 43/828; A01N 43/647
USPC ................ 514/340, 359, 361; 548/255, 127; 546/268.4
See application file for complete search history.

(56) References Cited

FOREIGN PATENT DOCUMENTS

| EP | 0400842 | 12/1990 |
|---|---|---|
| EP | 0412849 | 2/1991 |
| WO | 2008003770 | 1/2008 |
| WO | 2009003998 | 1/2009 |

OTHER PUBLICATIONS

International Search Report for International Application No. PCT/EP2011/053681 mailed May 18, 2011.
Livi, Oreste et al., "Ester, Amide and Ether Derivatives of 1-(p-Phenyl-substituted)-1,2,3-trazoles", Instituto di Chimica Farmaceutica e Tossicologica dell'Universita, 56100 Pisa, Italy (Feb. 24, 1983).

*Primary Examiner* — Sarah Pihonak
*Assistant Examiner* — Jason A Deck
(74) *Attorney, Agent, or Firm* — Brian D. McAlhaney

(57) ABSTRACT

The present invention relates to novel triazole derivatives of formula (I) having insecticidal activity, to processes and intermediates for preparing them, to insecticidal, acaricidal, nematicidal or molluscicidal compositions comprising them and to methods of using them to combat and control insect, acarine, nematode or mollusc pests.

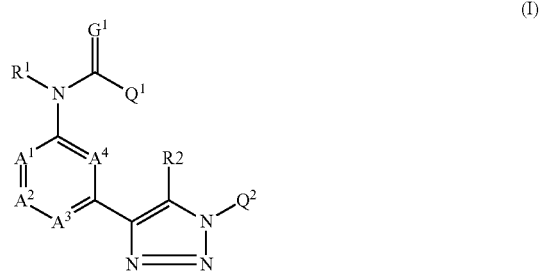

(I)

11 Claims, No Drawings

INSECTICIDAL COMPOUNDS

This application is a 371 of International Application No. PCT/EP2011/053681 filed Mar. 11, 2011, which claims priority to EP 10156847.5 filed Mar. 18, 2010, and EP 10192952.9 filed Nov. 29, 2010, the contents of which are incorporated herein by reference.

The present invention relates to novel triazole derivatives having insecticidal activity, to processes and intermediates for preparing them, to insecticidal, acaricidal, nematicidal or molluscicidal compositions comprising them and to methods of using them to combat and control insect, acarine, nematode or mollusc pests.

Compounds having insecticidal properties are disclosed in EP 1,714,958, JP 2006/306771, WO 2006/137376, EP 1,916,236, WO 2007/017075, WO 2008/000438 and WO 2009/049845. There exists a need for alternative methods of control of pests. Preferably, new compounds may possess improved insecticidal properties, such as improved efficacy, improved selectivity, lower tendency to generate resistance or activity against a broader range of pests. Compounds may be more advantageously formulated or provide more efficient delivery and retention at sites of action, or may be more readily biodegradable.

It has surprisingly been found that certain triazole derivatives have beneficial insecticidal properties.

Accordingly, the present invention provides a compound of formula (I)

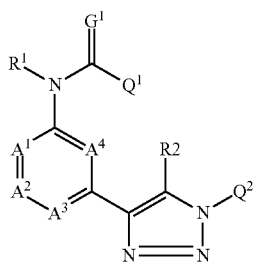

wherein
$A^1$, $A^2$, $A^3$ and $A^4$ are each independently C—X or nitrogen, wherein each X may be the same or different, and provided that no more than two of $A^1$, $A^2$, $A^3$ and $A^4$ are nitrogen;
$R^1$ is hydrogen, $C_1$-$C_4$alkyl, $C_1$-$C_4$alkyl-C(O)NH$_2$, or $C_1$-$C_4$alkylcarbonyl;
$R^2$ is hydrogen, halogen, $C_1$-$C_4$alkyl-$C_1$-$C_4$alkyl-C(O)NH$_2$, $C_1$-$C_6$ haloalkyl or cyano;
$G^1$ is oxygen or sulfur;
X is hydrogen, halogen, cyano, $C_1$-$C_4$alkyloxy, $C_1$-$C_4$alkyl or $C_1$-$C_4$haloalkyl;
$Q^1$ is aryl or heterocyclyl, each optionally substituted by one to five $R^3$ substituents, which may be the same or different;
$R^3$ is selected from cyano, amino, nitro, hydroxy, halogen, $C_1$-$C_4$alkyl, $C_1$-$C_4$haloalkyl, $C_2$-$C_4$alkenyl, $C_2$-$C_4$haloalkenyl, $C_2$-$C_4$alkynyl, $C_2$-$C_4$haloalkynyl, $C_3$-$C_6$cycloalkyl, $C_3$-$C_6$halocycloalkyl, $C_1$-$C_3$alkoxy, $C_1$-$C_3$haloalkoxy, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl, $C_1$-$C_3$haloalkylsulfonyl, $C_1$-$C_4$alkylamino, di-($C_1$-$C_4$alkyl)amino, $C_1$-$C_4$alkylcarbonyl, $C_1$-$C_4$alkylcarbonyloxy, $C_1$-$C_4$alkoxycarbonyl, $C_1$-$C_4$alkylcarbonylamino and phenyl;
$Q^2$ is a moiety of formula (A) or (B)

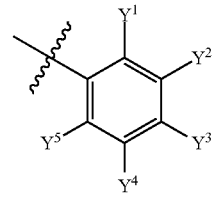

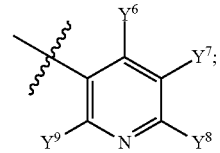

$Y^1$ and $Y^5$ are each independently selected from hydrogen, cyano, halogen, $C_1$-$C_4$alkyl, $C_1$-$C_4$haloalkyl, $C_1$-$C_4$alkoxy-$C_1$-$C_4$alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl and $C_1$-$C_3$haloalkylsulfonyl;
$Y^3$ is $C_1$-$C_6$perfluoroalkyl, $C_1$-$C_6$perfluoroalkylthio, $C_1$-$C_6$perfluoroalkylsulfinyl or $C_1$-$C_6$perfluoroalkylsulfonyl;
$Y^2$ and $Y^4$ are each independently selected from hydrogen, halogen and $C_1$-$C_4$alkyl;
$Y^6$ and $Y^9$ are each independently selected from cyano, halogen, $C_1$-$C_4$alkyl, $C_1$-$C_4$haloalkyl, $C_1$-$C_4$alkoxy-$C_1$-$C_4$alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl and $C_1$-$C_3$haloalkylsulfonyl;
$Y^8$ is $C_1$-$C_4$haloalkoxy, $C_2$-$C_6$perfluoroalkyl, $C_1$-$C_6$perfluoroalkylthio, $C_1$-$C_6$perfluoroalkylsulfinyl or $C_1$-$C_6$perfluoroalkylsulfonyl;
$Y^7$ is hydrogen, halogen or $C_1$-$C_4$alkyl;
or an agrochemically acceptable salt or N-oxides thereof.

The compounds of formula (I) may exist in different geometric or optical isomers (enantiomers and/or diastereoisomers) or tautomeric forms. This invention covers all such isomers and tautomers and mixtures thereof in all proportions as well as isotopic forms such as deuterated compounds.

Unless otherwise indicated, alkyl, on its own or as part of another group, such as alkoxy, alkylcarbonyl or alkoxycarbonyl, may be straight or branched chain and may preferably contain from 1 to 6 carbon atoms, more preferably 1 to 4, and most preferably 1 to 3. Examples of alkyl include methyl, ethyl, n-propyl, iso-propyl, n-butyl, sec-butyl, iso-butyl and tert-butyl.

Unless otherwise indicated, alkenyl and alkynyl, on their own or as part of another substituent, may be straight or branched chain and may preferably contain 2 to 6 carbon atoms, preferably 2 to 4, more preferably 2 to 3, and where appropriate, may be in either the (E)- or (Z)-configuration. Examples include vinyl, allyl and propargyl.

Halogen means fluorine, chlorine, bromine or iodine.

Haloalkyl groups may contain one or more identical or different halogen atoms, and includes, for example, trifluoromethyl, chlorodifluoromethyl, 2,2,2-trifluoroethyl or 2,2-difluoroethyl. Perfluoroalkyl groups are alkyl groups which are completely substituted with fluorine atoms and include, for example, trifluoromethyl, pentafluoroethyl and heptafluoroprop-2-yl.

Haloalkenyl and haloalkynyl groups may contain one or more identical or different halogen atoms, and include, for example, 2,2-difluorovinyl, 1,2-dichloro-2-fluorovinyl or 1-chloroprop-2-yn-1-yl.

Unless otherwise indicated, cycloalkyl may be mono- or bi-cyclic, may be optionally substituted by one or more $C_1$-$C_6$alkyl groups, and preferably contain 3 to 8 carbon atoms, more preferably 3 to 6 carbon atoms. Examples of cycloalkyl include cyclopropyl, 1-methylcyclopropyl, 2-methylcyclopropyl, cyclobutyl, cyclopentyl and cyclohexyl.

Halocycloalkyl groups may contain one or more identical or different halogen atoms, and includes, for example, 2,2-dichlorocyclopropyl, 2,2-dichloro-1-methylcyclopropyl and 2-chloro-4-fluorocyclohexyl.

Aryl includes phenyl, naphthyl, anthracenyl, indenyl, phenanthrenyl and biphenyl, with phenyl being preferred.

Heteroaryl means a mono-, bi- or tricyclic, aromatic hydrocarbon, containing 3 to 14, preferably 5 to 10, more preferably 6 to 8, ring-atoms, including 1 to 6, preferably 1 to 4, heteroatoms independently selected from nitrogen, oxygen and sulfur. Examples include furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, benzothiadiazolyl, indazolyl, benzotriazolyl, benzothiazolyl, benzoxazolyl, quinolyl, isoquinolyl, phthalazinyl, quinoxalinyl, quinazolinyl, cinnolinyl and naphthyridinyl.

Heterocyclyl, as used herein, includes heteroaryl, and in addition may be a saturated or partially unsaturated cyclic hydrocarbon containing from 3 to 10 ring-atoms up to 4 of which are heteroatoms selected from nitrogen, oxygen and sulfur, and may be optionally substituted by one or more groups independently selected from halogen, nitro, cyano, alkyl, alkoxy. Examples of non-aromatic heterocyclyl groups are oxiranyl, azetidinyl, tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl.

Preferred values of $A^1$, $A^2$, $A^3$, $A^4$, $R^1$, $R^2$, $R^3$, $G^1$, X, $Q^1$, $Y^1$, $Y^2$, $Y^3$, $Y^4$, $Y^5$, $Y^6$, $Y^7$, $Y^8$ and $Y^9$ are, in any combination, as set out below.

Preferably $A^1$ is C—X.
Preferably $A^2$ is C—X.
Preferably $A^3$ is C—X.
Preferably $A^4$ is C—X.

Preferably, X is hydrogen, halogen, cyano, methyl, trifluoromethyl or methoxy. More preferably, X is hydrogen, fluoro, chloro, cyano, trifluoromethyl or methoxy. Even more preferably, X is hydrogen, fluoro, cyano or methoxy. Most preferably, X is hydrogen, fluoro or cyano.

More preferably, $A^1$, $A^2$, $A^3$ and $A^4$ are C—X and each X is independently selected from hydrogen, halogen, cyano, methyl, trifluoromethyl and methoxy. Even more preferably, $A^1$, $A^2$, $A^3$ and $A^4$ are C—X and each X is independently selected from hydrogen, fluoro, cyano and methoxy. Most preferably, $A^1$ is CH, C—CN or C—F; and $A^2$, $A^3$ and $A^4$ are CH.

Preferably, $G^1$ is oxygen.

Preferably, $R^1$ is hydrogen, methyl, ethyl or acetyl. More preferably, $R^1$ is hydrogen, methyl or ethyl. Most preferably, $R^1$ is hydrogen.

Preferably, $R^2$ is hydrogen, methyl, trifluoromethyl or halogen. More preferably, $R^2$ is hydrogen, trifluoromethyl or halogen. Even more preferably, $R^2$ is hydrogen or halogen. Most preferably, $R^2$ is hydrogen.

Preferably, $Q^1$ is aryl or heteroaryl; each optionally substituted by one to five substituents independently selected from cyano, nitro, hydroxy, bromo, chloro, fluoro, methyl, trifluoromethyl, methoxy, trifluoromethoxy, methylthio, methylsulfinyl, methylsulfonyl and phenyl.

More preferably, $Q^1$ is phenyl, pyridyl, furanyl, thiophenyl, pyrazolyl or 1,2,3-thiadiazolyl; each optionally substituted by one to four substituents independently selected from cyano, nitro, hydroxy, bromo, chloro, fluoro, methyl, trifluoromethyl, methoxy, trifluoromethoxy, methylthio, methylsulfinyl, methylsulfonyl and phenyl.

Even more preferably, $Q^1$ is phenyl, pyridyl or furanyl; each optionally substituted by one to four substituents independently selected from cyano, nitro, hydroxy, bromo, chloro, fluoro, methyl, ethyl, trifluoromethyl, methoxy, trifluoromethoxy, methylthio, methylsulfinyl, methylsulfonyl and phenyl.

Most preferably, $Q^1$ is phenyl or pyridyl; each optionally substituted by one, two or three substituents independently selected from cyano, nitro, chloro, fluoro, methyl, ethyl, trifluoromethyl, methoxy and trifluoromethoxy.

Preferred examples of $Q^1$ include phenyl, 5-bromofuran-2-yl, 2-methoxyphenyl, 2-bromophenyl, 2-methylphenyl, 5-bromopyrid-3-yl, 3-methylpyrid-2-yl, 2-chloro-4-fluorophenyl, 4-methyl-1,2,3-thiadiazol-5-yl, 3-chloro-2-fluorophenyl, 4-nitrophenyl, 5-chloro-2-fluorophenyl, 3-chloro-2-methylphenyl, 1,2,3-thiadiazol-4-yl, 2-chloro-4-nitrophenyl, thiophen-2-yl, 2-chloro-5-nitrophenyl, 2-(trifluoromethoxy)phenyl, 2-chlorophenyl, 4-(trifluoromethoxy)phenyl, 3-chlorophenyl, 2-(trifluoromethyl)phenyl, 2-chloropyrid-3-yl, 4-(trifluoromethyl)phenyl, 2-chloropyrid-4-yl, 2-methyl-4-cyanophenyl, 6-chloropyrid-3-yl, 2,4,6-trifluorophenyl, 5-chlorothiophen-2-yl, 2,6-difluorophenyl, 3-chloro-5-(trifluoromethyl)pyrid-2-yl, 2,6-difluoro-4-cyanophenyl, 4-cyano-2-fluorophenyl, 2-chloro-6-fluorophenyl, 4-cyanophenyl, 2-methyl-3-nitrophenyl, 2-methyl-4-nitrophenyl, 2,5-dichlorophenyl, 3-methyl-4-nitrophenyl, 2,3-difluorophenyl, 2-chloro-4-cyanophenyl, 1,3-dimethyl-1H-pyrazol-5-yl, 2-fluoro-4-cyanophenyl, 2-fluorophenyl, 4-methylthiophenyl, 4-fluorophenyl, 1-methyl-3-(trifluoromethyl)pyrazol-4-yl, 2-fluoropyrid-3-yl, 4-pyridyl, 2-fluoro-3-(trifluoromethyl)phenyl, 1,3-dimethylpyrazol-4-yl, 2-fluoro-5-(trifluoromethyl)-phenyl, 4-methylphenyl, 4-fluoro-3-(trifluoromethyl)phenyl, 4-fluoro-2-methylphenyl, furan-2-yl, and 2,4-difluorophenyl.

Preferably, $Y^1$ is hydrogen, cyano, fluoro, chloro, bromo, methyl, ethyl, trifluoromethyl or methoxymethyl. More preferably, $Y^1$ is chloro, bromo, methyl, ethyl, or trifluoromethyl. Most preferably, $Y^1$ is chloro.

Preferably, $Y^2$ is hydrogen, fluoro, chloro or methyl. Most preferably, $Y^2$ is hydrogen.

Preferably, $Y^3$ is heptafluoropropyl, nonafluorobutyl, heptafluoropropylthio, heptafluoropropylsulfinyl, or heptafluoropropylsulfonyl. More preferably, $Y^3$ is heptafluoroprop-1-yl, heptafluoroprop-2-yl, nonafluorobut-2-yl, heptafluoroprop-1-ylthio, heptafluoroprop-1-ylsulfinyl, heptafluoroprop-1-ylsulfonyl, heptafluoroprop-2-ylthio, heptafluoroprop-2-ylsulfinyl, or heptafluoroprop-2-ylsulfonyl. Even more preferably, $Y^3$ is heptafluoroprop-1-yl, heptafluoroprop-2-yl, nonafluorobut-2-yl, heptafluoroprop-2-ylthio, heptafluoroprop-2-ylsulfinyl, or heptafluoroprop-2-ylsulfonyl. Most preferably, $Y^3$ is heptafluoroprop-2-yl or nonafluorobut-2-yl.

Preferably, $Y^4$ is hydrogen, fluoro, chloro or methyl. Most preferably, $Y^4$ is hydrogen.

Preferably, $Y^5$ is hydrogen, cyano, fluoro, chloro, bromo, methyl, ethyl, trifluoromethyl or methoxymethyl. More preferably, $Y^5$ is chloro, bromo, methyl, ethyl or trifluoromethyl. Most preferably, $Y^5$ is chloro.

Preferably, $Y^6$ is hydrogen, cyano, fluoro, chloro, bromo, methyl, ethyl, trifluoromethyl or methoxymethyl.

Preferably, $Y^7$ is hydrogen, fluoro, chloro or methyl.

Preferably, $Y^8$ is heptafluoropropyl, nonafluorobutyl, heptafluoropropylthio, heptafluoropropylsulfinyl, or heptafluoropropylsulfonyl. Most preferably, $Y^8$ is heptafluoroprop-1-yl, heptafluoroprop-2-yl, nonafluorobut-2-yl, heptafluoroprop-2-ylthio, heptafluoroprop-2-ylsulfinyl, or heptafluoroprop-2-ylsulfonyl.

Preferably $Y^9$ is bromo, chloro, methyl, ethyl or trifluoromethyl.

Preferably, $Q^2$ is a moiety of formula (A).

More preferably, $Q^2$ is 4-heptafluoroisopropyl-2,6-dimethylphenyl, 4-heptafluoroisopropyl-2-methyl-6-ethylphenyl, 4-heptafluoroisopropyl-2,6-diethylphenyl, 4-heptafluoroisopropyl-2-methoxymethyl-6-methylphenyl, 4-heptafluoroisopropyl-2,6-dichlorophenyl, 4-heptafluoroisopropyl-2,6-dibromophenyl, 4-heptafluoroisopropyl-2-chloro-6-bromophenyl, 4-heptafluoroisopropyl-2-ethyl-6-bromophenyl, 4-heptafluoroisopropyl-2-methyl-6-bromophenyl, 4-heptafluoroisopropyl-2-bromo-6-ethylphenyl, 4-(1,2,2,3,3,3-hexafluoro-1-(trifluoromethyl)propyl)-2,6-dimethylphenyl, 4-(1,2,2,3,3,3-hexafluoro-1-(trifluoromethyl)propyl)-2-methyl-6-ethylphenyl, 4-(1,2,2,3,3,3-hexafluoro-1-(trifluoromethyl)propyl)-2,6-diethylphenyl, 4-(1,2,2,3,3,3-hexafluoro-1-(trifluoromethyl)propyl)-2-methoxymethyl-6-methylphenyl, 4-(1,2,2,3,3,3-hexafluoro-1-(trifluoromethyl)propyl)-2,6-dichlorophenyl, 4-(1,2,2,3,3,3-hexafluoro-1-(trifluoromethyl)propyl)-2,6-dibromophenyl, 4-(1,2,2,3,3,3-hexafluoro-1-(trifluoromethyl)propyl)-2-chloro-6-bromophenyl, 4-(1,2,2,3,3,3-hexafluoro-1-(trifluoromethyl)propyl)-2-ethyl-6-bromophenyl, 4-(1,2,2,3,3,3-hexafluoro-1-(trifluoromethyl)propyl)-2-bromo-6-methylphenyl, or 4-(1,2,2,3,3,3-hexafluoro-1-(trifluoromethyl)propyl)-2-bromo-6-ethylphenyl.

Most preferably, $Q^2$ is 4-heptafluoroisopropyl-2,6-dichlorophenyl, 4-heptafluoroisopropyl-2-methyl-6-bromophenyl, 4-(1,2,2,3,3,3-hexafluoro-1-(trifluoromethyl)propyl)-2-methyl-6-ethylphenyl, or 4-(1,2,2,3,3,3-hexafluoro-1-(trifluoromethyl)propyl)-2,6-dichlorophenyl.

In a preferred aspect of the invention, $A^1$, $A^2$, $A^3$ and $A^4$ are CH. In a further preferred aspect of the invention, $A^4$ is C—F and $A^1$, $A^2$, and $A^3$ are CH. In a further preferred aspect of the invention, $A^1$ is C—CN and $A^2$, $A^3$, and $A^4$ are CH. In a further preferred aspect of the invention, $A^4$ is C—OCH$_3$ and $A^1$, $A^2$, and $A^3$ are CH. In a further preferred aspect of the invention, $A^1$ is C—F and $A^2$, $A^3$, and $A^4$ are CH.

In a first preferred embodiment of the invention, $A^1$, $A^2$, $A^3$ and $A^4$ are CH; $R^1$ and $R^2$ are hydrogen; $G^1$ is oxygen; $Q^1$ is 2-fluorophenyl; $Q^2$ is a moiety of formula (A); and $Y^1$, $Y^3$ and $Y^5$ are represented by substituent combinations 1.01 to 1.16 of Table 1.

TABLE 1

| | $Y^1$ | $Y^5$ | $Y^3$ |
|---|---|---|---|
| 1.01 | Me | Br | nonafluorobut-2-yl |
| 1.02 | Me | Cl | nonafluorobut-2-yl |
| 1.03 | Et | Br | nonafluorobut-2-yl |
| 1.04 | Et | Cl | nonafluorobut-2-yl |
| 1.05 | Me | Et | nonafluorobut-2-yl |
| 1.06 | Br | Br | nonafluorobut-2-yl |
| 1.07 | Cl | Cl | nonafluorobut-2-yl |
| 1.08 | Cl | Br | nonafluorobut-2-yl |
| 1.09 | Me | Br | heptafluoroprop-2-yl |
| 1.10 | Me | Cl | heptafluoroprop-2-yl |
| 1.11 | Et | Br | heptafluoroprop-2-yl |
| 1.12 | Et | Cl | heptafluoroprop-2-yl |
| 1.13 | Et | Me | heptafluoroprop-2-yl |
| 1.14 | Br | Br | heptafluoroprop-2-yl |
| 1.15 | Cl | Cl | heptafluoroprop-2-yl |
| 1.16 | Cl | Br | heptafluoroprop-2-yl |

In a second preferred embodiment of the invention, $A^1$, $A^2$, $A^3$ and $A^4$ are CH; $R^1$ and $R^2$ are hydrogen; $G^1$ is oxygen; $Q^1$ is 2-chloropyrid-3-yl; $Q^2$ is a moiety of formula (A); and $Y^1$, $Y^3$ and $Y^5$ are represented by substituent combinations 1.01 to 1.16 of Table 1.

In a third preferred embodiment of the invention, $A^1$, $A^2$, $A^3$ and $A^4$ are CH; $R^1$ and $R^2$ are hydrogen; $G^1$ is oxygen; $Q^1$ is 2-chloro-4-fluorophenyl; $Q^2$ is a moiety of formula (A); and $Y^1$, $Y^3$ and $Y^5$ are represented by substituent combinations 1.01 to 1.16 of Table 1.

In a fourth preferred embodiment of the invention, $A^1$, $A^2$, $A^3$ and $A^4$ are CH; $R^1$ and $R^2$ are hydrogen; $G^1$ is oxygen; $Q^1$ is 4-cyanophenyl; $Q^2$ is a moiety of formula (A); and $Y^1$, $Y^3$ and $Y^5$ are represented by substituent combinations 1.01 to 1.16 of Table 1.

In a fifth preferred embodiment of the invention, $A^1$, $A^2$, $A^3$ and $A^4$ are CH; $R^1$ and $R^2$ are hydrogen; $G^1$ is oxygen; $Q^1$ is 4-fluorophenyl; $Q^2$ is a moiety of formula (A); and $Y^1$, $Y^3$ and $Y^5$ are represented by substituent combinations 1.01 to 1.16 of Table 1.

In a sixth preferred embodiment of the invention, $A^1$, $A^2$, $A^3$ and $A^4$ are CH; $R^1$ and $R^2$ are hydrogen; $G^1$ is oxygen; $Q^1$ is 2-methylphenyl; $Q^2$ is a moiety of formula (A); and $Y^1$, $Y^3$ and $Y^5$ are represented by substituent combinations 1.01 to 1.16 of Table 1.

In a seventh preferred embodiment of the invention, $A^1$, $A^2$, $A^3$ and $A^4$ are CH; $R^1$ and $R^2$ are hydrogen; $G^1$ is oxygen; $Q^1$ is 4-fluoro-2-methylphenyl; $Q^2$ is a moiety of formula (A); and $Y^1$, $Y^3$ and $Y^5$ are represented by substituent combinations 1.01 to 1.16 of Table 1.

In an eighth preferred embodiment of the invention, $A^1$, $A^2$, $A^3$ and $A^4$ are CH; $R^1$ and $R^2$ are hydrogen; $G^1$ is oxygen; $Q^1$ is 2-methyl-3-nitrophenyl; $Q^2$ is a moiety of formula (A); and $Y^1$, $Y^3$ and $Y^5$ are represented by substituent combinations 1.01 to 1.16 of Table 1.

In a ninth preferred embodiment of the invention, $A^1$ is C—CN; $A^2$, $A^3$, and $A^4$ are CH; $R^1$ and $R^2$ are hydrogen; $G^1$ is oxygen; $Q^1$ is 2-methyl-4-cyanophenyl; $Q^2$ is a moiety of formula (A); and $Y^1$, $Y^3$ and $Y^5$ are represented by substituent combinations 1.01 to 1.16 of Table 1.

In a tenth preferred embodiment of the invention, $A^1$ is C—F; $A^2$, $A^3$, and $A^4$ are CH; $R^1$ and $R^2$ are hydrogen; $G^1$ is oxygen; $Q^1$ is 2,4,6-trifluorophenyl; $Q^2$ is a moiety of formula (A); and $Y^1$, $Y^3$ and $Y^5$ are represented by substituent combinations 1.01 to 1.16 of Table 1.

The intermediate compounds of formula (Id) form a further aspect of the invention

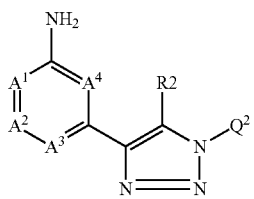

(Id)

wherein $A^1$, $A^2$, $A^3$, $A^4$, $R^2$ and $Q^2$ are as defined in relation to formula (I); or a salt thereof. The preferences for $A^1$, $A^2$, $A^3$, $A^4$, $R^2$ and $Q^2$ are the same as the preferences set out for the corresponding substituents of the compounds of formula (I).

In a preferred embodiment, the invention provides a compound of formula (Id) wherein $A^1$, $A^2$, $A^3$ and $A^4$ are CH; $R^2$ is hydrogen; $Q^2$ is a moiety of formula (A); and $Y^1$, $Y^3$ and $Y^5$ are represented by substituent combinations 1.01 to 1.16 of Table 1.

In a further preferred embodiment, the invention provides a compound of formula (Id) wherein $A^1$ is C—CN; $A^2$, $A^3$, and $A^4$ are CH; $R^2$ is hydrogen; $Q^2$ is a moiety of formula (A); and $Y^1$, $Y^3$ and $Y^5$ are represented by substituent combinations 1.01 to 1.16 of Table 1.

In a further preferred embodiment, the invention provides a compound of formula (Id) wherein $A^1$ is C—F; $A^2$, $A^3$, and $A^4$ are CH; $R^2$ is hydrogen; $Q^2$ is a moiety of formula (A); and $Y^1$, $Y^3$ and $Y^5$ are represented by substituent combinations 1.01 to 1.16 of Table 1.

The compounds of the invention may be made by the following methods.

(1) Compounds of formula (I), wherein $G^1$ is oxygen, may be prepared by reaction of a compound of formula (III), wherein $R^4$ is alkynyl substituted by $R^2$, with and azido derivative, $Q^2$-$N_3$, in the presence of copper or a copper catalyst, such as copper sulfate or copper (I) iodide, and optionally in the presence of a base, such as N-ethyldiisopropylamine, in the presence of a solvent or a mixture of solvents, such as t-butanol, water. In the case of a Cu(II) catalyst, a reducing agent, such as sodium ascorbate may be used. In the case of a Cu(0) catalyst, such as an amine salt, an oxidising agent may be used. (See, for example: Angewandte Chemie, International Edition (2009), 48(27), 4900-4908 and cited references, Angew. Chem. Int. Ed. 2008, 47, 2182-2184 and cited references, and Eur. J. Org. Chem. 2006, 51-68 and cited references).

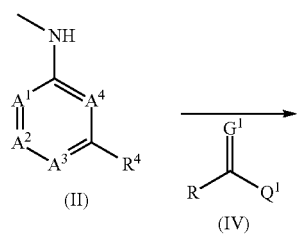

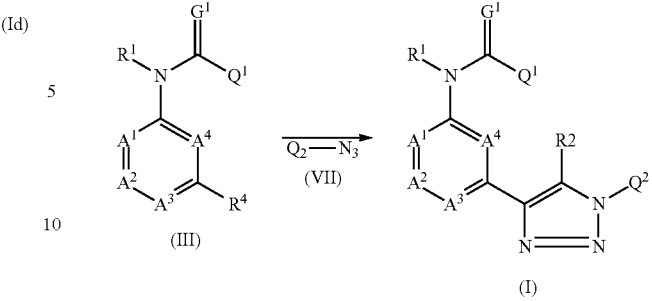

(2) Compounds of formula (III), wherein $G^1$ is oxygen, and $R^4$ is alkynyl substituted by $R^2$, may be prepared by acylation of a compound of formula (II) with a compound of formula (IV), wherein R is OH, in the presence of a coupling reagent, such as DCC(N,N'-dicyclohexylcarbodiimide), EDC (1-ethyl-3-[3-dimethylamino-propyl]carbodiimide hydrochloride) or BOP-Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. Optionally, when R is Cl, the acylation reaction may be carried out under basic conditions (for example in the presence of pyridine, triethylamine, 4-(dimethylamino)pyridine or diisopropylethylamine), optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. Optionally, when R is $C_1$-$C_6$alkoxy, the amide may be prepared by heating the ester (IV) and amine (II) together.

(3) Compounds of formula (II), wherein $R^1$ is $C_1$-$C_6$alkyl, may be prepared from a compound of formula (II) wherein $R^1$ is H via reductive amination by reaction of the amine with an aldehyde or ketone and a reducing agent such as sodium cyanoborohydride. Alternatively alkylation may be achieved by treating the amine with an alkylating agent such as an alkyl halide, optionally in the presence of a base.

(4) Compounds of formula (I), wherein $G^1$ is oxygen, may be also be prepared by reaction of a compound of formula (Id) with a compound of formula (IV) as described in (2).

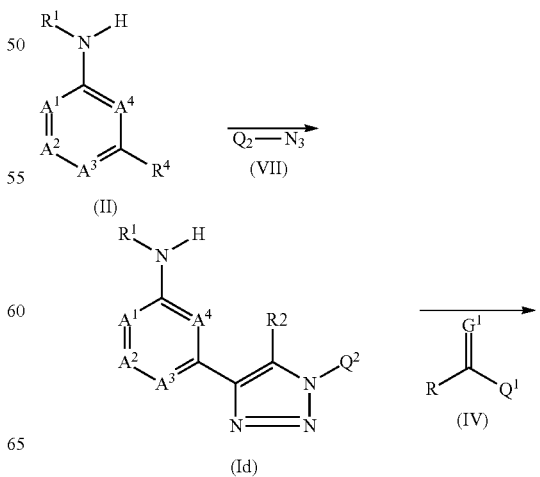

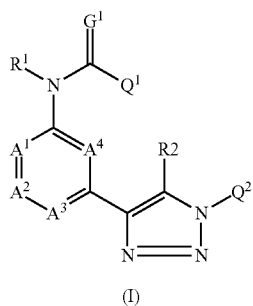

(I)

(5) Compounds of formula (Id) may be prepared from a compound of formula (II), wherein $R^4$ is alkynyl substituted by $R^2$, using the same conditions as described in (1).

(6) Compounds of formula (II), wherein $R^1$ is H and $R^4$ is alkynyl substituted by $R^2$, may be prepared by the reduction of a nitro compound of formula (V) by, for example, treatment with tin chloride under acidic conditions, or hydrogenation catalysed by a metal such as iron.

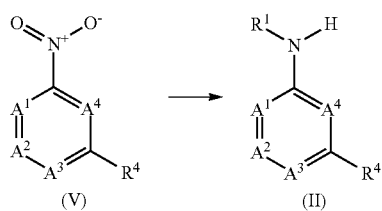

(7) Alternatively, compounds of formula (II), wherein $R^1$ is H and $R^4$ is 1,2,3-triazole substituted by $R^2$, may be prepared by the reduction of a nitro compound of formula (V), wherein $R^4$ is 1,2,3-triazole substituted by $R^2$, by the method described in (6).

(8) Compounds of formula (V), wherein $R^4$ is 1,2,3-triazole substituted by $R^2$, may be prepared from a compound of formula (V), wherein $R^4$ is alkynyl substituted by $R^2$ by reaction with an azido derivative, $Q^2$-$N_3$, using the same conditions as described in (1).

(9) Compounds of formula (I), wherein $G^1$ is sulfur, may be prepared from a compound of formula (I), wherein $G^1$ is oxygen, by treatment with a thio-transfer reagent, such as Lawesson's reagent or phosphorus pentasulfide.

(10) Compounds of formula (Id), may be prepared from a compound of formula (II), wherein $R^4$ is alkynyl substituted by $R^2$ and P is a suitable protecting group, using the same conditions as described in (1), followed by removal of the protecting group P under standard conditions.

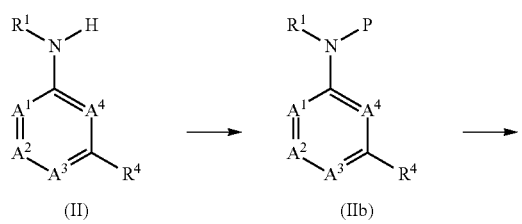

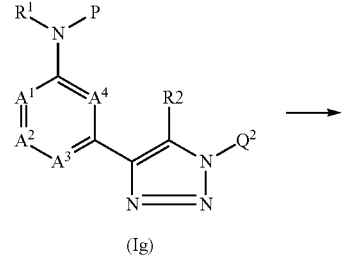

(Ig)

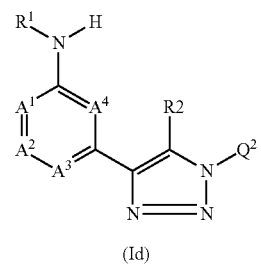

(Id)

(11) Compounds of formula (V), wherein $R^4$ is alkynyl substituted by $R^2$ or 1,2,3-triazole substituted by $R^2$, may be prepared from a compound of formula (VI), wherein $A^1$, $A^2$, $A^3$ and $A^4$ are each independently C-LG or C—H, and LG is a leaving group, such as fluorine or chlorine, by reaction with a nucleophile, such as an aliphatic alcohol, sodium cyanide.

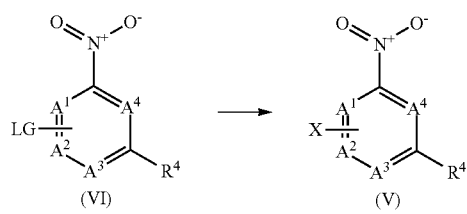

(12) Compounds of formula (VII), wherein $Q_2$ is as described for the compound of formula (I), may be also be prepared by reaction of a compound of formula (VIII) with sodium nitrite followed by addition of sodium azide. See, for example: Diazo Chemistry I: Aromatic and Heteroaromatic Compounds. Zollinger, H. Germany. (1994), 380 pp. Publisher: (VCH, Weinheim, Germany) and cited references.

The compounds of formula (I) may be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the compounds of the invention include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the *Mastotermitidae* (for example *Mastotermes* spp.), the *Kalotermitidae* (for example *Neotermes* spp.), the *Rhinotermitidae* (for example *Coptotermes formosanus, Reticulitermes flavipes, R. speratu, R. virginicus, R. hesperus*, and *R. santonensis*) and the *Termitidae* (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest, The compounds of formula (I) are preferably used against insects, acarines or nematodes.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavour).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal, acaricidal, nematicidal or molluscicidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octyl-cresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures preferably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula I may be the sole active ingredient of the composition or it may be admixed with one or more additional active ingredients such as a pesticide (insect, acarine, mollusc and nematode pesticide), fungicide, synergist, herbicide, safener or plant growth regulator where appropriate. The activity of the compositions according to the invention may thereby be broadened considerably and may have surprising advantages which can also be described, in a wider sense, as synergistic activity. An additional active ingredient may: provide a composition having a broader spectrum of activity or increased persistence at a locus; provide a composition demonstrating better plant/crop tolerance by reducing phytotoxicity; provide a composition controlling insects in their different development stages; synergise the activity or complement the activity (for example by increasing the speed of effect or overcoming repellency) of the compound of formula I; or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, or spinosad, spinetoram or azadirachtin;

h) Hormones or pheromones;

i) Organochlorine compounds such as endosulfan, benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds such as imidacloprid, thiacloprid, acetamiprid, clothianidin, nitenpyram, dinotefuran or thiamethoxam;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine or pyrifluquinazon;

r) Spirotetramat, spirodiclofen or spiromesifen;

s) Flubendiamide, chloranthraliniprole, or cyanthraniliprole;

t) Cyenopyrafen or cyflumetofen; or u) Sulfoxaflor.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

The following mixtures of the compounds of formula I with active ingredients are preferred, wherein, preferably, the term "COMPOUND OF FORMULA I" refers to a compound selected from the Tables A, B or C:

an adjuvant selected from the group of substances consisting of an oil of vegetable or animal origin, a mineral oil, alkyl esters of such oils or mixtures of such oils, and petroleum oils (alternative name) (628)+COMPOUND OF FORMULA I, an acaricide selected from the group of substances consisting of 1,1-bis(4-chlorophenyl)-2-ethoxyethanol (IUPAC name) (910)+COMPOUND OF FORMULA I,2,4-dichlorophenyl benzenesulfonate (IUPAC/Chemical Abstracts name) (1059)+COMPOUND OF FORMULA I,2-fluoro-N-methyl-N-1-naphthylacetamide (IUPAC name) (1295)+COMPOUND OF FORMULA I,4-chlorophenyl phenyl sulfone (IUPAC name) (981)+COMPOUND OF FORMULA I, abamectin (1)+COMPOUND OF FORMULA I, acequinocyl (3)+COMPOUND OF FORMULA I, acetoprole [CCN]+COMPOUND OF FORMULA I, acrinathrin (9)+COMPOUND OF FORMULA I, aldicarb (16)+COMPOUND OF FORMULA I, aldoxycarb (863)+COMPOUND OF FORMULA I, alpha-cypermethrin (202)+COMPOUND OF FORMULA I, amidithion (870)+COMPOUND OF FORMULA I, amidoflumet [CCN]+COMPOUND OF FORMULA I, amidothioate (872)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, aramite (881)+COMPOUND OF FORMULA I, arsenous oxide (882)+COMPOUND OF FORMULA I, AVI 382 (compound code)+COMPOUND OF FORMULA I, AZ 60541 (compound code)+COMPOUND OF FORMULA I, azinphos-ethyl (44)+COMPOUND OF FORMULA I, azinphos-methyl (45)+COMPOUND OF FORMULA I, azobenzene (IUPAC name) (888)+COMPOUND OF FORMULA I, azocyclotin (46)+COMPOUND OF FORMULA I, azothoate (889)+COMPOUND OF FORMULA I, benomyl (62)+COMPOUND OF FORMULA I, benoxafos (alternative name) [CCN]+COMPOUND OF FORMULA I, benzoximate (71)+COMPOUND OF FORMULA I, benzyl benzoate (IUPAC name) [CCN]+COMPOUND OF FORMULA I, bifenazate (74)+COMPOUND OF FORMULA I, bifenthrin (76)+COMPOUND OF FORMULA I, binapacryl (907)+COMPOUND OF FORMULA I, brofenvalerate (alternative name)+COMPOUND OF FORMULA I, bromocyclen (918)+COMPOUND OF FORMULA I, bromophos (920)+COMPOUND OF FORMULA I, bromophos-ethyl (921)+COMPOUND OF FORMULA I, bromopropylate (94)+COMPOUND OF FORMULA I, buprofezin (99)+COMPOUND OF FORMULA I, butocarboxim (103)+COMPOUND OF FORMULA I, butoxycarboxim (104)+COMPOUND OF FORMULA I, butylpyridaben (alternative name)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbophenothion (947)+COMPOUND OF FORMULA I, CGA 50'439 (development code) (125)+COMPOUND OF FORMULA I, chinomethionat (126)+COMPOUND OF FORMULA I, chlorbenside (959)+COMPOUND OF FORMULA I, chlordimeform (964)+COMPOUND OF FORMULA I, chlordimeform hydrochloride (964)+COMPOUND OF FORMULA I, chlorfenapyr (130)+COMPOUND OF FORMULA I, chlorfenethol (968)+COMPOUND OF FORMULA I, chlorfenson (970)+COMPOUND OF FORMULA I, chlorfensulphide (971)+COMPOUND OF FORMULA I, chlorfenvinphos (131)+COMPOUND OF FORMULA I, chlorobenzilate (975)+COMPOUND OF FORMULA I, chloromebuform (977)+COMPOUND OF FORMULA I, chloromethiuron (978)+COMPOUND OF FORMULA I, chloropropylate (983)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, cinerin I (696)+COMPOUND OF FORMULA I, cinerin II (696)+COMPOUND OF FORMULA I, cinerins (696)+COMPOUND OF FORMULA I, clofentezine (158)+COMPOUND OF FORMULA I, closantel (alternative name) [CCN]+COMPOUND OF FORMULA I, coumaphos (174)+COMPOUND OF FORMULA I, crotamiton (alternative name) [CCN]+COMPOUND OF FORMULA I, crotoxyphos (1010)+COMPOUND OF FORMULA I, cufraneb (1013)+COMPOUND OF FORMULA I, cyanthoate (1020)+COMPOUND OF FORMULA I, cyenopyrafen [CCN]+COMPOUND OF FORMULA I, cyflumetofen (CAS Reg. No.: 400882-07-7)+COMPOUND OF FORMULA I, cyhalothrin (196)+COMPOUND OF FORMULA I, cyhexatin (199)+COMPOUND OF FORMULA I, cypermethrin (201)+COMPOUND OF FORMULA I, DCPM (1032)+COMPOUND OF FORMULA I, DDT (219)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diazinon (227)+COMPOUND OF FORMULA I, dichlofluanid (230)+COMPOUND OF FORMULA I, dichlorvos (236)+COMPOUND OF FORMULA I, dicliphos (alternative name)+COMPOUND OF FORMULA I, dicofol (242)+COMPOUND OF FORMULA I, dicrotophos (243)+COMPOUND OF FORMULA I, dienochlor (1071)+COMPOUND OF FORMULA I, diflovidazin [CCN]+COMPOUND OF FORMULA I, dimefox (1081)+COMPOUND OF FORMULA I, dimethoate (262)+COMPOUND OF FORMULA I, dinactin (alternative name) (653)+COMPOUND OF FORMULA I, dinex (1089)+COMPOUND OF FORMULA I, dinex-diclexine (1089)+COMPOUND OF FORMULA I, dinobuton (269)+COMPOUND OF FORMULA I, dinocap (270)+COMPOUND OF FORMULA I, dinocap-4 [CCN]+COMPOUND OF FORMULA I, dinocap-6 [CCN]+COMPOUND OF FORMULA I, dinocton (1090)+COMPOUND OF FORMULA I, dinopenton (1092)+COMPOUND OF FORMULA I, dinosulfon (1097)+COMPOUND OF FORMULA I, dinoterbon (1098)+COMPOUND OF FORMULA I, dioxathion (1102)+COMPOUND OF FORMULA I, diphenyl sulfone (IUPAC name) (1103)+COMPOUND OF FORMULA I, disulfuram (alternative name) [CCN]+COMPOUND OF FORMULA I, disulfoton (278)+COMPOUND OF FORMULA I, DNOC (282)+COMPOUND OF FORMULA I, dofenapyn (1113)+COMPOUND OF FORMULA I, doramectin (alternative name) [CCN]+COMPOUND OF FORMULA I, endosulfan (294)+COMPOUND OF FORMULA I, endothion (1121)+COMPOUND OF FORMULA I, EPN (297)+COMPOUND OF FORMULA I, eprinomectin (alternative name) [CCN]+COMPOUND OF FORMULA I, ethion (309)+COMPOUND OF FORMULA I, ethoate-methyl (1134)+COMPOUND OF FORMULA I, etoxazole (320)+COMPOUND OF FORMULA I, etrimfos (1142)+COMPOUND OF FORMULA I, fenazaflor (1147)+COMPOUND OF FORMULA I, fenazaquin (328)+COMPOUND OF FORMULA I, fenbutatin oxide (330)+COMPOUND OF FORMULA I, fenothiocarb (337)+COMPOUND OF FORMULA I, fenpropathrin (342)+COMPOUND OF FORMULA I, fenpyrad (alternative name)+COMPOUND OF FORMULA I, fenpyroximate (345)+COMPOUND OF FORMULA I, fenson (1157)+COMPOUND OF FORMULA I, fentrifanil (1161)+COMPOUND OF FORMULA I, fenvalerate (349)+COMPOUND OF FORMULA I, fipronil (354)+COMPOUND OF FORMULA I, fluacrypyrim (360)+COMPOUND OF FORMULA I, fluazuron (1166)+COMPOUND OF FORMULA I, flubenzimine (1167)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, flufenoxuron (370)+COMPOUND OF FORMULA I, flumethrin (372)+COMPOUND OF FORMULA I, fluorbenside (1174)+COMPOUND OF FORMULA I, fluvalinate (1184)+COMPOUND OF FORMULA I, FMC 1137 (development code) (1185)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, gamma-HCH (430)+COMPOUND OF FORMULA I, glyodin (1205)+COMPOUND OF FORMULA I, halfenprox (424)+COMPOUND OF FORMULA I, heptenophos (432)+COMPOUND OF FORMULA I, hexadecyl cyclopropanecarboxylate (IUPAC/Chemical Abstracts name) (1216)+COMPOUND OF FORMULA I, hexythiazox (441)+COMPOUND OF FORMULA I, IKA 2002 (CAS Reg. No.: 211923-74-9)+COMPOUND OF FORMULA I, iodomethane (IUPAC name) (542)+COMPOUND OF FORMULA I, isocarbophos (alternative name) (473)+COMPOUND OF FORMULA I, isopropyl O-(methoxyaminothiophosphoryl)salicylate (IUPAC name) (473)+COMPOUND OF FORMULA I, ivermectin (alternative name) [CCN]+COMPOUND OF FORMULA I, jasmolin I (696)+COMPOUND OF FORMULA I, jasmolin II (696)+COMPOUND OF FORMULA I, jodfenphos (1248)+COMPOUND OF FORMULA I, lindane (430)+COMPOUND OF FORMULA I, lufenuron (490)+COMPOUND OF FORMULA I, malathion (492)+COMPOUND OF FORMULA I, malonoben (1254)+COMPOUND OF FORMULA I, mecarbam (502)+COMPOUND OF FORMULA I, mephosfolan (1261)+COMPOUND OF FORMULA I, mesulfen (alternative name) [CCN]+COMPOUND OF FORMULA I, methacrifos (1266)+COMPOUND OF FORMULA I, methamidophos (527)+COMPOUND OF FORMULA I, methidathion (529)+COMPOUND OF FORMULA I, methiocarb (530)+COMPOUND OF FORMULA I, methomyl (531)+COMPOUND OF FORMULA I, methyl bromide (537)+COMPOUND OF FORMULA I, metolcarb (550)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naled (567)+COMPOUND OF FORMULA I, NC-184 (compound code)+COMPOUND OF FORMULA I, NC-512 (compound code)+COMPOUND OF FORMULA I, nifluridide (1309)+COMPOUND OF FORMULA I, nikkomycins (alternative name) [CCN]+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, omethoate (594)+COMPOUND OF FORMULA I, oxamyl (602)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, parathion (615)+COMPOUND OF FORMULA I, permethrin (626)+

COMPOUND OF FORMULA I, petroleum oils (alternative name) (628)+COMPOUND OF FORMULA I, phenkapton (1330)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosphamidon (639)+COMPOUND OF FORMULA I, phoxim (642)+COMPOUND OF FORMULA I, pirimiphos-methyl (652)+COMPOUND OF FORMULA I, polychloroterpenes (traditional name) (1347)+COMPOUND OF FORMULA I, polynactins (alternative name) (653)+COMPOUND OF FORMULA I, proclonol (1350)+COMPOUND OF FORMULA I, profenofos (662)+COMPOUND OF FORMULA I, promacyl (1354)+COMPOUND OF FORMULA I, propargite (671)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothoate (1362)+COMPOUND OF FORMULA I, pyrethrin I (696)+COMPOUND OF FORMULA I, pyrethrin II (696)+COMPOUND OF FORMULA I, pyrethrins (696)+COMPOUND OF FORMULA I, pyridaben (699)+COMPOUND OF FORMULA I, pyridaphenthion (701)+COMPOUND OF FORMULA I, pyrimidifen (706)+COMPOUND OF FORMULA I, pyrimitate (1370)+COMPOUND OF FORMULA I, quinalphos (711)+COMPOUND OF FORMULA I, quintiofos (1381)+COMPOUND OF FORMULA I, R-1492 (development code) (1382)+COMPOUND OF FORMULA I, RA-17 (development code) (1383)+COMPOUND OF FORMULA I, rotenone (722)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, sophamide (1402)+COMPOUND OF FORMULA I, spirodiclofen (738)+COMPOUND OF FORMULA I, spiromesifen (739)+COMPOUND OF FORMULA I, SSI-121 (development code) (1404)+COMPOUND OF FORMULA I, sulfuram (alternative name) [CCN]+COMPOUND OF FORMULA I, sulfluramid (750)+COMPOUND OF FORMULA I, sulfotep (753)+COMPOUND OF FORMULA I, sulfur (754)+COMPOUND OF FORMULA I, SZI-121 (development code) (757)+COMPOUND OF FORMULA I, tau-fluvalinate (398)+COMPOUND OF FORMULA I, tebufenpyrad (763)+COMPOUND OF FORMULA I, TEPP (1417)+COMPOUND OF FORMULA I, terbam (alternative name)+COMPOUND OF FORMULA I, tetrachlorvinphos (777)+COMPOUND OF FORMULA I, tetradifon (786)+COMPOUND OF FORMULA I, tetranactin (alternative name) (653)+COMPOUND OF FORMULA I, tetrasul (1425)+COMPOUND OF FORMULA I, thiafenox (alternative name)+COMPOUND OF FORMULA I, thiocarboxime (1431)+COMPOUND OF FORMULA I, thiofanox (800)+COMPOUND OF FORMULA I, thiometon (801)+COMPOUND OF FORMULA I, thioquinox (1436)+COMPOUND OF FORMULA I, thuringiensin (alternative name) [CCN]+COMPOUND OF FORMULA I, triamiphos (1441)+COMPOUND OF FORMULA I, triarathene (1443)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trifenofos (1455)+COMPOUND OF FORMULA I, trinactin (alternative name) (653)+COMPOUND OF FORMULA I, vamidothion (847)+COMPOUND OF FORMULA I, vaniliprole [CCN] and YI-5302 (compound code)+COMPOUND OF FORMULA I, an algicide selected from the group of substances consisting of bethoxazin [CCN]+COMPOUND OF FORMULA I, copper dioctanoate (IUPAC name) (170)+COMPOUND OF FORMULA I, copper sulfate (172)+COMPOUND OF FORMULA I, cybutryne [CCN]+COMPOUND OF FORMULA I, dichlone (1052)+COMPOUND OF FORMULA I, dichlorophen (232)+COMPOUND OF FORMULA I, endothal (295)+COMPOUND OF FORMULA I, fentin (347)+COMPOUND OF FORMULA I, hydrated lime [CCN]+COMPOUND OF FORMULA I, nabam (566)+COMPOUND OF FORMULA I, quinoclamine (714)+COMPOUND OF FORMULA I, quinonamid (1379)+COMPOUND OF FORMULA I, simazine (730)+COMPOUND OF FORMULA I, triphenyltin acetate (IUPAC name) (347) and triphenyltin hydroxide (IUPAC name) (347)+COMPOUND OF FORMULA I, an anthelmintic selected from the group of substances consisting of abamectin (1)+COMPOUND OF FORMULA I, crufomate (1011)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ivermectin (alternative name) [CCN]+COMPOUND OF FORMULA I, milbemycin oxime (alternative name) [CCN]+COMPOUND OF FORMULA I, moxidectin (alternative name) [CCN]+COMPOUND OF FORMULA I, piperazine [CCN]+COMPOUND OF FORMULA I, selamectin (alternative name) [CCN]+COMPOUND OF FORMULA I, spinosad (737) and thiophanate (1435)+COMPOUND OF FORMULA I, an avicide selected from the group of substances consisting of chloralose (127)+COMPOUND OF FORMULA I, endrin (1122)+COMPOUND OF FORMULA I, fenthion (346)+COMPOUND OF FORMULA I, pyridin-4-amine (IUPAC name) (23) and strychnine (745)+COMPOUND OF FORMULA I, a bactericide selected from the group of substances consisting of 1-hydroxy-1H-pyridine-2-thione (IUPAC name) (1222)+COMPOUND OF FORMULA 1,4-(quinoxalin-2-ylamino)benzenesulfonamide (IUPAC name) (748)+COMPOUND OF FORMULA 1,8-hydroxyquinoline sulfate (446)+COMPOUND OF FORMULA I, bronopol (97)+COMPOUND OF FORMULA I, copper dioctanoate (IUPAC name) (170)+COMPOUND OF FORMULA I, copper hydroxide (IUPAC name) (169)+COMPOUND OF FORMULA I, cresol [CCN]+COMPOUND OF FORMULA I, dichlorophen (232)+COMPOUND OF FORMULA I, dipyrithione (1105)+COMPOUND OF FORMULA I, dodicin (1112)+COMPOUND OF FORMULA I, fenaminosulf (1144)+COMPOUND OF FORMULA I, formaldehyde (404)+COMPOUND OF FORMULA I, hydrargaphen (alternative name) [CCN]+COMPOUND OF FORMULA I, kasugamycin (483)+COMPOUND OF FORMULA I, kasugamycin hydrochloride hydrate (483)+COMPOUND OF FORMULA I, nickel bis(dimethyldithiocarbamate) (IUPAC name) (1308)+COMPOUND OF FORMULA I, nitrapyrin (580)+COMPOUND OF FORMULA I, octhilinone (590)+COMPOUND OF FORMULA I, oxolinic acid (606)+COMPOUND OF FORMULA I, oxytetracycline (611)+COMPOUND OF FORMULA I, potassium hydroxyquinoline sulfate (446)+COMPOUND OF FORMULA I, probenazole (658)+COMPOUND OF FORMULA I, streptomycin (744)+COMPOUND OF FORMULA I, streptomycin sesquisulfate (744)+COMPOUND OF FORMULA I, tecloftalam (766)+COMPOUND OF FORMULA I, and thiomersal (alternative name) [CCN]+COMPOUND OF FORMULA I, a biological agent selected from the group of substances consisting of *Adoxophyes orana* GV (alternative name) (12)+COMPOUND OF FORMULA I, *Agrobacterium radiobacter* (alternative name) (13)+COMPOUND OF FORMULA I, *Amblyseius* spp. (alternative name) (19)+COMPOUND OF FORMULA I, *Anagrapha falcifera* NPV (alternative name) (28)+COMPOUND OF FORMULA I, *Anagrus atomus* (alternative name) (29)+COMPOUND OF FORMULA I, *Aphelinus abdominalis* (alternative name) (33)+COMPOUND OF FORMULA I, *Aphidius colemani* (alternative name) (34)+COMPOUND OF FORMULA I, *Aphidoletes aphidimyza* (alternative name) (35)+COMPOUND OF FORMULA I, *Autographa californica* NPV (alternative name) (38)+COMPOUND OF FORMULA I, *Bacillus firmus* (alternative name) (48)+COMPOUND OF FORMULA I, *Bacillus sphaericus* Neide (scientific name) (49)+COMPOUND OF FORMULA I, *Bacillus thuringiensis* Berliner (scientific name) (51)+COMPOUND OF FORMULA I, *Bacillus thuringiensis* subsp. *aizawai* (scientific name) (51)+COMPOUND OF FORMULA I, *Bacillus thuringiensis* subsp. *israelensis* (scientific name) (51)+COMPOUND OF FORMULA I, *Bacillus thuringiensis* subsp. *japonensis* (scientific name) (51)+COMPOUND OF FORMULA I, *Bacillus thuringiensis* subsp. *kurstaki* (scientific name) (51)+COMPOUND OF FORMULA I, *Bacillus thuringiensis* subsp. *tenebrionis* (scientific name) (51)+COMPOUND OF FORMULA I, *Beauveria bassiana* (alternative name) (53)+COMPOUND OF FORMULA I, *Beauveria brongniartii* (alternative name) (54)+COMPOUND OF FORMULA I, *Chrysoperla carnea* (alternative name) (151)+COMPOUND OF FORMULA I, *Cryptolaemus montrouzieri* (alternative name) (178)+COMPOUND OF FORMULA I, *Cydia pomonella* GV (alternative name) (191)+COMPOUND OF FORMULA I, *Dacnusa sibirica* (alternative name) (212)+COMPOUND OF FORMULA I, *Diglyphus isaea* (alternative name) (254)+COMPOUND OF FORMULA I, *Encarsia formosa* (scientific name) (293)+COMPOUND OF FORMULA I, *Eretmocerus eremicus* (alternative name) (300)+COMPOUND OF FORMULA I, *Helicoverpa zea* NPV (alternative name) (431)+COMPOUND OF FORMULA I, *Heterorhabditis bacteriophora* and *H. megidis* (alternative name) (433)+COMPOUND OF FORMULA I, *Hippodamia convergens* (alternative name) (442)+COMPOUND OF FORMULA I, *Leptomastix dactylopii* (alternative name) (488)+COMPOUND OF FORMULA I, *Macrolophus caliginosus* (alternative name) (491)+COMPOUND OF FORMULA I, *Mamestra brassicae* NPV (alternative name) (494)+COMPOUND OF FORMULA I, *Metaphycus helvolus* (alternative name) (522)+COMPOUND OF FORMULA I, *Metarhizium anisopliae* var. *acridum* (scientific name) (523)+COMPOUND OF FORMULA I, *Metarhizium anisopliae* var. *anisopliae* (scientific name) (523)+COMPOUND OF FORMULA I, *Neodiprion sertifer* NPV and *N. lecontei* NPV (alternative name) (575)+COMPOUND OF FORMULA I, *Orius* spp. (alternative name) (596)+COMPOUND OF FORMULA I, *Paecilomyces fumosoroseus* (alternative name) (613)+COMPOUND OF FORMULA I, *Phytoseiulus persimilis* (alternative name) (644)+COMPOUND OF FORMULA I, *Spodoptera exigua* multicapsid nuclear polyhedrosis virus (scientific name) (741)+COMPOUND OF FORMULA I, *Steinernema bibionis* (alternative name) (742)+COMPOUND OF FORMULA I, *Steinernema carpocapsae* (alternative name) (742)+COMPOUND OF FORMULA I, *Steinernema feltiae* (alternative name) (742)+COMPOUND OF FORMULA I, *Steinernema glaseri* (alternative name) (742)+COMPOUND OF FORMULA I, *Steinernema riobrave* (alternative name) (742)+COMPOUND OF FORMULA I, *Steinernema riobravis* (alternative name) (742)+COMPOUND OF FORMULA I, *Steinernema scapterisci* (alternative name) (742)+COMPOUND OF FORMULA I, *Steinernema* spp. (alternative name) (742)+COMPOUND OF FORMULA I, *Trichogramma* spp. (alternative name) (826)+COMPOUND OF FORMULA I, *Typhlodromus occidentalis* (alternative name) (844) and *Verticillium lecanii* (alternative name) (848)+COMPOUND OF FORMULA I, a soil sterilant selected from the group of substances consisting of iodomethane (IUPAC name) (542) and methyl bromide (537)+COMPOUND OF FORMULA I, a chemosterilant selected from the group of substances consisting of apholate [CCN]+COMPOUND OF FORMULA I, bisazir (alternative name) [CCN]+COMPOUND OF FORMULA I, busulfan (alternative name) [CCN]+COMPOUND OF FORMULA I, diflubenzuron (250)+COMPOUND OF FORMULA I, dimatif (alternative name) [CCN]+COMPOUND OF FORMULA I, hemel [CCN]+COMPOUND OF FORMULA I, hempa [CCN]+COMPOUND OF FORMULA I, metepa [CCN]+COMPOUND OF FORMULA I, methiotepa [CCN]+COMPOUND OF FORMULA I, methyl apholate [CCN]+COMPOUND OF FORMULA I, morzid [CCN]+COMPOUND OF FORMULA I, penfluoron (alternative name) [CCN]+COMPOUND OF FORMULA I, tepa [CCN]+COMPOUND OF FORMULA I, thiohempa (alternative name) [CCN]+COMPOUND OF FORMULA I, thiotepa (alternative name) [CCN]+COMPOUND OF FORMULA I, tretamine (alternative name) [CCN] and uredepa (alternative name) [CCN]+COMPOUND OF FORMULA I, an insect pheromone selected from the group of substances consisting of (E)-dec-5-en-1-yl acetate with (E)-dec-5-en-1-ol (IUPAC name) (222)+COMPOUND OF FORMULA I, (E)-tridec-4-en-1-yl acetate (IUPAC name) (829)+COMPOUND OF FORMULA I, (E)-6-methylhept-2-en-4-ol (IUPAC name) (541)+COMPOUND OF FORMULA I, (E,Z)-tetradeca-4,10-dien-1-yl acetate (IUPAC name) (779)+COMPOUND OF FORMULA I, (Z)-dodec-7-en-1-yl acetate (IUPAC name) (285)+COMPOUND OF FORMULA I, (Z)-hexadec-11-enal (IUPAC name) (436)+COMPOUND OF FORMULA I, (Z)-hexadec-11-en-1-yl acetate (IUPAC name) (437)+COMPOUND OF FORMULA I, (Z)-hexadec-13-en-11-yn-1-yl acetate (IUPAC name) (438)+COMPOUND OF FORMULA I, (Z)-icos-13-en-10-one (IUPAC name) (448)+COMPOUND OF FORMULA I, (Z)-tetradec-7-en-1-al (IUPAC name) (782)+COMPOUND OF FORMULA I, (Z)-tetradec-9-en-1-ol (IUPAC name) (783)+COMPOUND OF FORMULA I, (Z)-tetradec-9-en-1-yl acetate (IUPAC name) (784)+COMPOUND OF FORMULA I, (7E,9Z)-dodeca-7,9-dien-1-yl acetate (IUPAC name) (283)+COMPOUND OF FORMULA I, (9Z,11E)-tetradeca-9,11-dien-1-yl acetate (IUPAC name) (780)+COMPOUND OF FORMULA I, (9Z,12E)-tetradeca-9,12-dien-1-yl acetate (IUPAC name) (781)+COMPOUND OF FORMULA 1,14-methyloctadec-1-ene (IUPAC name) (545)+COMPOUND OF FORMULA 1,4-methylnonan-5-ol with 4-methylnonan-5-one (IUPAC name) (544)+COMPOUND OF FORMULA I, alpha-multistriatin (alternative name) [CCN]+COMPOUND OF FORMULA I, brevicomin (alternative name) [CCN]+COMPOUND OF FORMULA I, codlelure (alternative name) [CCN]+COMPOUND OF FORMULA I, codlemone (alternative name) (167)+COM- POUND OF FORMULA I, cuelure (alternative name) (179)+COMPOUND OF FORMULA I, disparlure (277)+COMPOUND OF FORMULA I, dodec-8-en-1-yl acetate (IUPAC name) (286)+COMPOUND OF FORMULA I, dodec-9-en-1-yl acetate (IUPAC name) (287)+COMPOUND OF FORMULA I, dodeca-8+COMPOUND OF FORMULA 1,10-dien-1-yl acetate (IUPAC name) (284)+COMPOUND OF FORMULA I, dominicalure (alternative name) [CCN]+COMPOUND OF FORMULA I, ethyl 4-methyloctanoate (IUPAC name) (317)+COMPOUND OF FORMULA I, eugenol (alternative name) [CCN]+COMPOUND OF FORMULA I, frontalin (alternative name) [CCN]+COMPOUND OF FORMULA I, gossyplure (alternative name) (420)+COMPOUND OF FORMULA I, grandlure (421)+COMPOUND OF FORMULA I, grandlure I (alternative name) (421)+COMPOUND OF FORMULA I, grandlure II (alternative name) (421)+COMPOUND OF FORMULA I, grandlure III (alternative name) (421)+COMPOUND OF FORMULA I, grandlure IV (alternative name) (421)+COMPOUND OF FORMULA I, hexylure [CCN]+COMPOUND OF FORMULA I, ipsdienol (alternative name) [CCN]+COMPOUND OF FORMULA I, ipsenol (alternative name) [CCN]+COMPOUND OF FORMULA I, japonilure (alternative name) (481)+COMPOUND OF FORMULA I, lineatin (alternative name) [CCN]+COMPOUND OF FORMULA I, litlure (alternative name) [CCN]+COMPOUND OF FORMULA I, looplure (alternative name) [CCN]+COMPOUND OF FORMULA I, medlure [CCN]+COMPOUND OF FORMULA I, megatomoic acid (alternative name) [CCN]+COMPOUND OF FORMULA I, methyl eugenol (alternative name) (540)+COMPOUND OF FORMULA I, muscalure (563)+COMPOUND OF FORMULA I, octadeca-2,13-dien-1-yl acetate (IUPAC name) (588)+COMPOUND OF FORMULA I, octadeca-3,13-dien-1-yl acetate (IUPAC name) (589)+COMPOUND OF FORMULA I, orfralure (alternative name) [CCN]+COMPOUND OF FORMULA I, oryctalure (alternative name) (317)+COMPOUND OF FORMULA I, ostramone (alternative name) [CCN]+COMPOUND OF FORMULA I, siglure [CCN]+COMPOUND OF FORMULA I, sordidin (alternative name) (736)+COMPOUND OF FORMULA I, sulcatol (alternative name) [CCN]+COMPOUND OF FORMULA I, tetradec-11-en-1-yl acetate (IUPAC name) (785)+COMPOUND OF FORMULA I, trimedlure (839)+COMPOUND OF FORMULA I, trimedlure A (alternative name) (839)+COMPOUND OF FORMULA I, trimedlure $B_1$ (alternative name) (839)+COMPOUND OF FORMULA I, trimedlure $B_2$ (alternative name) (839)+COMPOUND OF FORMULA I, trimedlure C (alternative name) (839) and trunc-call (alternative name) [CCN]+COMPOUND OF FORMULA I, an insect repellent selected from the group of substances consisting of 2-(octylthio)-ethanol (IUPAC name) (591)+COMPOUND OF FORMULA I, butopyronoxyl (933)+COMPOUND OF FORMULA I, butoxy(polypropylene glycol) (936)+COMPOUND OF FORMULA I, dibutyl adipate (IUPAC name) (1046)+COMPOUND OF FORMULA I, dibutyl phthalate (1047)+COMPOUND OF FORMULA I, dibutyl succinate (IUPAC name) (1048)+COMPOUND OF FORMULA I, diethyltoluamide [CCN]+COMPOUND OF FORMULA I, dimethyl carbate [CCN]+COMPOUND OF FORMULA I, dimethyl phthalate [CCN]+COMPOUND OF FORMULA I, ethyl hexanediol (1137)+COMPOUND OF FORMULA I, hexamide [CCN]+COMPOUND OF FORMULA I, methoquin-butyl (1276)+COMPOUND OF FORMULA I, methylneodecanamide [CCN]+COMPOUND OF FORMULA I, oxamate [CCN] and picaridin [CCN]+COMPOUND OF FORMULA I, an insecticide selected from the group of substances consisting of 1-dichloro-1-nitroethane (IUPAC/Chemical Abstracts name) (1058)+COMPOUND OF FORMULA I, 1,1-dichloro-2,2-bis(4-ethylphenyl)ethane (IUPAC name) (1056), +COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1-bromo-2-chloroethane (IUPAC/Chemical Abstracts name) (916)+COMPOUND OF FORMULA 1,2,2,2-trichloro-1-(3,4-dichlorophenyl)ethyl acetate (IUPAC name) (1451)+COMPOUND OF FORMULA 1,2,2-dichlorovinyl 2-ethylsulfinylethyl methyl phosphate (IUPAC name) (1066)+COMPOUND OF FORMULA I, 2-(1,3-dithiolan-2-yl)phenyl dimethylcarbamate (IUPAC/Chemical Abstracts name) (1109)+COMPOUND OF FORMULA I, 2-(2-butoxyethoxy)ethyl thiocyanate (IUPAC/Chemical Abstracts name) (935)+COMPOUND OF FORMULA I, 2-(4,5-dimethyl-1,3-dioxolan-2-yl)phenyl methylcarbamate (IUPAC/Chemical Abstracts name) (1084)+COMPOUND OF FORMULA I, 2-(4-chloro-3,5-xylyloxy)ethanol (IUPAC name) (986)+COMPOUND OF FORMULA I, 2-chlorovinyl diethyl phosphate (IUPAC name) (984)+COMPOUND OF FORMULA I, 2-imidazolidone (IUPAC name) (1225)+COMPOUND OF FORMULA I, 2-isovalerylindan-1,3-dione (IUPAC name) (1246)+COMPOUND OF FORMULA I, 2-methyl(prop-2-ynyl)aminophenyl methylcarbamate (IUPAC name) (1284)+COMPOUND OF FORMULA I, 2-thiocyanatoethyl laurate (IUPAC name) (1433)+COMPOUND OF FORMULA I, 3-bromo-1-chloroprop-1-ene (IUPAC name) (917)+COMPOUND OF FORMULA I, 3-methyl-1-phenylpyrazol-5-yl dimethylcarbamate (IUPAC name) (1283)+COMPOUND OF FORMULA I, 4-methyl(prop-2-ynyl)amino-3,5-xylylmethylcarbamate (IUPAC name) (1285)+COMPOUND OF FORMULA I, 5,5-dimethyl-3-oxocyclohex-1-enyl dimethylcarbamate (IUPAC name) (1085)+COMPOUND OF FORMULA I, abamectin (1)+COMPOUND OF FORMULA I, acephate (2)+COMPOUND OF FORMULA I, acetamiprid (4)+COMPOUND OF FORMULA I, acethion (alternative name) [CCN]+COMPOUND OF FORMULA I, acetoprole [CCN]+COMPOUND OF FORMULA I, acrinathrin (9)+COMPOUND OF FORMULA I, acrylonitrile (IUPAC name) (861)+COMPOUND OF FORMULA I, alanycarb (15)+COMPOUND OF FORMULA I, aldicarb (16)+COMPOUND OF FORMULA I, aldoxycarb (863)+COMPOUND OF FORMULA I, aldrin (864)+COMPOUND OF FORMULA I, allethrin (17)+COMPOUND OF FORMULA I, allosamidin (alternative name) [CCN]+COMPOUND OF FORMULA I, allyxycarb (866)+COMPOUND OF FORMULA I, alpha-cypermethrin (202)+COMPOUND OF FORMULA I, alpha-ecdysone (alternative name) [CCN]+COMPOUND OF FORMULA I, alpha-endosulfan [CCN]+COMPOUND OF FORMULA I, aluminium phosphide (640)+COMPOUND OF FORMULA I, amidithion (870)+COMPOUND OF FORMULA I, amidothioate (872)+COMPOUND OF FORMULA I, aminocarb (873)+COMPOUND OF FORMULA I, amiton (875)+COMPOUND OF FORMULA I, amiton hydrogen oxalate (875)+COMPOUND OF FORMULA I, amitraz (24)+COMPOUND OF FORMULA I, anabasine (877)+COMPOUND OF FORMULA I, athidathion (883)+COMPOUND OF FORMULA I, AVI 382 (compound code)+COMPOUND OF FORMULA I, AZ 60541 (compound code)+COMPOUND OF FORMULA I, azadirachtin (alternative name) (41)+COMPOUND OF FORMULA I, azamethiphos (42)+COMPOUND OF FORMULA I, azinphos-ethyl (44)+COMPOUND OF FORMULA I, azinphos-methyl (45)+COMPOUND OF FORMULA I, azothoate (889)+COMPOUND OF FORMULA I, *Bacillus thuringiensis* delta endotoxins (alternative name) (52)+COMPOUND OF FORMULA I, barium hexafluorosilicate (alternative name) [CCN]+COMPOUND OF FORMULA I, barium polysulfide (IUPAC/Chemical Abstracts name) (892)+COMPOUND OF FORMULA I, barthrin [CCN]+COMPOUND OF FORMULA I, Bayer 22/190 (development code) (893)+COMPOUND OF FORMULA I, Bayer 22408 (development code) (894)+COMPOUND OF FORMULA I, bendiocarb (58)+COMPOUND OF FORMULA I, benfuracarb (60)+COMPOUND OF FORMULA I, bensultap (66)+COMPOUND OF FORMULA I, beta-cyfluthrin (194)+COMPOUND OF FORMULA I, beta-cypermethrin (203)+COMPOUND OF FORMULA I, bifenthrin (76)+COMPOUND OF FORMULA I, bioallethrin (78)+COMPOUND OF FORMULA I, bioallethrin S-cyclopentenyl isomer (alternative name) (79)+COMPOUND OF FORMULA I, bioethanomethrin [CCN]+COMPOUND OF FORMULA I, biopermethrin (908)+COMPOUND OF FORMULA I, bioresmethrin (80)+COMPOUND OF FORMULA I, bis(2-chloroethyl)ether (IUPAC name) (909)+COMPOUND OF FORMULA I, bistrifluoron (83)+COMPOUND OF FORMULA I, borax (86)+COMPOUND OF FORMULA I, brofenvalerate (alternative name)+COMPOUND OF FORMULA I, bromfenvinfos (914)+COMPOUND OF FORMULA I, bromocyclen (918)+COMPOUND OF FORMULA I, bromo-DDT (alternative name) [CCN]+COMPOUND OF FORMULA I, bromophos (920)+COMPOUND OF FORMULA I, bromophos-ethyl (921)+COMPOUND OF FORMULA I, bufencarb (924)+COMPOUND OF FORMULA I, buprofezin (99)+COMPOUND OF FORMULA I, butacarb (926)+COMPOUND OF FORMULA I, butathiofos (927)+COMPOUND OF FORMULA I, butocarboxim (103)+COMPOUND OF FORMULA I, butonate (932)+COMPOUND OF FORMULA I, butoxycarboxim (104)+COMPOUND OF FORMULA I, butylpyridaben (alternative name)+COMPOUND OF FORMULA I, cadusafos (109)+COMPOUND OF FORMULA I, calcium arsenate [CCN]+COMPOUND OF FORMULA I, calcium cyanide (444)+COMPOUND OF FORMULA I, calcium polysulfide (IUPAC name) (111)+COMPOUND OF FORMULA I, camphechlor (941)+COMPOUND OF FORMULA I, carbanolate (943)+COMPOUND OF FORMULA I, carbaryl (115)+COMPOUND OF FORMULA I, carbofuran (118)+COMPOUND OF FORMULA I, carbon disulfide (IUPAC/Chemical Abstracts name) (945)+COMPOUND OF FORMULA I, carbon tetrachloride (IUPAC name) (946)+COMPOUND OF FORMULA I, carbophenothion (947)+COMPOUND OF FORMULA I, carbosulfan (119)+COMPOUND OF FORMULA I, cartap (123)+COMPOUND OF FORMULA I, cartap hydrochloride (123)+COMPOUND OF FORMULA I, cevadine (alternative name) (725)+COMPOUND OF FORMULA I, chlorantraniliprole [CCN]+COMPOUND OF FORMULA I, chlorbicyclen (960)+COMPOUND OF FORMULA I, chlordane (128)+COMPOUND OF FORMULA I, chlordecone (963)+COMPOUND OF FORMULA I, chlordimeform (964)+COMPOUND OF FORMULA I, chlordimeform hydrochloride (964)+COMPOUND OF FORMULA I, chlorethoxyfos (129)+COMPOUND OF FORMULA I, chlorfenapyr (130)+COMPOUND OF FORMULA I, chlorfenvinphos (131)+COMPOUND OF FORMULA I, chlorfluazuron (132)+COMPOUND OF FORMULA I, chlormephos (136)+COMPOUND OF FORMULA I, chloroform [CCN]+COMPOUND OF FORMULA I, chloropicrin (141)+COMPOUND OF FORMULA I, chlorphoxim (989)+COMPOUND OF FORMULA I, chlorprazophos (990)+COMPOUND OF FORMULA I, chlorpyrifos (145)+COMPOUND OF FORMULA I, chlorpyrifos-methyl (146)+COMPOUND OF FORMULA I, chlorthiophos (994)+COMPOUND OF FORMULA I, chromafenozide (150)+COMPOUND OF FORMULA I, cinerin I (696)+COMPOUND OF FORMULA I, cinerin II (696)+COMPOUND OF FORMULA I, cinerins (696)+COMPOUND OF FORMULA I, cis-resmethrin (alternative name)+COMPOUND OF FORMULA I, cismethrin (80)+COMPOUND OF FORMULA I, clocythrin (alternative name)+COMPOUND OF FORMULA I, cloethocarb (999)+COMPOUND OF FORMULA I, closantel (alternative name) [CCN]+COMPOUND OF FORMULA I, clothianidin (165)+COMPOUND OF FORMULA I, copper acetoarsenite [CCN]+COMPOUND OF FORMULA I, copper arsenate [CCN]+COMPOUND OF FORMULA I, copper oleate [CCN]+COMPOUND OF FORMULA I, coumaphos (174)+COMPOUND OF FORMULA I, coumithoate (1006)+COMPOUND OF FORMULA I, crotamiton (alternative name) [CCN]+COMPOUND OF FORMULA I, crotoxyphos (1010)+COMPOUND OF FORMULA I, crufomate (1011)+COMPOUND OF FORMULA I, cryolite (alternative name) (177)+COMPOUND OF FORMULA I, CS 708 (development code) (1012)+COMPOUND OF FORMULA I, cyanofenphos (1019)+COMPOUND OF FORMULA I, cyanophos (184)+COMPOUND OF FORMULA I, cyanthoate (1020)+COMPOUND OF FORMULA I, cyantraniliprole [CCN]+COMPOUND OF FORMULA I, cyclethrin [CCN]+COMPOUND OF FORMULA I, cycloprothrin (188)+COMPOUND OF FORMULA I, cyfluthrin (193)+COMPOUND OF FORMULA I, cyhalothrin (196)+COMPOUND OF FORMULA I, cypermethrin (201)+COMPOUND OF FORMULA I, cyphenothrin (206)+COMPOUND OF FORMULA I, cyromazine (209)+COMPOUND OF FORMULA I, cythioate (alternative name) [CCN]+COMPOUND OF FORMULA I, d-limonene (alternative name) [CCN]+COMPOUND OF FORMULA I, d-tetramethrin (alternative name) (788)+COMPOUND OF FORMULA I, DAEP (1031)+COMPOUND OF FORMULA I, dazomet (216)+COMPOUND OF FORMULA I, DDT (219)+COMPOUND OF FORMULA I, decarbofuran (1034)+COMPOUND OF FORMULA I, deltamethrin (223)+COMPOUND OF FORMULA I, demephion (1037)+COMPOUND OF FORMULA I, demephion-O (1037)+COMPOUND OF FORMULA I, demephion-S (1037)+COMPOUND OF FORMULA I, demeton (1038)+COMPOUND OF FORMULA I, demeton-methyl (224)+COMPOUND OF FORMULA I, demeton-O (1038)+COMPOUND OF FORMULA I, demeton-O-methyl (224)+COMPOUND OF FORMULA I, demeton-S (1038)+COMPOUND OF FORMULA I, demeton-S-methyl (224)+COMPOUND OF FORMULA I, demeton-S-methylsulphon (1039)+COMPOUND OF FORMULA I, diafenthiuron (226)+COMPOUND OF FORMULA I, dialifos (1042)+COMPOUND OF FORMULA I, diamidafos (1044)+COMPOUND OF FORMULA I, diazinon (227)+COMPOUND OF FORMULA I, dicapthon (1050)+COMPOUND OF FORMULA I, dichlofenthion (1051)+COMPOUND OF FORMULA I, dichlorvos (236)+COMPOUND OF FORMULA I, dicliphos (alternative name)+COMPOUND OF FORMULA I, dicresyl (alternative name) [CCN]+COMPOUND OF FORMULA I, dicrotophos (243)+COMPOUND OF FORMULA I, dicyclanil (244)+COMPOUND OF FORMULA I, dieldrin (1070)+COMPOUND OF FORMULA I, diethyl 5-methylpyrazol-3-yl phosphate (IUPAC name) (1076)+COMPOUND OF FORMULA I, diflubenzuron (250)+COMPOUND OF FORMULA I, dilor (alternative name) [CCN]+COMPOUND OF FORMULA I, dimefluthrin [CCN]+COMPOUND OF FORMULA I, dimefox (1081)+COMPOUND OF FORMULA I, dimetan (1085)+COMPOUND OF FORMULA I, dimethoate (262)+COMPOUND OF FORMULA I, dimethrin (1083)+COMPOUND OF FORMULA I, dimethylvinphos (265)+COMPOUND OF FORMULA I, dimetilan (1086)+COMPOUND OF FORMULA I, dinex (1089)+COMPOUND OF FORMULA I, dinex-diclexine (1089)+COMPOUND OF FORMULA I, dinoprop (1093)+COMPOUND OF FORMULA I, dinosam (1094)+COMPOUND OF FORMULA I, dinoseb (1095)+COMPOUND OF FORMULA I, dinotefuran (271)+COMPOUND OF FORMULA I, diofenolan (1099)+COMPOUND OF FORMULA I, dioxabenzofos (1100)+COMPOUND OF FORMULA I, dioxacarb (1101)+COMPOUND OF FORMULA I, dioxathion (1102)+COMPOUND OF FORMULA I, disulfoton (278)+COMPOUND OF FORMULA I, dithicrofos (1108)+COMPOUND OF FORMULA I, DNOC (282)+COMPOUND OF FORMULA I, doramectin (alternative name) [CCN]+COMPOUND OF FORMULA I, DSP (1115)+COMPOUND OF FORMULA I, ecdysterone (alternative name) [CCN]+COMPOUND OF FORMULA I, EI 1642 (development code) (1118)+COMPOUND OF FORMULA I, emamectin (291)+COMPOUND OF FORMULA I, emamectin benzoate (291)+COMPOUND OF FORMULA I, EMPC (1120)+COMPOUND OF FORMULA I, empenthrin (292)+COMPOUND OF FORMULA I, endosulfan (294)+COMPOUND OF FORMULA I, endothion (1121)+COMPOUND OF FORMULA I, endrin (1122)+COMPOUND OF FORMULA I, EPBP (1123)+COMPOUND OF FORMULA I, EPN (297)+COMPOUND OF FORMULA I, epofenonane (1124)+COMPOUND OF FORMULA I, eprinomectin (alternative name) [CCN]+COMPOUND OF FORMULA I, esfenvalerate (302)+COMPOUND OF FORMULA I, etaphos (alternative name) [CCN]+COMPOUND OF FORMULA I, ethiofencarb (308)+COMPOUND OF FORMULA I, ethion (309)+COMPOUND OF FORMULA I, ethiprole (310)+COMPOUND OF FORMULA I, ethoate-methyl (1134)+COMPOUND OF FORMULA I, ethoprophos (312)+COMPOUND OF FORMULA I, ethyl formate (IUPAC name) [CCN]+COMPOUND OF FORMULA I, ethyl-DDD (alternative name) (1056)+COMPOUND OF FORMULA I, ethylene dibromide (316)+COMPOUND OF FORMULA I, ethylene dichloride (chemical name) (1136)+COMPOUND OF FORMULA I, ethylene oxide [CCN]+COMPOUND OF FORMULA I, etofenprox (319)+COMPOUND OF FORMULA I, etrimfos (1142)+COMPOUND OF FORMULA I, EXD (1143)+COMPOUND OF FORMULA I, famphur (323)+COMPOUND OF FORMULA I, fenamiphos (326)+COMPOUND OF FORMULA I, fenazaflor (1147)+COMPOUND OF FORMULA I, fenchlorphos (1148)+COMPOUND OF FORMULA I, fenethacarb (1149)+COMPOUND OF FORMULA I, fenfluthrin (1150)+COMPOUND OF FORMULA I, fenitrothion (335)+COMPOUND OF FORMULA I, fenobucarb (336)+COMPOUND OF FORMULA I, fenoxacrim (1153)+COMPOUND OF FORMULA I, fenoxycarb (340)+COMPOUND OF FORMULA I, fenpirithrin (1155)+COMPOUND OF FORMULA I, fenpropathrin (342)+COMPOUND OF FORMULA I, fenpyrad (alternative name)+COMPOUND OF FORMULA I, fensulfothion (1158)+COMPOUND OF FORMULA I, fenthion (346)+COMPOUND OF FORMULA I, fenthion-ethyl [CCN]+COMPOUND OF FORMULA I, fenvalerate (349)+COMPOUND OF FORMULA I, fipronil (354)+COMPOUND OF FORMULA I, flonicamid (358)+COMPOUND OF FORMULA I, flubendiamide (CAS. Reg. No.: 272451-65-7)+COMPOUND OF FORMULA I, flucofuron (1168)+COMPOUND OF FORMULA I, flucycloxuron (366)+COMPOUND OF FORMULA I, flucythrinate (367)+COMPOUND OF FORMULA I, fluenetil (1169)+COMPOUND OF FORMULA I, flufenerim [CCN]+COMPOUND OF FORMULA I, flufenoxuron (370)+COMPOUND OF FORMULA I, flufenprox (1171)+COMPOUND OF FORMULA I, flumethrin (372)+COMPOUND OF FORMULA I, fluvalinate (1184)+COMPOUND OF FORMULA I, FMC 1137 (development code) (1185)+COMPOUND OF FORMULA I, fonofos (1191)+COMPOUND OF FORMULA I, formetanate (405)+COMPOUND OF FORMULA I, formetanate hydrochloride (405)+COMPOUND OF FORMULA I, formothion (1192)+COMPOUND OF FORMULA I, formparanate (1193)+COMPOUND OF FORMULA I, fosmethilan (1194)+COMPOUND OF FORMULA I, fospirate (1195)+COMPOUND OF FORMULA I, fosthiazate (408)+COMPOUND OF FORMULA I, fosthietan (1196)+COMPOUND OF FORMULA I, furathiocarb (412)+COMPOUND OF FORMULA I, furethrin (1200)+COMPOUND OF FORMULA I, gamma-cyhalothrin (197)+COMPOUND OF FORMULA I, gamma-HCH (430)+COMPOUND OF FORMULA I, guazatine (422)+COMPOUND OF FORMULA I, guazatine acetates (422)+COMPOUND OF FORMULA I, GY-81 (development code) (423)+COMPOUND OF FORMULA I, halfenprox (424)+COMPOUND OF FORMULA I, halofenozide (425)+COMPOUND OF FORMULA I, HCH (430)+COMPOUND OF FORMULA I, HEOD (1070)+COMPOUND OF FORMULA I, heptachlor (1211)+COMPOUND OF FORMULA I, heptenophos (432)+COMPOUND OF FORMULA I, heterophos [CCN]+COMPOUND OF FORMULA I, hexaflumuron (439)+COMPOUND OF FORMULA I, HHDN (864)+COMPOUND OF FORMULA I, hydramethylnon (443)+COMPOUND OF FORMULA I, hydrogen cyanide (444)+COMPOUND OF FORMULA I, hydroprene (445)+COMPOUND OF FORMULA I, hyquincarb (1223)+COMPOUND OF FORMULA I, imidacloprid (458)+COMPOUND OF FORMULA I, imiprothrin (460)+COMPOUND OF FORMULA I, indoxacarb (465)+COMPOUND OF FORMULA I, iodomethane (IUPAC name) (542)+COMPOUND OF FORMULA I, IPSP (1229)+COMPOUND OF FORMULA I, isazofos (1231)+COMPOUND OF FORMULA I, isobenzan (1232)+COMPOUND OF FORMULA I, isocarbophos (alternative name) (473)+COMPOUND OF FORMULA I, isodrin (1235)+COMPOUND OF FORMULA I, isofenphos (1236)+COMPOUND OF FORMULA I, isolane (1237)+COMPOUND OF FORMULA I, isoprocarb (472)+COMPOUND OF FORMULA I, isopropyl O-(methoxy-aminothiophosphoryl) salicylate (IUPAC name) (473)+COMPOUND OF FORMULA I, isoprothiolane (474)+COMPOUND OF FORMULA I, isothioate (1244)+COMPOUND OF FORMULA I, isoxathion (480)+COMPOUND OF FORMULA I, ivermectin (alternative name) [CCN]+COMPOUND OF FORMULA I, jasmolin I (696)+COMPOUND OF FORMULA I, jasmolin II (696)+COMPOUND OF FORMULA I, jodfenphos (1248)+COMPOUND OF FORMULA I, juvenile hormone I (alternative name) [CCN]+COMPOUND OF FORMULA I, juvenile hormone II (alternative name) [CCN]+COMPOUND OF FORMULA I, juvenile hormone III (alternative name) [CCN]+COMPOUND OF FORMULA I, kelevan (1249)+COMPOUND OF FORMULA I, kinoprene (484)+COMPOUND OF FORMULA I, lambda-cyhalothrin (198)+COMPOUND OF FORMULA I, lead arsenate [CCN]+COMPOUND OF FORMULA I, lepimectin (CCN)+COMPOUND OF FORMULA I, leptophos (1250)+COMPOUND OF FORMULA I, lindane (430)+COMPOUND OF FORMULA I, lirimfos (1251)+COMPOUND OF FORMULA I, lufenuron (490)+COMPOUND OF FORMULA I, lythidathion (1253)+COMPOUND OF FORMULA I, m-cumenyl methylcarbamate (IUPAC name) (1014)+COMPOUND OF FORMULA I, magnesium phosphide (IUPAC name) (640)+COMPOUND OF FORMULA I, malathion (492)+COMPOUND OF FORMULA I, malonoben (1254)+COMPOUND OF FORMULA I, mazidox (1255)+COMPOUND OF FORMULA I, mecarbam (502)+COMPOUND OF FORMULA I, mecarphon (1258)+COMPOUND OF FORMULA I, menazon (1260)+COMPOUND OF FORMULA I, mephosfolan (1261)+COMPOUND OF FORMULA I, mercurous chloride (513)+COMPOUND OF FORMULA I, mesulfenfos (1263)+COMPOUND OF FORMULA I, metaflumizone (CCN)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methacrifos (1266)+COMPOUND OF FORMULA I, methamidophos (527)+COMPOUND OF FORMULA I, methanesulfonyl fluoride (IUPAC/Chemical Abstracts name) (1268)+COMPOUND OF FORMULA I, methidathion (529)+COMPOUND OF FORMULA I, methiocarb (530)+COMPOUND OF FORMULA I, methocrotophos (1273)+COMPOUND OF FORMULA I, methomyl (531)+COMPOUND OF FORMULA I, methoprene (532)+COMPOUND OF FORMULA I, methoquin-butyl (1276)+COMPOUND OF FORMULA I, methothrin (alternative name) (533)+COMPOUND OF FORMULA I, methoxychlor (534)+COMPOUND OF FORMULA I, methoxyfenozide (535)+COMPOUND OF FORMULA I, methyl bromide (537)+COMPOUND OF FORMULA I, methyl isothiocyanate (543)+COMPOUND OF FORMULA I, methylchloroform (alternative name) [CCN]+COMPOUND OF FORMULA I, methylene chloride [CCN]+COMPOUND OF FORMULA I, metofluthrin [CCN]+COMPOUND OF FORMULA I, metolcarb (550)+COMPOUND OF FORMULA I, metoxadiazone (1288)+COMPOUND OF FORMULA I, mevinphos (556)+COMPOUND OF FORMULA I, mexacarbate (1290)+COMPOUND OF FORMULA I, milbemectin (557)+COMPOUND OF FORMULA I, milbemycin oxime (alternative name) [CCN]+COMPOUND OF FORMULA I, mipafox (1293)+COMPOUND OF FORMULA I, mirex (1294)+COMPOUND OF FORMULA I, monocrotophos (561)+COMPOUND OF FORMULA I, morphothion (1300)+COMPOUND OF FORMULA I, moxidectin (alternative name) [CCN]+COMPOUND OF FORMULA I, naftalofos (alternative name) [CCN]+COMPOUND OF FORMULA I, naled (567)+COMPOUND OF FORMULA I, naphthalene (IUPAC/Chemical Abstracts name) (1303)+COMPOUND OF FORMULA I, NC-170 (development code) (1306)+COMPOUND OF FORMULA I, NC-184 (compound code)+COMPOUND OF FORMULA I, nicotine (578)+COMPOUND OF FORMULA I, nicotine sulfate (578)+COMPOUND OF FORMULA I, nifluridide (1309)+COMPOUND OF FORMULA I, nitenpyram (579)+COMPOUND OF FORMULA I, nithiazine (1311)+COMPOUND OF FORMULA I, nitrilacarb (1313)+COMPOUND OF FORMULA I, nitrilacarb 1:1 zinc chloride complex (1313)+COMPOUND OF FORMULA I, NNI-0101 (compound code)+COMPOUND OF FORMULA I, NNI-0250 (compound code)+COMPOUND OF FORMULA I, nornicotine (traditional name) (1319)+COMPOUND OF FORMULA I, novaluron (585)+COMPOUND OF FORMULA I, noviflumuron (586)+COMPOUND OF FORMULA I, O-5-dichloro-4-iodophenyl O-ethyl ethylphosphonothioate (IUPAC name) (1057)+COMPOUND OF FORMULA I, O,O-diethyl O-4-methyl-2-oxo-2H-chromen-7-yl phosphorothioate (IUPAC name) (1074)+COMPOUND OF FORMULA I, O,O-diethyl O-6-methyl-2-propylpyrimidin-4-yl phosphorothioate (IUPAC name) (1075)+COMPOUND OF FORMULA I, O,O,O',O'-tetrapropyl dithiopyrophosphate (IUPAC name) (1424)+COMPOUND OF FORMULA I, oleic acid (IUPAC name) (593)+COMPOUND OF FORMULA I, omethoate (594)+COMPOUND OF FORMULA I, oxamyl (602)+COMPOUND OF FORMULA I, oxydemeton-methyl (609)+COMPOUND OF FORMULA I, oxydeprofos (1324)+COMPOUND OF FORMULA I, oxydisulfoton (1325)+COMPOUND OF FORMULA I, pp'-DDT (219)+COMPOUND OF FORMULA I, para-dichlorobenzene [CCN]+COMPOUND OF FORMULA I, parathion (615)+COMPOUND OF FORMULA I, parathion-methyl (616)+COMPOUND OF FORMULA I, penfluoron (alternative name) [CCN]+COMPOUND OF FORMULA I, pentachlorophenol (623)+COMPOUND OF FORMULA I, pentachlorophenyl laurate (IUPAC name) (623)+COMPOUND OF FORMULA I, permethrin (626)+COMPOUND OF FORMULA I, petroleum oils (alternative name) (628)+COMPOUND OF FORMULA I, PH 60-38 (development code) (1328)+COMPOUND OF FORMULA I, phenkapton (1330)+COMPOUND OF FORMULA I, phenothrin (630)+COMPOUND OF FORMULA I, phenthoate (631)+COMPOUND OF FORMULA I, phorate (636)+COMPOUND OF FORMULA I, phosalone (637)+COMPOUND OF FORMULA I, phosfolan (1338)+COMPOUND OF FORMULA I, phosmet (638)+COMPOUND OF FORMULA I, phosnichlor (1339)+COMPOUND OF FORMULA I, phosphamidon (639)+COMPOUND OF FORMULA I, phosphine (IUPAC name) (640)+COMPOUND OF FORMULA I, phoxim (642)+COMPOUND OF FORMULA I, phoxim-methyl (1340)+COMPOUND OF FORMULA I, pirimetaphos (1344)+COMPOUND OF FORMULA I, pirimicarb (651)+COMPOUND OF FORMULA I, pirimiphos-ethyl (1345)+COMPOUND OF FORMULA I, pirimiphos-methyl (652)+COMPOUND OF FORMULA I, polychlorodicyclopentadiene isomers (IUPAC name) (1346)+COMPOUND OF FORMULA I, polychloroterpenes (traditional name) (1347)+COMPOUND OF FORMULA I, potassium arsenite [CCN]+COMPOUND OF FORMULA I, potassium thiocyanate [CCN]+COMPOUND OF FORMULA I, prallethrin (655)+COMPOUND OF FORMULA I, precocene I (alternative name) [CCN]+COMPOUND OF FORMULA I, precocene II (alternative name) [CCN]+COMPOUND OF FORMULA I, precocene III (alternative name) [CCN]+COMPOUND OF FORMULA I, primidophos (1349)+COMPOUND OF FORMULA I, profenofos (662)+COMPOUND OF FORMULA I, profluthrin [CCN]+COMPOUND OF FORMULA I, promacyl (1354)+COMPOUND OF FORMULA I, promecarb (1355)+COMPOUND OF FORMULA I, propaphos (1356)+COMPOUND OF FORMULA I, propetamphos (673)+COMPOUND OF FORMULA I, propoxur (678)+COMPOUND OF FORMULA I, prothidathion (1360)+COMPOUND OF FORMULA I, prothiofos (686)+COMPOUND OF FORMULA I, prothoate (1362)+

COMPOUND OF FORMULA I, protrifenbute [CCN]+COMPOUND OF FORMULA I, pymetrozine (688)+COMPOUND OF FORMULA I, pyraclofos (689)+COMPOUND OF FORMULA I, pyrafluprole [CCN]+COMPOUND OF FORMULA I, pyrazophos (693)+COMPOUND OF FORMULA I, pyresmethrin (1367)+COMPOUND OF FORMULA I, pyrethrin I (696)+COMPOUND OF FORMULA I, pyrethrin II (696)+COMPOUND OF FORMULA I, pyrethrins (696)+COMPOUND OF FORMULA I, pyridaben (699)+COMPOUND OF FORMULA I, pyridalyl (700)+COMPOUND OF FORMULA I, pyridaphenthion (701)+COMPOUND OF FORMULA I, pyrifluquinazon [CCN]+COMPOUND OF FORMULA I, pyrimidifen (706)+COMPOUND OF FORMULA I, pyrimitate (1370)+COMPOUND OF FORMULA I, pyriprole [CCN]+COMPOUND OF FORMULA I, pyriproxyfen (708)+COMPOUND OF FORMULA I, quassia (alternative name) [CCN]+COMPOUND OF FORMULA I, quinalphos (711)+COMPOUND OF FORMULA I, quinalphos-methyl (1376)+COMPOUND OF FORMULA I, quinothion (1380)+COMPOUND OF FORMULA I, quintiofos (1381)+COMPOUND OF FORMULA I, R-1492 (development code) (1382)+COMPOUND OF FORMULA I, rafoxanide (alternative name) [CCN]+COMPOUND OF FORMULA I, resmethrin (719)+COMPOUND OF FORMULA I, rotenone (722)+COMPOUND OF FORMULA I, RU 15525 (development code) (723)+COMPOUND OF FORMULA I, RU 25475 (development code) (1386)+COMPOUND OF FORMULA I, ryania (alternative name) (1387)+COMPOUND OF FORMULA I, ryanodine (traditional name) (1387)+COMPOUND OF FORMULA I, sabadilla (alternative name) (725)+COMPOUND OF FORMULA I, schradan (1389)+COMPOUND OF FORMULA I, sebufos (alternative name)+COMPOUND OF FORMULA I, selamectin (alternative name) [CCN]+COMPOUND OF FORMULA I, SI-0009 (compound code)+COMPOUND OF FORMULA I, SI-0205 (compound code)+COMPOUND OF FORMULA I, SI-0404 (compound code)+COMPOUND OF FORMULA I, SI-0405 (compound code)+COMPOUND OF FORMULA I, silafluofen (728)+COMPOUND OF FORMULA I, SN 72129 (development code) (1397)+COMPOUND OF FORMULA I, sodium arsenite [CCN]+COMPOUND OF FORMULA I, sodium cyanide (444)+COMPOUND OF FORMULA I, sodium fluoride (IUPAC/Chemical Abstracts name) (1399)+COMPOUND OF FORMULA I, sodium hexafluorosilicate (1400)+COMPOUND OF FORMULA I, sodium pentachlorophenoxide (623)+COMPOUND OF FORMULA I, sodium selenate (IUPAC name) (1401)+COMPOUND OF FORMULA I, sodium thiocyanate [CCN]+COMPOUND OF FORMULA I, sophamide (1402)+COMPOUND OF FORMULA I, spinetoram [CCN]+COMPOUND OF FORMULA I, spinosad (737)+COMPOUND OF FORMULA I, spiromesifen (739)+COMPOUND OF FORMULA I, spirotetramat [CCN]+COMPOUND OF FORMULA I, sulcofuron (746)+COMPOUND OF FORMULA I, sulcofuron-sodium (746)+COMPOUND OF FORMULA I, sulfluramid (750)+COMPOUND OF FORMULA I, sulfotep (753)+COMPOUND OF FORMULA I, sulfoxaflor [CCN]+COMPOUND OF FORMULA I, sulfuryl fluoride (756)+COMPOUND OF FORMULA I, sulprofos (1408)+COMPOUND OF FORMULA I, tar oils (alternative name) (758)+COMPOUND OF FORMULA I, tau-fluvalinate (398)+COMPOUND OF FORMULA I, tazimcarb (1412)+COMPOUND OF FORMULA I, TDE (1414)+COMPOUND OF FORMULA I, tebufenozide (762)+COMPOUND OF FORMULA I, tebufenpyrad (763)+COMPOUND OF FORMULA I, tebupirimfos (764)+COMPOUND OF FORMULA I, teflubenzuron (768)+COMPOUND OF FORMULA I, tefluthrin (769)+COMPOUND OF FORMULA I, temephos (770)+COMPOUND OF FORMULA I, TEPP (1417)+COMPOUND OF FORMULA I, terallethrin (1418)+COMPOUND OF FORMULA I, terbam (alternative name)+COMPOUND OF FORMULA I, terbufos (773)+COMPOUND OF FORMULA I, tetrachloroethane [CCN]+COMPOUND OF FORMULA I, tetrachlorvinphos (777)+COMPOUND OF FORMULA I, tetramethrin (787)+COMPOUND OF FORMULA I, tetramethylfluthrin (CAS. Reg. No.: 84937-88-2)+COMPOUND OF FORMULA I, theta-cypermethrin (204)+COMPOUND OF FORMULA I, thiacloprid (791)+COMPOUND OF FORMULA I, thiafenox (alternative name)+COMPOUND OF FORMULA I, thiamethoxam (792)+COMPOUND OF FORMULA I, thicrofos (1428)+COMPOUND OF FORMULA I, thiocarboxime (1431)+COMPOUND OF FORMULA I, thiocyclam (798)+COMPOUND OF FORMULA I, thiocyclam hydrogen oxalate (798)+COMPOUND OF FORMULA I, thiodicarb (799)+COMPOUND OF FORMULA I, thiofanox (800)+COMPOUND OF FORMULA I, thiometon (801)+COMPOUND OF FORMULA I, thionazin (1434)+COMPOUND OF FORMULA I, thiosultap (803)+COMPOUND OF FORMULA I, thiosultap-sodium (803)+COMPOUND OF FORMULA I, thuringiensin (alternative name) [CCN]+COMPOUND OF FORMULA I, tolfenpyrad (809)+COMPOUND OF FORMULA I, tralomethrin (812)+COMPOUND OF FORMULA I, transfluthrin (813)+COMPOUND OF FORMULA I, transpermethrin (1440)+COMPOUND OF FORMULA I, triamiphos (1441)+COMPOUND OF FORMULA I, triazamate (818)+COMPOUND OF FORMULA I, triazophos (820)+COMPOUND OF FORMULA I, triazuron (alternative name)+COMPOUND OF FORMULA I, trichlorfon (824)+COMPOUND OF FORMULA I, trichlormetaphos-3 (alternative name) [CCN]+COMPOUND OF FORMULA I, trichloronat (1452)+COMPOUND OF FORMULA I, trifenofos (1455)+COMPOUND OF FORMULA I, triflumuron (835)+COMPOUND OF FORMULA I, trimethacarb (840)+COMPOUND OF FORMULA I, triprene (1459)+COMPOUND OF FORMULA I, vamidothion (847)+COMPOUND OF FORMULA I, vaniliprole [CCN]+COMPOUND OF FORMULA I, veratridine (alternative name) (725)+COMPOUND OF FORMULA I, veratrine (alternative name) (725)+COMPOUND OF FORMULA I, XMC (853)+COMPOUND OF FORMULA I, xylylcarb (854)+COMPOUND OF FORMULA I, YI-5302 (compound code)+COMPOUND OF FORMULA I, zeta-cypermethrin (205)+COMPOUND OF FORMULA I, zetamethrin (alternative name)+COMPOUND OF FORMULA I, zinc phosphide (640)+COMPOUND OF FORMULA I, zolaprofos (1469) and ZXI 8901 (development code) (858)+COMPOUND OF FORMULA I, a molluscicide selected from the group of substances consisting of bis(tributyltin) oxide (IUPAC name) (913)+COMPOUND OF FORMULA I, bromoacetamide [CCN]+COMPOUND OF FORMULA I, calcium arsenate [CCN]+COMPOUND OF FORMULA I, cloethocarb (999)+COMPOUND OF FORMULA I, copper acetoarsenite [CCN]+COMPOUND OF FORMULA I, copper sulfate (172)+COMPOUND OF FORMULA I, fentin (347)+COMPOUND OF FORMULA I, ferric phosphate (IUPAC name) (352)+COMPOUND OF FORMULA I, metaldehyde (518)+COMPOUND OF FORMULA I, methiocarb (530)+COMPOUND OF FORMULA I, niclosamide (576)+COMPOUND OF FORMULA I, niclosamide-olamine (576)+COMPOUND OF FORMULA I, pentachlorophenol (623)+

COMPOUND OF FORMULA I, sodium pentachlorophenoxide (623)+COMPOUND OF FORMULA I, tazimcarb (1412)+COMPOUND OF FORMULA I, thiodicarb (799)+COMPOUND OF FORMULA I, tralopyril [CCN]+COMPOUND OF FORMULA I, tributyltin oxide (913)+COMPOUND OF FORMULA I, trifenmorph (1454)+COMPOUND OF FORMULA I, trimethacarb (840)+COMPOUND OF FORMULA I, triphenyltin acetate (IUPAC name) (347) and triphenyltin hydroxide (IUPAC name) (347)+COMPOUND OF FORMULA I, a nematicide selected from the group of substances consisting of AKD-3088 (compound code)+COMPOUND OF FORMULA I, 1,2-dibromo-3-chloropropane (IUPAC/Chemical Abstracts name) (1045)+COMPOUND OF FORMULA I, 1,2-dichloropropane (IUPAC/Chemical Abstracts name) (1062)+COMPOUND OF FORMULA I, 1,2-dichloropropane with 1,3-dichloropropene (IUPAC name) (1063)+COMPOUND OF FORMULA I, 1,3-dichloropropene (233)+COMPOUND OF FORMULA 1,3,4-dichlorotetrahydrothiophene 1,1-dioxide (IUPAC/Chemical Abstracts name) (1065)+COMPOUND OF FORMULA I, 3-(4-chlorophenyl)-5-methylrhodanine (IUPAC name) (980)+COMPOUND OF FORMULA 1,5-methyl-6-thioxo-1,3,5-thiadiazinan-3-ylacetic acid (IUPAC name) (1286)+COMPOUND OF FORMULA I, 6-isopentenylaminopurine (alternative name) (210)+COMPOUND OF FORMULA I, abamectin (1)+COMPOUND OF FORMULA I, acetoprole [CCN]+COMPOUND OF FORMULA I, alanycarb (15)+COMPOUND OF FORMULA I, aldicarb (16)+COMPOUND OF FORMULA I, aldoxycarb (863)+COMPOUND OF FORMULA I, AZ 60541 (compound code)+COMPOUND OF FORMULA I, benclothiaz [CCN]+COMPOUND OF FORMULA I, benomyl (62)+COMPOUND OF FORMULA I, butylpyridaben (alternative name)+COMPOUND OF FORMULA I, cadusafos (109)+COMPOUND OF FORMULA I, carbofuran (118)+COMPOUND OF FORMULA I, carbon disulfide (945)+COMPOUND OF FORMULA I, carbosulfan (119)+COMPOUND OF FORMULA I, chloropicrin (141)+COMPOUND OF FORMULA I, chlorpyrifos (145)+COMPOUND OF FORMULA I, cloethocarb (999)+COMPOUND OF FORMULA I, cytokinins (alternative name) (210)+COMPOUND OF FORMULA I, dazomet (216)+COMPOUND OF FORMULA I, DBCP (1045)+COMPOUND OF FORMULA I, DCIP (218)+COMPOUND OF FORMULA I, diamidafos (1044)+COMPOUND OF FORMULA I, dichlofenthion (1051)+COMPOUND OF FORMULA I, dicliphos (alternative name)+COMPOUND OF FORMULA I, dimethoate (262)+COMPOUND OF FORMULA I, doramectin (alternative name) [CCN]+COMPOUND OF FORMULA I, emamectin (291)+COMPOUND OF FORMULA I, emamectin benzoate (291)+COMPOUND OF FORMULA I, eprinomectin (alternative name) [CCN]+COMPOUND OF FORMULA I, ethoprophos (312)+COMPOUND OF FORMULA I, ethylene dibromide (316)+COMPOUND OF FORMULA I, fenamiphos (326)+COMPOUND OF FORMULA I, fenpyrad (alternative name)+COMPOUND OF FORMULA I, fensulfothion (1158)+COMPOUND OF FORMULA I, fluensulfone (CAS. Reg. No.: 318290-98-1)+COMPOUND OF FORMULA I, fosthiazate (408)+COMPOUND OF FORMULA I, fosthietan (1196)+COMPOUND OF FORMULA I, furfural (alternative name) [CCN]+COMPOUND OF FORMULA I, GY-81 (development code) (423)+COMPOUND OF FORMULA I, heterophos [CCN]+COMPOUND OF FORMULA I, imicyafos [CCN]+COMPOUND OF FORMULA I, iodomethane (IUPAC name) (542)+COMPOUND OF FORMULA I, isamidofos (1230)+COMPOUND OF FORMULA I, isazofos (1231)+COMPOUND OF FORMULA I, ivermectin (alternative name) [CCN]+COMPOUND OF FORMULA I, kinetin (alternative name) (210)+COMPOUND OF FORMULA I, mecarphon (1258)+COMPOUND OF FORMULA I, metam (519)+COMPOUND OF FORMULA I, metam-potassium (alternative name) (519)+COMPOUND OF FORMULA I, metam-sodium (519)+COMPOUND OF FORMULA I, methyl bromide (537)+COMPOUND OF FORMULA I, methyl isothiocyanate (543)+COMPOUND OF FORMULA I, milbemycin oxime (alternative name) [CCN]+COMPOUND OF FORMULA I, moxidectin (alternative name) [CCN]+COMPOUND OF FORMULA I, *Myrothecium verrucaria* composition (alternative name) (565)+COMPOUND OF FORMULA I, NC-184 (compound code)+COMPOUND OF FORMULA I, oxamyl (602)+COMPOUND OF FORMULA I, phorate (636)+COMPOUND OF FORMULA I, phosphamidon (639)+COMPOUND OF FORMULA I, phosphocarb [CCN]+COMPOUND OF FORMULA I, sebufos (alternative name)+COMPOUND OF FORMULA I, selamectin (alternative name) [CCN]+COMPOUND OF FORMULA I, spinosad (737)+COMPOUND OF FORMULA I, terbam (alternative name)+COMPOUND OF FORMULA I, terbufos (773)+COMPOUND OF FORMULA I, tetrachlorothiophene (IUPAC/Chemical Abstracts name) (1422)+COMPOUND OF FORMULA I, thiafenox (alternative name)+COMPOUND OF FORMULA I, thionazin (1434)+COMPOUND OF FORMULA I, triazophos (820)+COMPOUND OF FORMULA I, triazuron (alternative name)+COMPOUND OF FORMULA I, xylenols [CCN]+COMPOUND OF FORMULA I, YI-5302 (compound code) and zeatin (alternative name) (210)+COMPOUND OF FORMULA I, a nitrification inhibitor selected from the group of substances consisting of potassium ethylxanthate [CCN] and nitrapyrin (580)+COMPOUND OF FORMULA I, a plant activator selected from the group of substances consisting of acibenzolar (6)+COMPOUND OF FORMULA I, acibenzolar-5-methyl (6)+COMPOUND OF FORMULA I, probenazole (658) and *Reynoutria sachalinensis* extract (alternative name) (720)+COMPOUND OF FORMULA I, a rodenticide selected from the group of substances consisting of 2-isovalerylindan-1,3-dione (IUPAC name) (1246)+COMPOUND OF FORMULA 1,4-(quinoxalin-2-ylamino)benzenesulfonamide (IUPAC name) (748)+COMPOUND OF FORMULA I, alpha-chlorohydrin [CCN]+COMPOUND OF FORMULA I, aluminium phosphide (640)+COMPOUND OF FORMULA I, antu (880)+COMPOUND OF FORMULA I, arsenous oxide (882)+COMPOUND OF FORMULA I, barium carbonate (891)+COMPOUND OF FORMULA I, bisthiosemi (912)+COMPOUND OF FORMULA I, brodifacoum (89)+COMPOUND OF FORMULA I, bromadiolone (91)+COMPOUND OF FORMULA I, bromethalin (92)+COMPOUND OF FORMULA I, calcium cyanide (444)+COMPOUND OF FORMULA I, chloralose (127)+COMPOUND OF FORMULA I, chlorophacinone (140)+COMPOUND OF FORMULA I, cholecalciferol (alternative name) (850)+COMPOUND OF FORMULA I, coumachlor (1004)+COMPOUND OF FORMULA I, coumafuryl (1005)+COMPOUND OF FORMULA I, coumatetralyl (175)+COMPOUND OF FORMULA I, crimidine (1009)+COMPOUND OF FORMULA I, difenacoum (246)+COMPOUND OF FORMULA I, difethialone (249)+COM- POUND OF FORMULA I, diphacinone (273)+COMPOUND OF FORMULA I, ergocalciferol (301)+COMPOUND OF FORMULA I, flocoumafen (357)+COMPOUND OF FORMULA I, fluoroacetamide (379)+COMPOUND OF FORMULA I, flupropadine (1183)+COMPOUND OF FORMULA I, flupropadine hydrochloride (1183)+COMPOUND OF FORMULA I, gamma-HCH (430)+COMPOUND OF FORMULA I, HCH (430)+COMPOUND OF FORMULA I, hydrogen cyanide (444)+COMPOUND OF FORMULA I, iodomethane (IUPAC name) (542)+COMPOUND OF FORMULA I, lindane (430)+COMPOUND OF FORMULA I, magnesium phosphide (IUPAC name) (640)+COMPOUND OF FORMULA I, methyl bromide (537)+COMPOUND OF FORMULA I, norbormide (1318)+COMPOUND OF FORMULA I, phosacetim (1336)+COMPOUND OF FORMULA I, phosphine (IUPAC name) (640)+COMPOUND OF FORMULA I, phosphorus [CCN]+COMPOUND OF FORMULA I, pindone (1341)+COMPOUND OF FORMULA I, potassium arsenite [CCN]+COMPOUND OF FORMULA I, pyrinuron (1371)+COMPOUND OF FORMULA I, scilliroside (1390)+COMPOUND OF FORMULA I, sodium arsenite [CCN]+COMPOUND OF FORMULA I, sodium cyanide (444)+COMPOUND OF FORMULA I, sodium fluoroacetate (735)+COMPOUND OF FORMULA I, strychnine (745)+COMPOUND OF FORMULA I, thallium sulfate [CCN]+COMPOUND OF FORMULA I, warfarin (851) and zinc phosphide (640)+COMPOUND OF FORMULA I, a synergist selected from the group of substances consisting of 2-(2-butoxyethoxy)ethyl piperonylate (IUPAC name) (934)+COMPOUND OF FORMULA I, 5-(1,3-benzodioxol-5-yl)-3-hexylcyclohex-2-enone (IUPAC name) (903)+COMPOUND OF FORMULA I, farnesol with nerolidol (alternative name) (324)+COMPOUND OF FORMULA I, MB-599 (development code) (498)+COMPOUND OF FORMULA I, MGK 264 (development code) (296)+COMPOUND OF FORMULA I, piperonyl butoxide (649)+COMPOUND OF FORMULA I, piprotal (1343)+COMPOUND OF FORMULA I, propyl isomer (1358)+COMPOUND OF FORMULA I, S421 (development code) (724)+COMPOUND OF FORMULA I, sesamex (1393)+COMPOUND OF FORMULA I, sesasmolin (1394) and sulfoxide (1406)+COMPOUND OF FORMULA I, an animal repellent selected from the group of substances consisting of anthraquinone (32)+COMPOUND OF FORMULA I, chloralose (127)+COMPOUND OF FORMULA I, copper naphthenate [CCN]+COMPOUND OF FORMULA I, copper oxychloride (171)+COMPOUND OF FORMULA I, diazinon (227)+COMPOUND OF FORMULA I, dicyclopentadiene (chemical name) (1069)+COMPOUND OF FORMULA I, guazatine (422)+COMPOUND OF FORMULA I, guazatine acetates (422)+COMPOUND OF FORMULA I, methiocarb (530)+COMPOUND OF FORMULA I, pyridin-4-amine (IUPAC name) (23)+COMPOUND OF FORMULA I, thiram (804)+COMPOUND OF FORMULA I, trimethacarb (840)+COMPOUND OF FORMULA I, zinc naphthenate [CCN] and ziram (856)+COMPOUND OF FORMULA I, a virucide selected from the group of substances consisting of imanin (alternative name) [CCN] and ribavirin (alternative name) [CCN]+COMPOUND OF FORMULA I, a wound protectant selected from the group of substances consisting of mercuric oxide (512)+COMPOUND OF FORMULA I, octhilinone (590) and thiophanate-methyl (802)+COMPOUND OF FORMULA I, an insecticide selected from the group consisting of the compound of the formula A-1

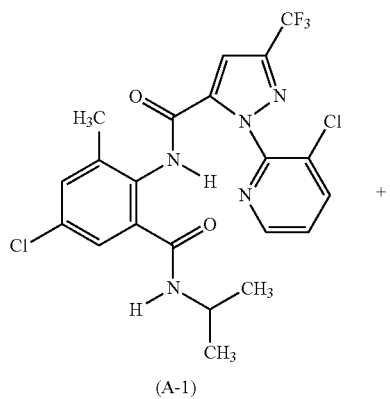

(A-1)

COMPOUND OF FORMULA I, the formula A-2

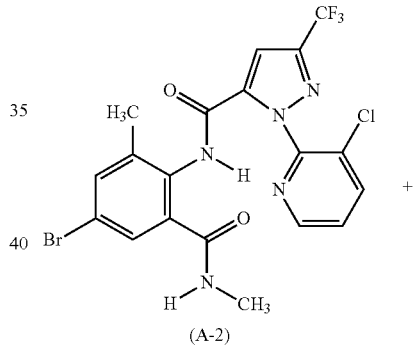

(A-2)

COMPOUND OF FORMULA I the formula A-3

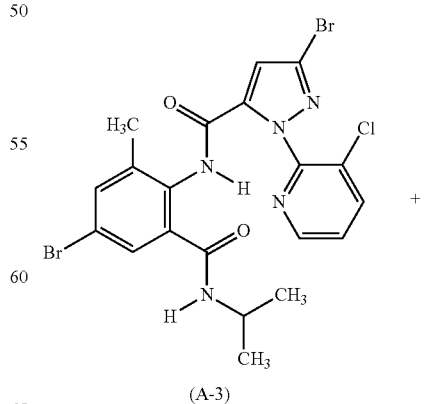

(A-3)

COMPOUND OF FORMULA I, the formula A-4
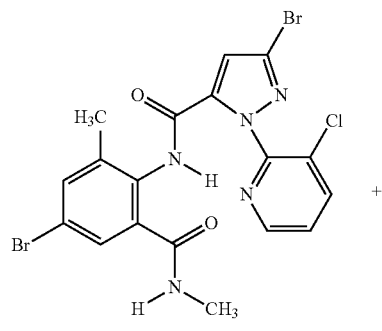
(A-4)
COMPOUND OF FORMULA I,
the formula A-5
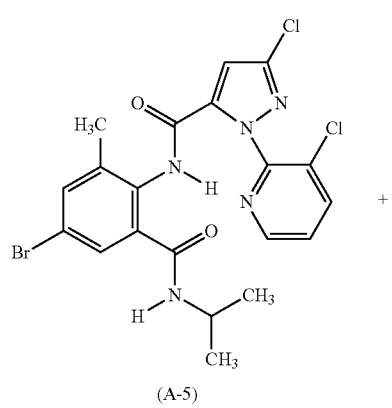
(A-5)
COMPOUND OF FORMULA I,
the formula A-6
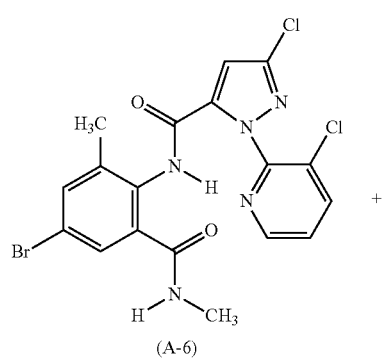
(A-6)
COMPOUND OF FORMULA I,
the formula A-7
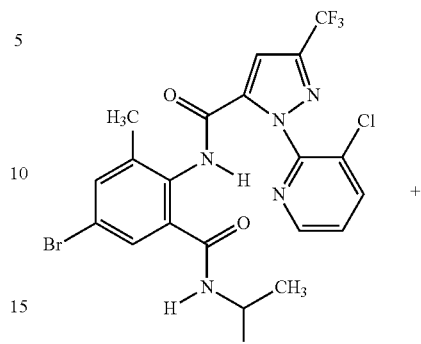
(A-7)
COMPOUND OF FORMULA I,
the formula A-8
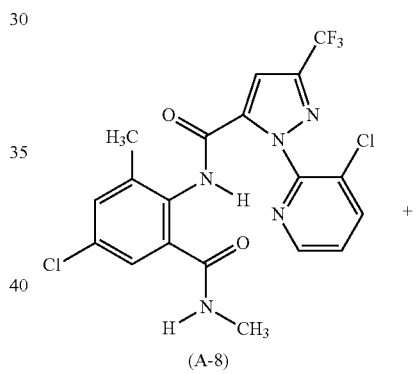
(A-8)
COMPOUND OF FORMULA I,
the formula A-9
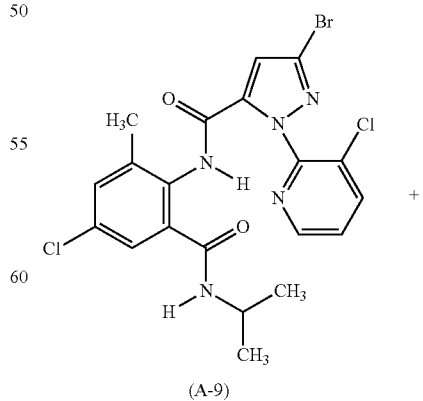
(A-9)
COMPOUND OF FORMULA I, the formula A-10
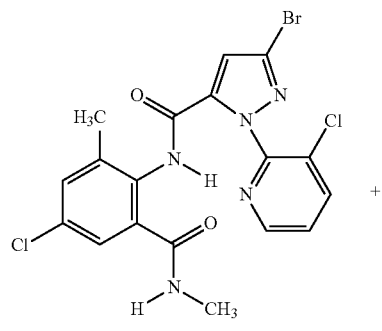
(A-10)
COMPOUND OF FORMULA I,
the formula A-11
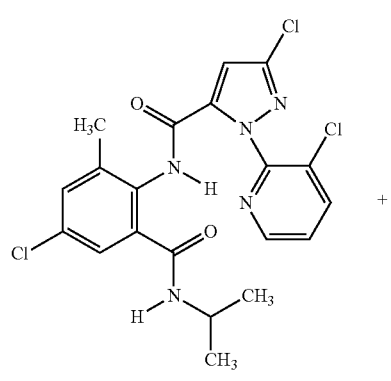
(A-11)
COMPOUND OF FORMULA I,
the formula A-12
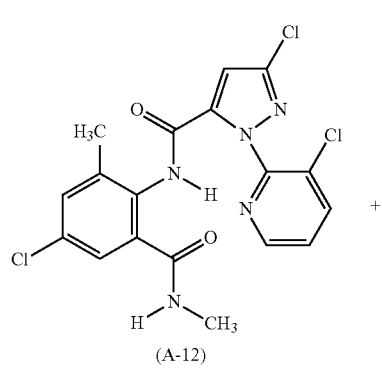
(A-12)
COMPOUND OF FORMULA I,
the formula A-13
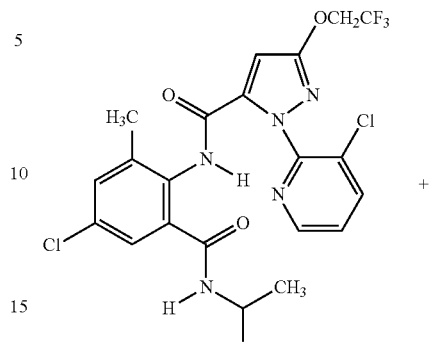
(A-13)
COMPOUND OF FORMULA I,
the formula A-14
(A-14)
COMPOUND OF FORMULA I,
the formula A-15
(A-15)
COMPOUND OF FORMULA I, the formula A-16
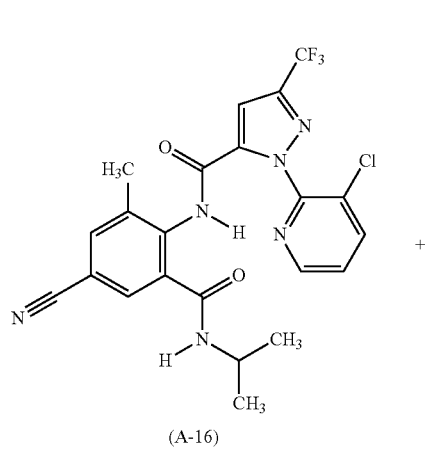
(A-16)
COMPOUND OF FORMULA I,
the formula A-17
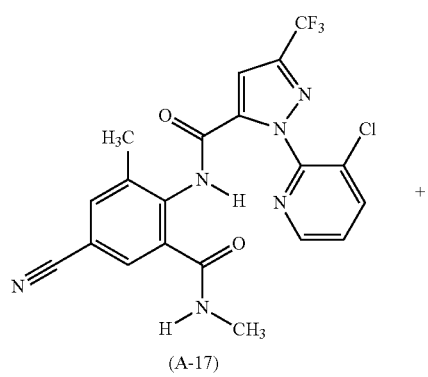
(A-17)
COMPOUND OF FORMULA I,
the formula A-18
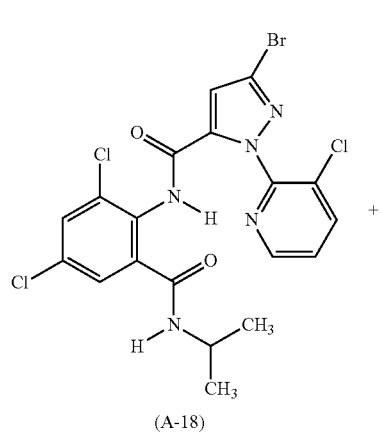
(A-18)
COMPOUND OF FORMULA I,
the formula A-19
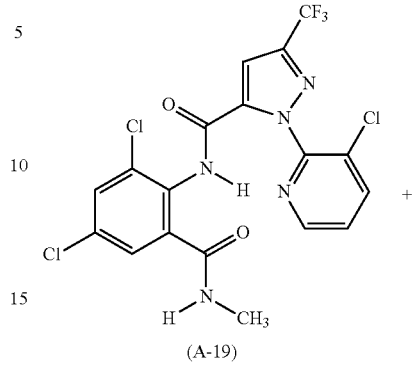
(A-19)
COMPOUND OF FORMULA I,
the formula A-20
(A-20)
COMPOUND OF FORMULA I,
the formula A-21
(A-21)
COMPOUND OF FORMULA I, the formula A-22

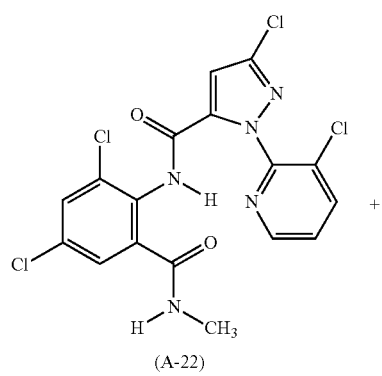

(A-22)

COMPOUND OF FORMULA I, the formula A-23

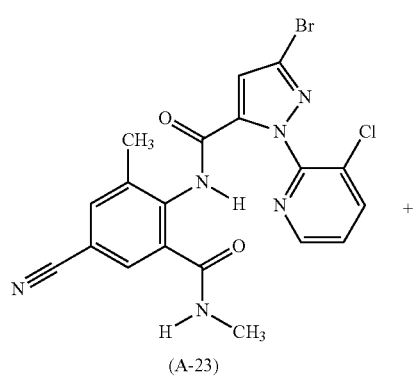

(A-23)

COMPOUND OF FORMULA I, the formula A-24

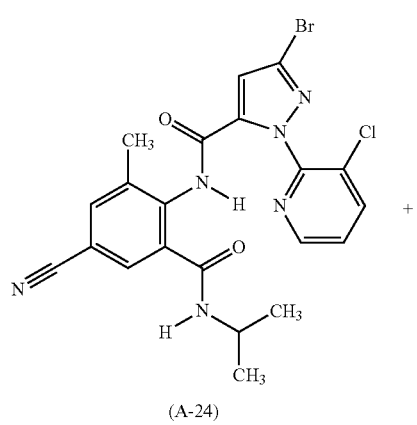

(A-24)

COMPOUND OF FORMULA I, the formula A-25

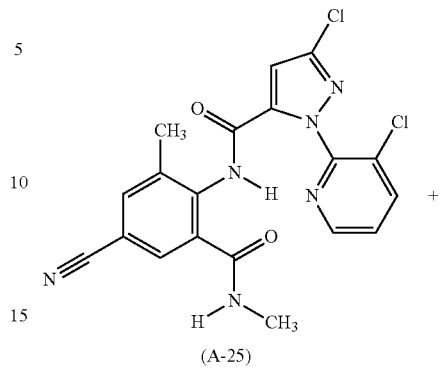

(A-25)

COMPOUND OF FORMULA I, the formula A-26

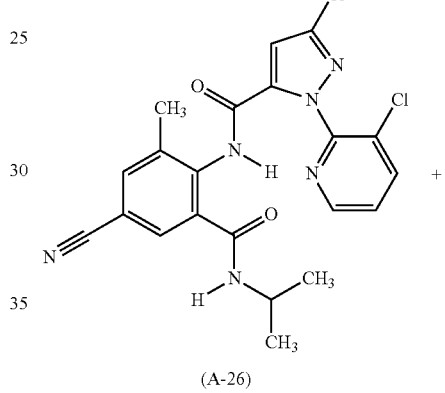

(A-26)

COMPOUND OF FORMULA I, and the formula A-27

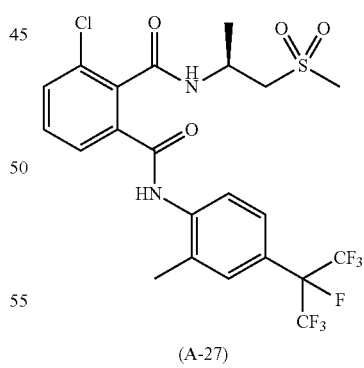

(A-27)

COMPOUND OF FORMULA I.

The references in brackets behind the active ingredients, e.g. [3878-19-1] refer to the Chemical Abstracts Registry number. The compounds of the formula A-1 to A-26 are described in WO 03/015518 or in WO 04/067528. The compound of the formula A-27 is described in WO 06/022225 and in WO 07/112,844. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; Compendium of Pesticide Common Names, Copyright© 1995-2004]; for example, the compound "acetoprole" is described under the internet address http://www.alanwood.net/pesticides/acetoprole.htmL.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The compounds of formula I according to the invention can also be used in combination with one or more fungicides. In particular, in the following mixtures of the compounds of formula I with fungicides, the term COMPOUND OF FORMULA I preferably refers to a compound selected from one of the Tables A, B or C:
COMPOUND OF FORMULA I+(E)-N-methyl-2-[2-(2,5-dimethylphenoxymethyl)phenyl]-2-methoxy-iminoacetamide (SSF-129), COMPOUND OF FORMULA I+4-bromo-2-cyano-N,N-dimethyl-6-trifluoromethylbenzimidazole-1-sulphonamide, COMPOUND OF FORMULA I+α-[N-(3-chloro-2,6-xylyl)-2-methoxyacetamido]-γ-butyrolactone, COMPOUND OF FORMULA I+4-chloro-2-cyano-N,N-dimethyl-5-p-tolylimidazole-1-sulfonamide (IKF-916, cyamidazosulfamid), COMPOUND OF FORMULA I+3-5-dichloro-N-(3-chloro-1-ethyl-1-methyl-2-oxopropyl)-4-methylbenzamide (RH-7281, zoxamide), COMPOUND OF FORMULA I+N-allyl-4,5,-dimethyl-2-trimethylsilylthiophene-3-carboxamide (MON65500), COMPOUND OF FORMULA I+N-(1-cyano-1,2-dimethylpropyl)-2-(2,4-dichlorophenoxy)propionamide (AC382042), COMPOUND OF FORMULA I+N-(2-methoxy-5-pyridyl)-cyclopropane carboxamide, COMPOUND OF FORMULA I+acibenzolar, COMPOUND OF FORMULA I+alanycarb, COMPOUND OF FORMULA I+aldimorph, COMPOUND OF FORMULA I+amisulbrom, COMPOUND OF FORMULA I+anilazine, COMPOUND OF FORMULA I+azaconazole, COMPOUND OF FORMULA I+azoxystrobin, COMPOUND OF FORMULA I+benalaxyl, COMPOUND OF FORMULA I+benalaxyl-M, COMPOUND OF FORMULA I+benomyl, COMPOUND OF FORMULA I+benthiavalicarb, COMPOUND OF FORMULA I+biloxazol, COMPOUND OF FORMULA I+bitertanol, COMPOUND OF FORMULA I+bixafen, COMPOUND OF FORMULA I+blasticidin S, COMPOUND OF FORMULA I+boscalid, COMPOUND OF FORMULA I+bromuconazole, COMPOUND OF FORMULA I+bupirimate, COMPOUND OF FORMULA I+captafol, COMPOUND OF FORMULA I+captan, COMPOUND OF FORMULA I+carbendazim, COMPOUND OF FORMULA I+carbendazim chlorhydrate, COMPOUND OF FORMULA I+carboxin, COMPOUND OF FORMULA I+carpropamid, carvone, COMPOUND OF FORMULA I+CGA41396, COMPOUND OF FORMULA I+CGA41397, COMPOUND OF FORMULA I+chinomethionate, COMPOUND OF FORMULA I+chlazafenone, COMPOUND OF FORMULA I+chlorothalonil, COMPOUND OF FORMULA I+chlorozolinate, COMPOUND OF FORMULA I+clozylacon, COMPOUND OF FORMULA I+copper containing compounds such as copper oxychloride, copper oxyquinolate, copper sulphate, copper tallate and Bordeaux mixture, COMPOUND OF FORMULA I+cyazofamid, COMPOUND OF FORMULA I+cyflufenamid, COMPOUND OF FORMULA I+cymoxanil, COMPOUND OF FORMULA I+cyproconazole, COMPOUND OF FORMULA I+cyprodinil, COMPOUND OF FORMULA I+debacarb, COMPOUND OF FORMULA I+di-2-pyridyl disulphide 1,1'-dioxide, COMPOUND OF FORMULA I+dichlofluanid, COMPOUND OF FORMULA I+diclomezine, COMPOUND OF FORMULA I+dicloran, COMPOUND OF FORMULA I+diethofencarb, COMPOUND OF FORMULA I+difenoconazole, COMPOUND OF FORMULA I+difenzoquat, COMPOUND OF FORMULA I+diflumetorim, COMPOUND OF FORMULA I+O,O-di-iso-propyl-5-benzyl thiophosphate, COMPOUND OF FORMULA I+dimefluazole, COMPOUND OF FORMULA I+dimetconazole, COMPOUND OF FORMULA I+dimethomorph, COMPOUND OF FORMULA I+dimethirimol, COMPOUND OF FORMULA I+dimoxystrobin, COMPOUND OF FORMULA I+diniconazole, COMPOUND OF FORMULA I+dinocap, COMPOUND OF FORMULA I+dithianon, COMPOUND OF FORMULA I+dodecyl dimethyl ammonium chloride, COMPOUND OF FORMULA I+dodemorph, COMPOUND OF FORMULA I+dodine, COMPOUND OF FORMULA I+doguadine, COMPOUND OF FORMULA I+edifenphos, COMPOUND OF FORMULA I+epoxiconazole, COMPOUND OF FORMULA I+ethirimol, COMPOUND OF FORMULA I+ethyl(Z)—N-benzyl-N([methyl(methyl-thioethylideneamino-oxycarbonyl)amino]thio)-β-alaninate, COMPOUND OF FORMULA I+etridiazole, COMPOUND OF FORMULA I+famoxadone, COMPOUND OF FORMULA I+fenamidone (RPA407213), COMPOUND OF FORMULA I+fenarimol, COMPOUND OF FORMULA I+fenbuconazole, COMPOUND OF FORMULA I+fenfuram, COMPOUND OF FORMULA I+fenhexamid (KBR2738), COMPOUND OF FORMULA I+fenoxanil, COMPOUND OF FORMULA I+fenpiclonil, COMPOUND OF FORMULA I+fen-propidin, COMPOUND OF FORMULA I+fenpropimorph, COMPOUND OF FORMULA I+fenpyrazamine/ipfenpyrazolone, COMPOUND OF FORMULA I+fentin acetate, COMPOUND OF FORMULA I+fentin hydroxide, COMPOUND OF FORMULA I+ferbam, COMPOUND OF FORMULA I+ferimzone, COMPOUND OF FORMULA I+fluazinam, COMPOUND OF FORMULA I+fludioxonil, COMPOUND OF FORMULA I+flumetover, COMPOUND OF FORMULA I+flumorph, COMPOUND OF FORMULA I+fluopicolide, COMPOUND OF FORMULA I+fluopyram, COMPOUND OF FORMULA I+fluoxastrobin, COMPOUND OF FORMULA I+fluoroimide, COMPOUND OF FORMULA I+fluquinconazole, COMPOUND OF FORMULA I+flusilazole, COMPOUND OF FORMULA I+flutianil, COMPOUND OF FORMULA I+flutolanil, COMPOUND OF FORMULA I+flutriafol, COMPOUND OF FORMULA I+fluxapyroxad, COMPOUND OF FORMULA I+folpet, COMPOUND OF FORMULA I+fuberidazole, COMPOUND OF FORMULA I+furalaxyl, COMPOUND OF FORMULA I+furametpyr, COMPOUND OF FOR- MULA I+guazatine, COMPOUND OF FORMULA I+hexaconazole, COMPOUND OF FORMULA I+hydroxyisoxazole, COMPOUND OF FORMULA I+hymexazole, COMPOUND OF FORMULA I+imazalil, COMPOUND OF FORMULA I+imibenconazole, COMPOUND OF FORMULA I+iminoctadine, COMPOUND OF FORMULA I+iminoctadine triacetate, COMPOUND OF FORMULA I+ipconazole, COMPOUND OF FORMULA I+iprobenfos, COMPOUND OF FORMULA I+iprodione, COMPOUND OF FORMULA I+iprovalicarb (SZX0722), COMPOUND OF FORMULA I+isopropanyl butyl carbamate, COMPOUND OF FORMULA I+isoprothiolane, COMPOUND OF FORMULA I+isopyrazam, COMPOUND OF FORMULA I+isotianil, COMPOUND OF FORMULA I+kasugamycin, COMPOUND OF FORMULA I+kresoxim-methyl, COMPOUND OF FORMULA I+LY186054, COMPOUND OF FORMULA I+LY211795, COMPOUND OF FORMULA I+LY248908, COMPOUND OF FORMULA I+mancozeb, COMPOUND OF FORMULA I+mandipropamid, COMPOUND OF FORMULA I+maneb, COMPOUND OF FORMULA I+mefenoxam, COMPOUND OF FORMULA I+mepanipyrim, COMPOUND OF FORMULA I+mepronil, COMPOUND OF FORMULA I+meptyldinocap, COMPOUND OF FORMULA I+metalaxyl, COMPOUND OF FORMULA I+metconazole, COMPOUND OF FORMULA I+metiram, COMPOUND OF FORMULA I+metiram-zinc, COMPOUND OF FORMULA I+metominostrobin, COMPOUND OF FORMULA I+metrafenone, COMPOUND OF FORMULA I+myclobutanil, COMPOUND OF FORMULA I+neoasozin, COMPOUND OF FORMULA I+nickel dimethyldithiocarbamate, COMPOUND OF FORMULA I+nicobifen, COMPOUND OF FORMULA I+nitrothal-isopropyl, COMPOUND OF FORMULA I+nuarimol, COMPOUND OF FORMULA I+ofurace, COMPOUND OF FORMULA I+organomercury compounds, COMPOUND OF FORMULA I+orysastrobin, COMPOUND OF FORMULA I+oxadixyl, COMPOUND OF FORMULA I+oxasulfuron, COMPOUND OF FORMULA I+oxolinic acid, COMPOUND OF FORMULA I+oxpoconazole, COMPOUND OF FORMULA I+oxycarboxin, COMPOUND OF FORMULA I+pefurazoate, COMPOUND OF FORMULA I+penconazole, COMPOUND OF FORMULA I+pencycuron, COMPOUND OF FORMULA I+penthiopyrad, COMPOUND OF FORMULA I+phenazin oxide, COMPOUND OF FORMULA I+phosetyl-Al, COMPOUND OF FORMULA I+phosphorus acids, COMPOUND OF FORMULA I+phthalide, COMPOUND OF FORMULA I+picoxystrobin (ZA1963), COMPOUND OF FORMULA I+polyoxin D, COMPOUND OF FORMULA I+polyram, COMPOUND OF FORMULA I+probenazole, COMPOUND OF FORMULA I+prochloraz, COMPOUND OF FORMULA I+procymidone, COMPOUND OF FORMULA I+propamocarb, COMPOUND OF FORMULA I+propiconazole, COMPOUND OF FORMULA I+propineb, COMPOUND OF FORMULA I+propionic acid, COMPOUND OF FORMULA I+proquinazid, COMPOUND OF FORMULA I+prothioconazole, COMPOUND OF FORMULA I+pyraclostrobin, COMPOUND OF FORMULA I+pyrazophos, COMPOUND OF FORMULA I+pyribencarb, COMPOUND OF FORMULA I+pyrifenox, COMPOUND OF FORMULA I+pyrimethanil, COMPOUND OF FORMULA I+pyroquilon, COMPOUND OF FORMULA I+pyroxyfur, COMPOUND OF FORMULA I+pyrrolnitrin, COMPOUND OF FORMULA I+quaternary ammonium compounds, COMPOUND OF FORMULA I+quinomethionate, COMPOUND OF FORMULA I+quinoxyfen, COMPOUND OF FORMULA I+quintozene, COMPOUND OF FORMULA I+sedaxane, COMPOUND OF FORMULA I+sipconazole (F-155), COMPOUND OF FORMULA I+sodium pentachlorophenate, COMPOUND OF FORMULA I+spiroxamine, COMPOUND OF FORMULA I+streptomycin, COMPOUND OF FORMULA I+sulphur, COMPOUND OF FORMULA I+tebuconazole, COMPOUND OF FORMULA I+tecloftalam, COMPOUND OF FORMULA I+tecnazene, COMPOUND OF FORMULA I+tetraconazole, COMPOUND OF FORMULA I+thiabendazole, COMPOUND OF FORMULA I+thifluzamid, COMPOUND OF FORMULA I+2-(thiocyanomethylthio)benzothiazole, COMPOUND OF FORMULA I+thiophanate-methyl, COMPOUND OF FORMULA I+thiram, COMPOUND OF FORMULA I+tiadinil, COMPOUND OF FORMULA I+timibenconazole, COMPOUND OF FORMULA I+tolclofos-methyl, COMPOUND OF FORMULA I+tolylfluanid, COMPOUND OF FORMULA I+triadimefon, COMPOUND OF FORMULA I+triadimenol, COMPOUND OF FORMULA I+triazbutil, COMPOUND OF FORMULA I+triazoxide, COMPOUND OF FORMULA I+tricyclazole, COMPOUND OF FORMULA I+tridemorph, COMPOUND OF FORMULA I+trifloxystrobin, COMPOUND OF FORMULA I+triforine, COMPOUND OF FORMULA I+triflumizole, COMPOUND OF FORMULA I+triticonazole, COMPOUND OF FORMULA I+validamycin A, COMPOUND OF FORMULA I+valiphenal, COMPOUND OF FORMULA I+vapam, COMPOUND OF FORMULA I+vinclozolin, COMPOUND OF FORMULA I+zineb and COMPOUND OF FORMULA I+ziram.

The compounds of formula I may be mixed with soil, peat or other rooting media for the protection of plants against seed-borne, soil-borne or foliar fungal diseases.

The compounds of formula I according to the invention can also be used in combination with one or more other synergists. In particular, the following mixtures of the COMPOUND OF FORMULA I, where this term preferably refers to a compound selected from one of the Tables A, B or C, are important:

COMPOUND OF FORMULA I+piperonyl butoxide, COMPOUND OF FORMULA I+sesamex, COMPOUND OF FORMULA I+safroxan and COMPOUND OF FORMULA I+dodecyl imidazole.

The compounds of formula I according to the invention can also be used in combination with one or more other herbicides. In particular, the following mixtures of the COMPOUND OF FORMULA I, where this term preferably refers to a compound selected from one of the Tables A, B or C, are important:

COMPOUND OF FORMULA I+acetochlor, COMPOUND OF FORMULA I+acifluorfen, COMPOUND OF FORMULA I+acifluorfen-sodium, COMPOUND OF FORMULA I+aclonifen, COMPOUND OF FORMULA I+acrolein, COMPOUND OF FORMULA I+alachlor, COMPOUND OF FORMULA I+alloxydim, COMPOUND OF FORMULA I+allyl alcohol, COMPOUND OF FORMULA I+ametryn, COMPOUND OF FORMULA I+amicarbazone, COMPOUND OF FORMULA I+amidosulfuron, COMPOUND OF FORMULA I+aminocyclopyrachlor, COMPOUND OF FORMULA I+aminopyralid, COMPOUND OF FORMULA I+amitrole, COMPOUND OF FORMULA I+ammonium sulfamate, COMPOUND OF FORMULA I+anilofos, COMPOUND OF FORMULA I+asulam, COMPOUND OF FORMULA I+atraton, COMPOUND OF FORMULA I+atrazine, COMPOUND OF FORMULA I+azimsulfuron, COMPOUND OF FORMULA I+BCPC, COMPOUND OF FORMULA I+beflubutamid, COMPOUND OF FORMULA I+benazolin, COMPOUND OF FORMULA I+bencarbazone, COMPOUND OF FORMULA I+benfluralin, COMPOUND OF FORMULA I+benfuresate, COMPOUND OF FORMULA I+bensulfuron, COMPOUND OF FORMULA I+bensulfuron-methyl, COMPOUND OF FORMULA I+bensulide, COMPOUND OF FORMULA I+bentazone, COMPOUND OF FORMULA I+benzfendizone, COMPOUND OF FORMULA I+benzobicyclon, COMPOUND OF FORMULA I+benzofenap, COMPOUND OF THE FORMULA I+bicyclopyrone, COMPOUND OF FORMULA I+bifenox, COMPOUND OF FORMULA I+bilanafos, COMPOUND OF FORMULA I+bispyribac, COMPOUND OF FORMULA I+bispyribac-sodium, COMPOUND OF FORMULA I+borax, COMPOUND OF FORMULA I+bromacil, COMPOUND OF FORMULA I+bromobutide, COMPOUND OF FORMULA I+bromoxynil, COMPOUND OF FORMULA I+butachlor, COMPOUND OF FORMULA I+butafenacil, COMPOUND OF FORMULA I+butamifos, COMPOUND OF FORMULA I+butralin, COMPOUND OF FORMULA I+butroxydim, COMPOUND OF FORMULA I+butylate, COMPOUND OF FORMULA I+cacodylic acid, COMPOUND OF FORMULA I+calcium chlorate, COMPOUND OF FORMULA I+cafenstrole, COMPOUND OF FORMULA I+carbetamide, COMPOUND OF FORMULA I+carfentrazone, COMPOUND OF FORMULA I+carfentrazone-ethyl, COMPOUND OF FORMULA I+CDEA, COMPOUND OF FORMULA I+CEPC, COMPOUND OF FORMULA I+chlorflurenol, COMPOUND OF FORMULA I+chlorflurenol-methyl, COMPOUND OF FORMULA I+chloridazon, COMPOUND OF FORMULA I+chlorimuron, COMPOUND OF FORMULA I+chlorimuron-ethyl, COMPOUND OF FORMULA I+chloroacetic acid, COMPOUND OF FORMULA I+chlorotoluron, COMPOUND OF FORMULA I+chlorpropham, COMPOUND OF FORMULA I+chlorsulfuron, COMPOUND OF FORMULA I+chlorthal, COMPOUND OF FORMULA I+chlorthal-dimethyl, COMPOUND OF FORMULA I+cinidon-ethyl, COMPOUND OF FORMULA I+cinmethylin, COMPOUND OF FORMULA I+cinosulfuron, COMPOUND OF FORMULA I+cisanilide, COMPOUND OF FORMULA I+clethodim, COMPOUND OF FORMULA I+clodinafop, COMPOUND OF FORMULA I+clodinafop-propargyl, COMPOUND OF FORMULA I+clomazone, COMPOUND OF FORMULA I+clomeprop, COMPOUND OF FORMULA I+clopyralid, COMPOUND OF FORMULA I+cloransulam, COMPOUND OF FORMULA I+cloransulam-methyl, COMPOUND OF FORMULA I+CMA, COMPOUND OF FORMULA I+4-CPB, COMPOUND OF FORMULA I+CPMF, COMPOUND OF FORMULA I+4-CPP, COMPOUND OF FORMULA I+CPPC, COMPOUND OF FORMULA I+cresol, COMPOUND OF FORMULA I+cumyluron, COMPOUND OF FORMULA I+cyanamide, COMPOUND OF FORMULA I+cyanazine, COMPOUND OF FORMULA I+cycloate, COMPOUND OF FORMULA I+cyclosulfamuron, COMPOUND OF FORMULA I+cycloxydim, COMPOUND OF FORMULA I+cyhalofop, COMPOUND OF FORMULA I+cyhalofop-butyl, COMPOUND OF FORMULA I+2,4-D, COMPOUND OF FORMULA I+3,4-DA, COMPOUND OF FORMULA I+daimuron, COMPOUND OF FORMULA I+dalapon, COMPOUND OF FORMULA I+dazomet, COMPOUND OF FORMULA I+2,4-DB, COMPOUND OF FORMULA I+3,4-DB, COMPOUND OF FORMULA I+2,4-DEB, COMPOUND OF FORMULA I+desmedipham, COMPOUND OF FORMULA I+dicamba, COMPOUND OF FORMULA I+dichlobenil, COMPOUND OF FORMULA I+ortho-dichlorobenzene, COMPOUND OF FORMULA I+para-dichlorobenzene, COMPOUND OF FORMULA I+dichlorprop, COMPOUND OF FORMULA I+dichlorprop-P, COMPOUND OF FORMULA I+diclofop, COMPOUND OF FORMULA I+diclofop-methyl, COMPOUND OF FORMULA I+diclosulam, COMPOUND OF FORMULA I+difenzoquat, COMPOUND OF FORMULA I+difenzoquat metilsulfate, COMPOUND OF FORMULA I+diflufenican, COMPOUND OF FORMULA I+diflufenzopyr, COMPOUND OF FORMULA I+dimefuron, COMPOUND OF FORMULA I+dimepiperate, COMPOUND OF FORMULA I+dimethachlor, COMPOUND OF FORMULA I+dimethametryn, COMPOUND OF FORMULA I+dimethenamid, COMPOUND OF FORMULA I+dimethenamid-P, COMPOUND OF FORMULA I+dimethipin, COMPOUND OF FORMULA I+dimethylarsinic acid, COMPOUND OF FORMULA I+dinitramine, COMPOUND OF FORMULA I+dinoterb, COMPOUND OF FORMULA I+diphenamid, COMPOUND OF FORMULA I+diquat, COMPOUND OF FORMULA I+diquat dibromide, COMPOUND OF FORMULA I+dithiopyr, COMPOUND OF FORMULA I+diuron, COMPOUND OF FORMULA I+DNOC, COMPOUND OF FORMULA I+3,4-DP, COMPOUND OF FORMULA I+DSMA, COMPOUND OF FORMULA I+EBEP, COMPOUND OF FORMULA I+endothal, COMPOUND OF FORMULA I+EPTC, COMPOUND OF FORMULA I+esprocarb, COMPOUND OF FORMULA I+ethalfluralin, COMPOUND OF FORMULA I+ethametsulfuron, COMPOUND OF FORMULA I+ethametsulfuron-methyl, COMPOUND OF FORMULA I+ethofumesate, COMPOUND OF FORMULA I+ethoxyfen, COMPOUND OF FORMULA I+ethoxysulfuron, COMPOUND OF FORMULA I+etobenzanid, COMPOUND OF FORMULA I+fenoxaprop-P, COMPOUND OF FORMULA I+fenoxaprop-P-ethyl, COMPOUND OF FORMULA I+fentrazamide, COMPOUND OF FORMULA I+ferrous sulfate, COMPOUND OF FORMULA I+flamprop-M, COMPOUND OF FORMULA I+flazasulfuron, COMPOUND OF FORMULA I+florasulam, COMPOUND OF FORMULA I+fluazifop, COMPOUND OF FORMULA I+fluazifop-butyl, COMPOUND OF FORMULA I+fluazifop-P, COMPOUND OF FORMULA I+fluazifop-P-butyl, COMPOUND OF FORMULA I+flucarbazone, COMPOUND OF FORMULA I+flucarbazone-sodium, COMPOUND OF FORMULA I+flucetosulfuron, COMPOUND OF FORMULA I+fluchloralin, COMPOUND OF FORMULA I+flufenacet, COMPOUND OF FORMULA I+flufenpyr, COMPOUND OF FORMULA I+flufenpyr-ethyl, COMPOUND OF FORMULA I+flumetsulam, COMPOUND OF FORMULA I+flumiclorac, COMPOUND OF FORMULA I+flumiclorac-pentyl, COMPOUND OF FORMULA I+flumioxazin, COMPOUND OF FORMULA I+fluometuron, COMPOUND OF FORMULA I+fluoroglycofen, COMPOUND OF FORMULA I+fluoroglycofen-ethyl, COMPOUND OF FORMULA I+flupropanate, COMPOUND OF FORMULA I+flupyrsulfuron, COMPOUND OF FORMULA I+flupyrsulfuron-methyl-sodium, COMPOUND OF FORMULA I+flurenol, COMPOUND OF FORMULA I+fluridone, COMPOUND OF FORMULA I+fluorochloridone, COMPOUND OF FORMULA I+fluoroxypyr, COMPOUND OF FORMULA I+flurtamone, COMPOUND OF FORMULA I+fluthiacet, COMPOUND OF FORMULA I+fluthiacet-methyl, COMPOUND OF FORMULA I+fomesafen, COMPOUND OF FORMULA I+foramsulfuron, COMPOUND OF FORMULA I+fosamine, COMPOUND OF FORMULA I+glufosinate, COMPOUND OF FORMULA I+glufosinate-ammonium, COMPOUND OF FORMULA I+glufosinate-P, COMPOUND OF FORMULA I+glyphosate, COMPOUND OF FORMULA I+glyphosate-trimesium, COMPOUND OF FORMULA I+halosulfuron, COMPOUND OF FORMULA I+halosulfuron-methyl, COMPOUND OF FORMULA I+haloxyfop, COMPOUND OF FORMULA I+haloxyfop-P, COMPOUND OF FORMULA I+HC-252, COMPOUND OF FORMULA I+hexazinone, COMPOUND OF FORMULA I+imazamethabenz, COMPOUND OF FORMULA I+imazamethabenz-methyl, COMPOUND OF FORMULA I+imazamox, COMPOUND OF FORMULA I+imazapic, COMPOUND OF FORMULA I+imazapyr, COMPOUND OF FORMULA I+imazaquin, COMPOUND OF FORMULA I+imazethapyr, COMPOUND OF FORMULA I+imazosulfuron, COMPOUND OF FORMULA I+indanofan, COMPOUND OF FORMULA I+indaziflam, COMPOUND OF FORMULA I+iodomethane, COMPOUND OF FORMULA I+iodosulfuron, COMPOUND OF FORMULA I+iodosulfuron-methyl-sodium, COMPOUND OF FORMULA I+ioxynil, COMPOUND OF FORMULA I+ipfencarbazone, COMPOUND OF FORMULA I+isoproturon, COMPOUND OF FORMULA I+isouron, COMPOUND OF FORMULA I+isoxaben, COMPOUND OF FORMULA I+isoxachlortole, COMPOUND OF FORMULA I+isoxaflutole, COMPOUND OF FORMULA I+karbutilate, COMPOUND OF FORMULA I+lactofen, COMPOUND OF FORMULA I+lenacil, COMPOUND OF FORMULA I+linuron, COMPOUND OF FORMULA I+MAA, COMPOUND OF FORMULA I+MAMA, COMPOUND OF FORMULA I+MCPA, COMPOUND OF FORMULA I+MCPA-thioethyl, COMPOUND OF FORMULA I+MCPB, COMPOUND OF FORMULA I+mecoprop, COMPOUND OF FORMULA I+mecoprop-P, COMPOUND OF FORMULA I+mefenacet, COMPOUND OF FORMULA I+mefluidide, COMPOUND OF FORMULA I+mesosulfuron, COMPOUND OF FORMULA I+mesosulfuron-methyl, COMPOUND OF FORMULA I+mesotrione, COMPOUND OF FORMULA I+metam, COMPOUND OF FORMULA I+metamifop, COMPOUND OF FORMULA I+metamitron, COMPOUND OF FORMULA I+metazachlor, COMPOUND OF FORMULA I+methabenzthiazuron, COMPOUND OF FORMULA I+methylarsonic acid, COMPOUND OF FORMULA I+methyldymron, COMPOUND OF FORMULA I+methyl isothiocyanate, COMPOUND OF FORMULA I+metobenzuron, COMPOUND OF FORMULA I+metolachlor, COMPOUND OF FORMULA I+S-metolachlor, COMPOUND OF FORMULA I+metosulam, COMPOUND OF FORMULA I+metoxuron, COMPOUND OF FORMULA I+metribuzin, COMPOUND OF FORMULA I+metsulfuron, COMPOUND OF FORMULA I+metsulfuron-methyl, COMPOUND OF FORMULA I+MK-616, COMPOUND OF FORMULA I+molinate, COMPOUND OF FORMULA I+monolinuron, COMPOUND OF FORMULA I+MSMA, COMPOUND OF FORMULA I+naproanilide, COMPOUND OF FORMULA I+napropamide, COMPOUND OF FORMULA I+naptalam, COMPOUND OF FORMULA I+neburon, COMPOUND OF FORMULA I+nicosulfuron, COMPOUND OF FORMULA I+nonanoic acid, COMPOUND OF FORMULA I+norflurazon, COMPOUND OF FORMULA I+oleic acid (fatty acids), COMPOUND OF FORMULA I+orbencarb, COMPOUND OF FORMULA I+orthosulfamuron, COMPOUND OF FORMULA I+oryzalin, COMPOUND OF FORMULA I+oxadiargyl, COMPOUND OF FORMULA I+oxadiazon, COMPOUND OF FORMULA I+oxasulfuron, COMPOUND OF FORMULA I+oxaziclomefone, COMPOUND OF FORMULA I+oxyfluorfen, COMPOUND OF FORMULA I+paraquat, COMPOUND OF FORMULA I+paraquat dichloride, COMPOUND OF FORMULA I+pebulate, COMPOUND OF FORMULA I+pendimethalin, COMPOUND OF FORMULA I+penoxsulam, COMPOUND OF FORMULA I+pentachlorophenol, COMPOUND OF FORMULA I+pentanochlor, COMPOUND OF FORMULA I+pentoxazone, COMPOUND OF FORMULA I+pethoxamid, COMPOUND OF FORMULA I+petrolium oils, COMPOUND OF FORMULA I+phenmedipham, COMPOUND OF FORMULA I+phenmedipham-ethyl, COMPOUND OF FORMULA I+picloram, COMPOUND OF FORMULA I+picolinafen, COMPOUND OF FORMULA I+pinoxaden, COMPOUND OF FORMULA I+piperophos, COMPOUND OF FORMULA I+potassium arsenite, COMPOUND OF FORMULA I+potassium azide, COMPOUND OF FORMULA I+pretilachlor, COMPOUND OF FORMULA I+primisulfuron, COMPOUND OF FORMULA I+primisulfuron-methyl, COMPOUND OF FORMULA I+prodiamine, COMPOUND OF FORMULA I+profluazol, COMPOUND OF FORMULA I+profoxydim, COMPOUND OF FORMULA I+prometon, COMPOUND OF FORMULA I+prometryn, COMPOUND OF FORMULA I+propachlor, COMPOUND OF FORMULA I+propanil, COMPOUND OF FORMULA I+propaquizafop, COMPOUND OF FORMULA I+propazine, COMPOUND OF FORMULA I+propham, COMPOUND OF FORMULA I+propisochlor, COMPOUND OF FORMULA I+propoxycarbazone, COMPOUND OF FORMULA I+propoxycarbazone-sodium, COMPOUND OF FORMULA I+propyrisulfuron, COMPOUND OF FORMULA I+propyzamide, COMPOUND OF FORMULA I+prosulfocarb, COMPOUND OF FORMULA I+prosulfuron, COMPOUND OF FORMULA I+pyraclonil, COMPOUND OF FORMULA I+pyraflufen, COMPOUND OF FORMULA I+pyraflufen-ethyl, COMPOUND OF FORMULA I+pyrasulfutole, COMPOUND OF FORMULA I+pyrazolynate, COMPOUND OF FORMULA I+pyrazosulfuron, COMPOUND OF FORMULA I+pyrazosulfuron-ethyl, COMPOUND OF FORMULA I+pyrazoxyfen, COMPOUND OF FORMULA I+pyribenzoxim, COMPOUND OF FORMULA I+pyributicarb, COMPOUND OF FORMULA I+pyridafol, COMPOUND OF FORMULA I+pyridate, COMPOUND OF FORMULA I+pyriftalid, COMPOUND OF FORMULA I+pyriminobac, COMPOUND OF FORMULA I+pyriminobac-methyl, COMPOUND OF FORMULA I+pyrimisulfan, COMPOUND OF FORMULA I+pyrithiobac, COMPOUND OF FORMULA I+pyrithiobac-sodium, COMPOUND OF FORMULA I+pyroxsulam, COMPOUND OF FORMULA I+pyroxasulfone, COMPOUND OF FORMULA I+quinclorac, COMPOUND OF FORMULA I+quinmerac, COMPOUND OF FORMULA I+quinoclamine, COMPOUND OF FORMULA I+quizalofop, COMPOUND OF FORMULA I+quizalofop-P, COMPOUND OF FORMULA I+rimsulfuron, COMPOUND OF FORMULA I+saflufenacil, COMPOUND OF FORMULA I+sethoxydim, COMPOUND OF FORMULA I+siduron, COMPOUND OF FORMULA I+simazine, COMPOUND OF FORMULA I+simetryn, COMPOUND OF FORMULA I+SMA, COMPOUND OF FORMULA I+sodium arsenite, COMPOUND OF FORMULA I+sodium azide, COMPOUND OF FORMULA I+sodium chlorate, COMPOUND OF FORMULA I+sulcotrione, COMPOUND OF FORMULA I+sulfentrazone, COMPOUND OF FORMULA I+sulfometuron, COMPOUND OF FORMULA I+sulfometuron-methyl, COMPOUND OF FORMULA I+sulfosate, COMPOUND OF FORMULA I+sulfosulfuron, COMPOUND OF FORMULA I+sulfuric acid, COMPOUND OF FORMULA I+tar oils, COMPOUND OF FORMULA I+2,3,6-TBA, COMPOUND OF FORMULA I+TCA, COMPOUND OF FORMULA I+TCA-sodium, COMPOUND OF FORMULA I+tebuthiuron, COMPOUND OF FORMULA I+tefuryltrione, COMPOUND OF FORMULA I+tembotrione, COMPOUND OF FORMULA I+tepraloxydim, COMPOUND OF FORMULA I+terbacil, COMPOUND OF FORMULA I+terbumeton, COMPOUND OF FORMULA I+terbuthylazine, COMPOUND OF FORMULA I+terbutryn, COMPOUND OF FORMULA I+thenylchlor, COMPOUND OF FORMULA I+thiazopyr, COMPOUND OF FORMULA I+thiencarbazone, COMPOUND OF FORMULA I+thifensulfuron, COMPOUND OF FORMULA I+thifensulfuron-methyl, COMPOUND OF FORMULA I+thiobencarb, COMPOUND OF FORMULA I+tiocarbazil, COMPOUND OF FORMULA I+topramezone, COMPOUND OF FORMULA I+tralkoxydim, COMPOUND OF FORMULA I+tri-allate, COMPOUND OF FORMULA I+triasulfuron, COMPOUND OF FORMULA I+triaziflam, COMPOUND OF FORMULA I+tribenuron, COMPOUND OF FORMULA I+tribenuron-methyl, COMPOUND OF FORMULA I+tricamba, COMPOUND OF FORMULA I+triclopyr, COMPOUND OF FORMULA I+trietazine, COMPOUND OF FORMULA I+trifloxysulfuron, COMPOUND OF FORMULA I+trifloxysulfuron-sodium, COMPOUND OF FORMULA I+trifluralin, COMPOUND OF FORMULA I+triflusulfuron, COMPOUND OF FORMULA I+triflusulfuron-methyl, COMPOUND OF FORMULA I+trihydroxytriazine, COMPOUND OF FORMULA I+tritosulfuron, COMPOUND OF FORMULA I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS RN 353292-31-6), COMPOUND OF FORMULA I+4-[(4,5-dihydro-3-methoxy-4-methyl-5-oxo)-1H-1,2,4-triazol-1-ylcarbonyl-sulfamoyl]-5-methylthiophene-3-carboxylic acid (BAY636), COMPOUND OF FORMULA I+BAY747 (CAS RN 335104-84-2), COMPOUND OF FORMULA I+topramezone (CAS RN 210631-68-8), COMPOUND OF FORMULA I+4-hydroxy-3-[[2-[(2-methoxyethoxy)methyl]-6-(trifluoromethyl)-3-pyridinyl]carbonyl]-bicyclo[3.2.1]oct-3-en-2-one (CAS RN 352010-68-5), and COMPOUND OF FORMULA I+4-hydroxy-3-[[2-(3-methoxypropyl)-6-(difluoromethyl)-3-pyridinyl]carbonyl]-bicyclo[3.2.1]oct-3-en-2-one.

The compounds of formula (I) according to the invention can also be used in combination with safeners. Preferably, in these mixtures, the compound of the formula (I) is one of those compounds listed in Tables A, B or C above. The following mixtures with safeners, especially, come into consideration:
compound of formula (I)+cloquintocet-mexyl, compound of formula (I)+cloquintocet acid and salts thereof, compound of formula (I)+fenchlorazole-ethyl, compound of formula (I)+fenchlorazole acid and salts thereof, compound of formula (I)+mefenpyr-diethyl, compound of formula (I)+mefenpyr diacid, compound of formula (I)+isoxadifen-ethyl, compound of formula (I)+isoxadifen acid, compound of formula (I)+furilazole, compound of formula (I)+furilazole R isomer, compound of formula (I)+benoxacor, compound of formula (I)+dichlormid, compound of formula (I)+AD-67, compound of formula (I)+oxabetrinil, compound of formula (I)+cyometrinil, compound of formula (I)+cyometrinil Z-isomer, compound of formula (I)+fenclorim, compound of formula (I)+cyprosulfamide, compound of formula (I)+naphthalic anhydride, compound of formula (I)+flurazole, compound of formula (I)+N-(2-methoxybenzoyl)-4-[(methylaminocarbonyl)amino]benzenesulfonamide, compound of formula (I)+CL 304,415, compound of formula (I)+dicyclonon, compound of formula (I)+fluxofenim, compound of formula (I)+DKA-24, compound of formula (I)+R-29148 and compound of formula (I)+PPG-1292. A safening effect can also be observed for the mixtures compound of the formula (I)+dymron, compound of the formula (I)+MCPA, compound of the formula (I)+mecoprop and compound of the formula (I)+mecoprop-P.

The mixing partners of the compound of formula I may also be in the form of esters or salts, as mentioned e.g. in The Pesticide Manual, 12th Edition (BCPC), 2000.

In the above different lists of active ingredients to be mixed with a COMPOUND OF FORMULA I, the compound of the formula I is preferably a compound of Tables A, B or C; and more preferably, a compound selected from A1, A10, A100, A102, A103, A104, A105, A106, A107, A108, A109, A11, A110, A111, A112, A114, A117, A118, A119, A12, A120, A121, A122, A123, A125, A126, A127, A128, A129, A13, A131, A132, A133, A138, A139, A14, A140, A141, A142, A144, A145, A146, A147, A148, A149, A15, A150, A152, A153, A154, A155, A156, A159, A16, A160, A161, A162, A163, A164, A165, A167, A168, A169, A17, A170, A171, A172, A173, A175, A176, A177, A179, A182, A183, A184, A185, A186, A187, A188, A190, A191, A192, A193, A194, A195, A196, A198, A199, A2, A20, A200, A201, A202, A205, A206, A207, A208, A209, A21, A210, A211, A213, A214, A215, A216, A217, A218, A219, A22, A220, A221, A222, A223, A225, A23, A24, A28, A29, A3, A31, A35, A36, A37, A38, A39, A4, A40, A41, A43, A44, A45, A46, A47, A48, A49, A5, A51, A54, A55, A56, A57, A58, A6, A60, A61, A62, A63, A64, A65, A66, A67, A68, A69, A7, A72, A75, A76, A77, A78, A79, A8, A80, A81, A83, A84, A85, A86, A87, A88, A89, A9, A90, A91, A93, A96, A97, A98, A99, B6, C10, C11, C12, C13, C14, C15, C16, C17, C18, C19, C2, C20, C21, C21, C3, C4, C5, C6, C7, C9.

In the above-mentioned mixtures of compounds of formula I, in particular a compound selected from said Tables A, B or C, with other insecticides, fungicides, herbicides, safeners, adjuvants and the like, the mixing ratios can vary over a large range and are, preferably 100:1 to 1:6000, especially 50:1 to 1:50, more especially 20:1 to 1:20, even more especially 10:1 to 1:10. Those mixing ratios are understood to include, on the one hand, ratios by weight and also, on other hand, molar ratios.

The mixtures can advantageously be used in the above-mentioned formulations (in which case "active ingredient" relates to the respective mixture of compound of formula I with the mixing partner).

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The mixtures comprising a compound of formula I selected from Tables A, B or C and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables A, B or C and the active ingredients as described above is not essential for working the present invention.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

PREPARATION OF EXAMPLES

Intermediate I1

2,6-dichloro-4-(1,2,2,3,3,3-hexafluoro-1-(trifluoromethyl)propyl)-phenylamine

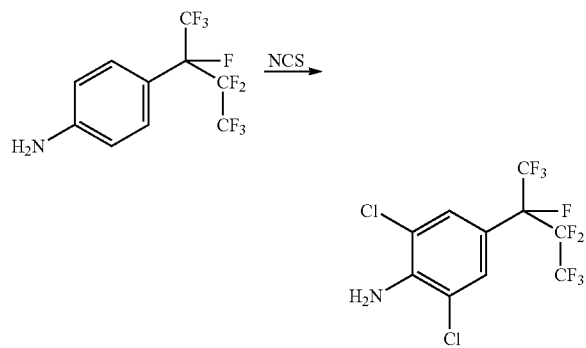

To a solution of 4-(1,2,2,3,3,3-hexafluoro-1-(trifluoromethyl)propyl)phenylamine (prepared according to the method of EP 1,006,102) (14 g, 45 mmol) in dichloromethane (100 ml) was added N-chlorosuccinimide (NCS) (15 g, 112.5 mmol). The reaction mixture was stirred at ambient temperature overnight. The reaction mixture was concentrated and the residue partitioned between dichloromethane (200 ml) and an aqueous solution of sodium hydroxide (200 ml, 5N). The phases were separated and the aqueous phase was extracted twice with dichloromethane. The combined organic extracts were dried over sodium sulfate and concentrated. The residue was used without extra purification to give 2,6-dichloro-4-(1,2,2,3,3,3-hexafluoro-1-(trifluoromethyl)propyl)phenylamine (16 g, 94% yield).

$^1$H NMR (400 MHz, CDCl$_3$): 7.39 (s, 2H), 4.76 (bs, 2H).

Intermediate I2

2-azido-1,3-dichloro-5-(1,2,2,3,3,3-hexafluoro-1-(trifluoromethyl)-propyl)benzene

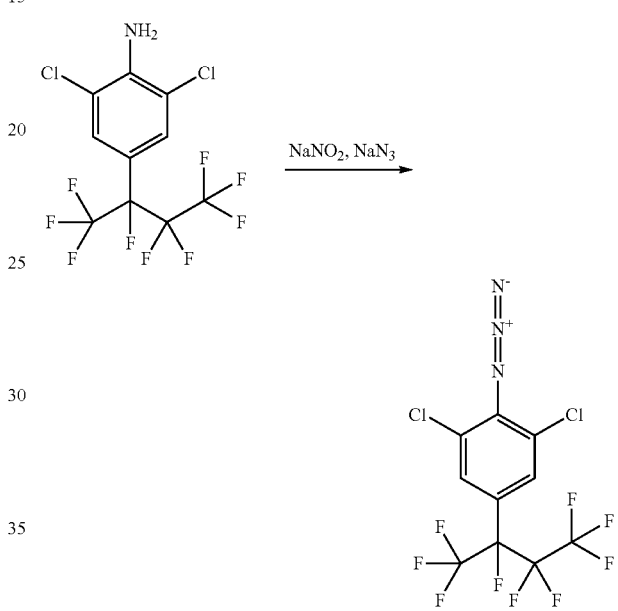

2,6-dichloro-4-(1,2,2,3,3,3-hexafluoro-1-(trifluoromethyl)propyl)phenylamine (Intermediate I1; 1.90 g; 5 mmol) was added to a mixture of water (85 ml) and concentrated HCl (aq) (85 ml) and the mixture was stirred at room temperature for 30 minutes. Sodium nitrite (0.345 g; 5 mmol) dissolved in water (8.5 ml) was added in a dropwise manner to the mixture, which was kept at a temperature between 0 to 5° C. After the mixture had been stirred for 30 minutes, sodium azide (0.325 g; 5 mmol) dissolved in water (8.5 ml) was added in a dropwise manner to the mixture, and the mixture was stirred overnight at RT. After the reaction was complete the mixture was extracted with dichloromethane (3×40 ml), and the extract was dried (Na$_2$SO$_4$). The dichloromethane was evaporated and the residue was chromatographed on silica gel (100 g SiO$_2$; iHEX), giving the corresponding azide (0.754 g; 37.14%) as an orange-brown oil. This compound was used without extra purification, often it was contained with the starting material (2,6-dichloro-4-(1,2,2,3,3,3-hexafluoro-1-(trifluoromethyl)propyl)phenylamine).

All of the azide used in the following examples were prepared by the same method: 2-azido-1-ethyl-5-(1,2,2,3,3,3-hexafluoro-1-(trifluoromethyl)propyl)-3-methylbenzene; 2-azido-1-bromo-3-methyl-5-(1,2,2,2-tetrafluoro-1-(trifluoromethyl)ethyl)benzene; 2-azido-1,3-dichloro-5-(1,2,2,2-tetrafluoro-1-(trifluoromethyl)ethyl)benzene.

Intermediate I3

3-{1-[2,6-dichloro-4-(1,2,2,3,3,3-hexafluoro-1-(trifluoromethyl)-propyl)phenyl]-1H-1,2,3-triazol-4-yl}phenylamine

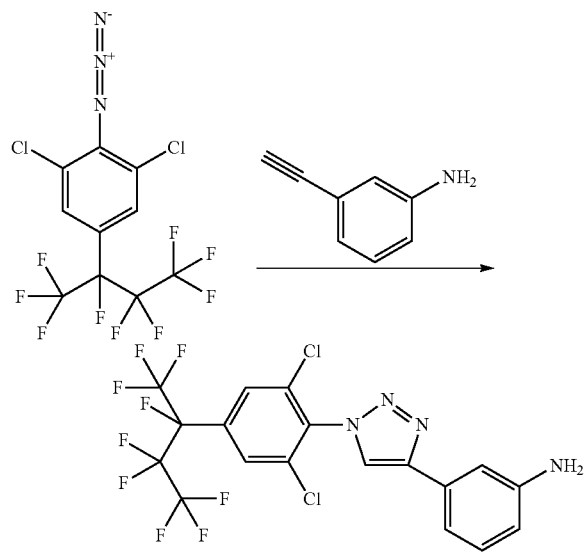

Ethynylaniline and 2-azido-1,3-dichloro-5-(1,2,2,3,3,3-hexafluoro-1-(trifluoromethyl)-propyl)benzene were suspended in a mixture of water and t-BuOH. Sodium ascorbate (0.055 ml 1 M sol. in water, freshly prepared) was added to the mixture followed by copper (II) sulfate pentahydrate (1.4 mg in 0.06 ml of water). The resulting heterogeneous mixture was stirred vigorously overnight. The reaction mixture was diluted with water and cooled in an ice bath. The product was extracted with ethyl acetate, dried and evaporated. The residue was subjected to silica gel column chromatography (iHEX/EtOAc=3:1) affording the desired product as a light brown powder.

Compounds B2 to B4 from table B were prepared by the same method.

Intermediate I4

4-Ethynyl-1-fluoro-2-nitro-benzene

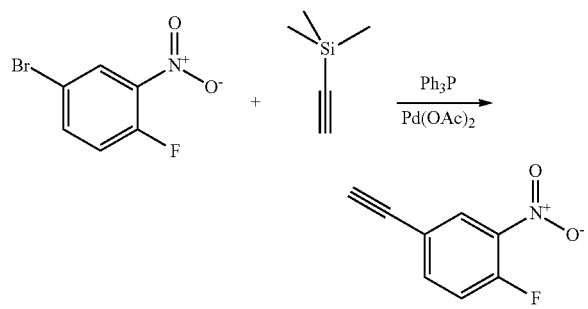

A turbid solution of 25 g of 1-bromo-3-nitro-4-fluorobenzene (113.64 mmol), 26.0 ml of ethynyltrimethylsilane (184.1 mmol), 0.612 g of palladium(II) acetate (2.73 mmol), and 1.192 g of triphenylphosphine (4.55 mmol) in 300 mL of deaerated, anhydrous triethylamine was rapidly heated to gentle reflux under argon. At ca. 100° C., a brown solution resulted, and a white precipitate began to form after 15 min at reflux. After 4 h, the mixture was cooled and the crystalline white solid of triethylamine hydrobromide was isolated by filtration. The dark brown filtrate was concentrated, mixed with 250 mL of aqueous sodium bicarbonate, and extracted with dichloromethane (3×100 ml). The organic fractions were combined, dried over magnesium sulfate, and concentrated to yield an oil, which was dissolved in 200 ml of THF and treated with 40 ml of TBAF 1N. The mixture was concentrated and the residue dissolved in ethyl acetate, washed with water, dried, concentrated in vacuo, and chromatographed with cyclohexane to give 4-ethynyl-1-fluoro-2-nitrobenzene (3.8 g, 20% yield).

$^1$H NMR (400 MHz, CDCl$_3$): 8.18 (d, 1H), 7.72 (m, 1H), 7.26 (m, 1H), 3.18 (s, 1H) ppm.

Intermediate I5

1-[2,6-Dichloro-4-(1,2,2,3,3,3-hexafluoro-1-(trifluoromethyl)propyl)-phenyl]-4-(4-fluoro-3-nitrophenyl)-1H-1,2,3-triazole

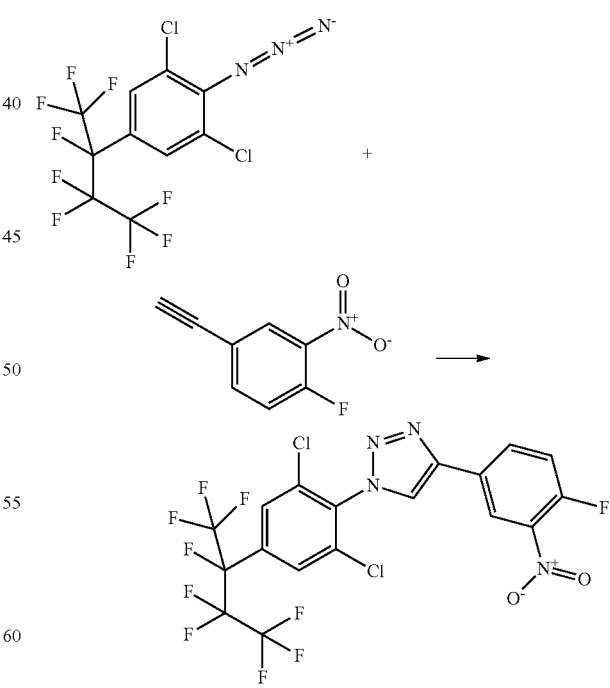

4-Ethynyl-1-fluoro-2-nitrobenzene (3.63 g, 22 mmol) and 2-azido-1,3-dichloro-5-(1,2,2,3,3,3-hexafluoro-1-(trifluoromethyl)propyl)benzene (8.93 g, 22.0 mmol) were suspended in a mixture of water and t-BuOH (1:1, 100 mL).

Sodium ascorbate (2.2 ml, 1 M sol. in water, freshly prepared) was added to the mixture followed by copper (II) sulfate pentahydrate (0.055 g). The resulting heterogeneous mixture was stirred vigorously at room temperature for 96 hours. The reaction mixture was diluted with water and cooled in an ice bath. The orange product which precipitated was filtered and dried. The residue was subjected to silica gel column chromatography (ethyl acetate:cyclohexane 1:9) affording the desired product (9 g, 72% yield). LC-MS (Method A, Negative) RT 2.17 (615, M+HCOO−).

Intermediate I6

4-{1-[2,6-Dichloro-4-(1,2,2,3,3,3-hexafluoro-1-(trifluoromethyl)-phenyl]-1H-1,2,3-triazol-4-yl}-2-nitrobenzonitrile

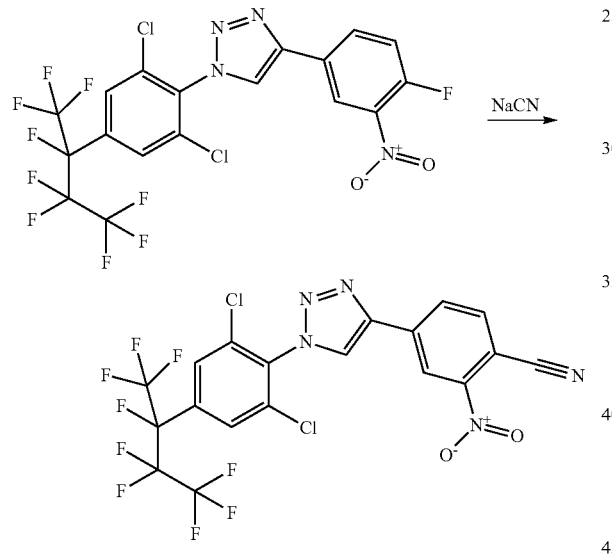

To a solution of 1-[2,6-dichloro-4-(1,2,2,3,3,3-hexafluoro-1-(trifluoromethyl)propyl)-phenyl]-4-(4-fluoro-3-nitrophenyl)-1H-1,2,3-triazole (Intermediate I5) (6.97 g, 12.20 mmol) in dimethyl formamide (50 ml) was added sodium cyanide (0.658 g, 13.42 mmol). The reaction mixture was stirred at ambient temperature for 24 hours. The mixture of water (100 mL) and ethyl acetate (100 mL) was added. The aqueous and organic phases were separated. The aqueous phase was extracted twice with ethyl acetate. The combined organic extracts were dried over sodium sulfate and concentrated. The residue was purified by column chromatography on silica gel (Büchi sampler, SiOH 150*40, Gradient 1% to 30% ethyl acetate in cyclohexane over 70 min.) to give 4-{1-[2,6-dichloro-4-(1,2,2,3,3,3-hexafluoro-1-(trifluoromethyl)propyl)phenyl]-1H-1,2,3-triazol-4-yl}-2-nitrobenzonitrile (1.10 g, 16%).

$^1$H NMR (400 MHz, CDCl$_3$): 8.82 (s, 1H), 8.45 (d, 1H), 8.27 (s, 1H), 8.04 (d, 1H), 7.81 (s, 2H) ppm.

Intermediate I7

2-Amino-4-{1-[2,6-dichloro-4-(1,2,2,3,3,3-hexafluoro-1-(trifluoromethyl)-propyl)phenyl]-1H-1,2,3-triazol-4-yl}benzonitrile (Compound B6)

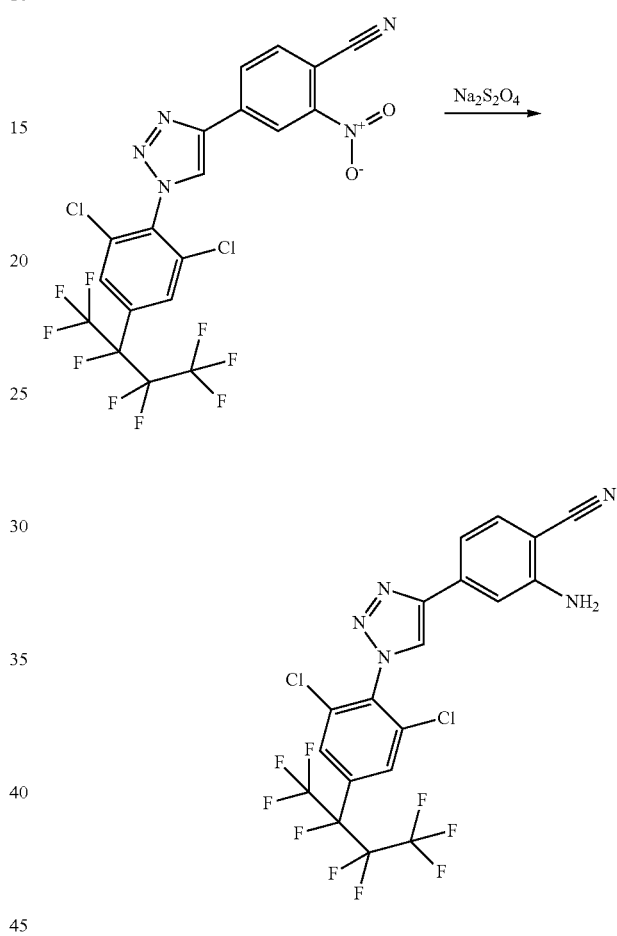

To a solution of 4-{1-[2,6-dichloro-4-(1,2,2,3,3,3-hexafluoro-1-(trifluoromethyl)-propyl)phenyl]-1H-1,2,3-triazol-4-yl}-2-nitrobenzonitrile (Intermediate I6) (1.11 g, 1.92 mmol) in tetrahydrofuran (30 ml) was added aqueous sodium hydroxide (0.1 M) (10 ml), sodium hydrosulfite (3.00 g, 14.13 mmol) and tetrabutylammonium bromide ("TBAB") (0.124 g, 0.38 mmol). The reaction mixture was stirred at ambient temperature for 3 hours. The mixture of water (100 mL) and ethyl acetate (100 mL) was added. The aqueous and organic phases were separated. The aqueous phase was extracted twice with ethyl acetate. The combined organic extracts were dried over sodium sulfate and concentrated. The residue was purified by column on silica gel (ethylacetate:cyclohexane 1:9 to 1:4) to give 2-amino-4-{1-[2,6-dichloro-4-(1,2,2,3,3,3-hexafluoro-1-(trifluoromethyl)propyl)phenyl]-1H-1,2,3-triazol-4-yl}-benzonitrile (Compound B6) (0.66 g, 63% yield).

Intermediate I8

5-{1-[2,6-Dichloro-4-(1,2,2,3,3,3-hexafluoro-1-(trifluoromethyl)-phenyl]-1H-1,2,3-triazol-4-yl}-2-fluorophenylamine

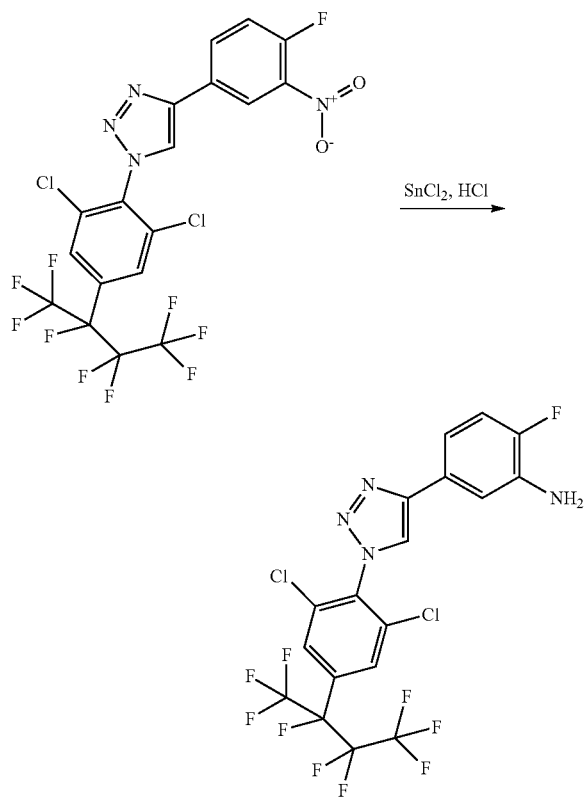

(Compound B5)

To a solution of 1-[2,6-dichloro-4-(1,2,2,3,3,3-hexafluoro-1-(trifluoromethyl)propyl)-phenyl]-4-(4-fluoro-3-nitrophenyl)-1H-1,2,3-triazole (2.00 g, 3.51 mmol) (Intermediate I5) in isopropanol (15 ml) was added tin chloride (3.17 g, 14.04 mmol). The mixture was cooled to 0° C. and 1.15 ml of concentrated hydrochloric acid (37%) was added slowly. The mixture was stirred at 80° C. for 2 hours. Then about a third of the total volume of isopropanol was evaporated. Water (100 ml) was added to the concentrated mixture followed by aqueous sodium hydroxide (4N) to adjust the pH to 8 to 9. The aqueous phase was extracted three times with ethyl acetate (200 ml). The combined organic extracts were dried over sodium sulfate and the solvent evaporated. The residue was purified by filtration on Hyfloto give 5-{1-[2,6-dichloro-4-(1,2,2,3,3,3-hexafluoro-1-(trifluoromethyl)propyl)phenyl]-1H-1,2,3-triazol-4-yl}-2-fluorophenylamine (B5, 1.60 g, 84% yield). The compound was used without extra purification. LC-MS (Method A, Negative) RT 2.09 (541, MH$^+$).

Compounds B7 to B13 from table B were prepared by the same methods that described for compounds B1 to B6 with the adapted reagents.

Example A1

4-cyano-N-(3-{1-[2,6-dichloro-4-(1,2,2,3,3,3-hexafluoro-1-(trifluoromethyl)-propyl)phenyl]-1H-1,2,3-triazol-4-yl}phenyl)benzamide

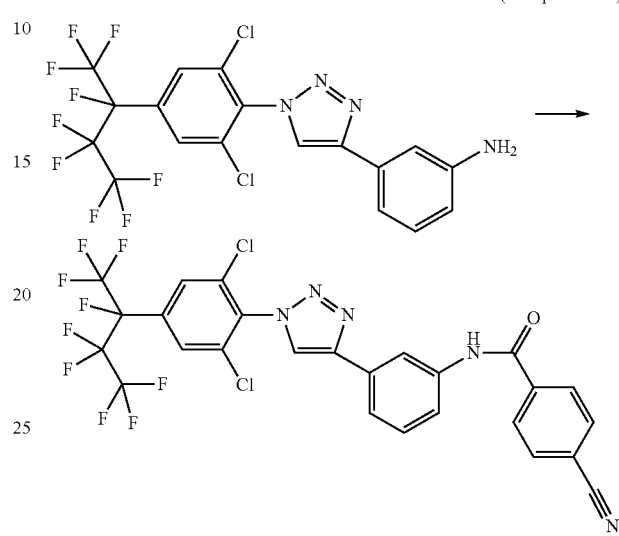

(Compound A1)

A solution of 4-cyanobenzoyl chloride (0.33 mmol, 1.5 eq.) in 3 ml dry THF was added dropwise to a solution of 3-{1-[2,6-dichloro-4-(1,2,2,3,3,3-hexafluoro-1-(trifluoromethyl)-propyl)phenyl]-1H-1,2,3-triazol-4-yl}phenylamine (0.22 mmol) and pyridine (0.66 mmol) in 4 ml of dry THF over 5 min at RT. The mixture was stirred overnight at RT. The mixture was concentrated in vacuo and dissolved in a mixture of ethyl acetate and water. The organic layer and the aqueous layer were separated, then the organic phase was washed with 1N—HCl, sat. NaHCO$_3$ and brine. The organic phase was dried with sodium sulfate and the solvent was evaporated in vacuo. The residue was purified by column chromatography (iHEX:EtOAc=3:1). The product was isolated as a viscous oil, which solidified after 1 to 2 days (glassy solid).

Compounds A2 to A19 and A213 to A225 from table A were prepared by the same method.

Example A20

N-(3-{1-[2-Bromo-6-ethyl-4-(1,2,2,2-tetrafluoro-1-trifluoromethyl-ethyl)-phenyl]-1H-[1,2,3]triazol-4-yl}-phenyl)-2-fluoro-benzamide

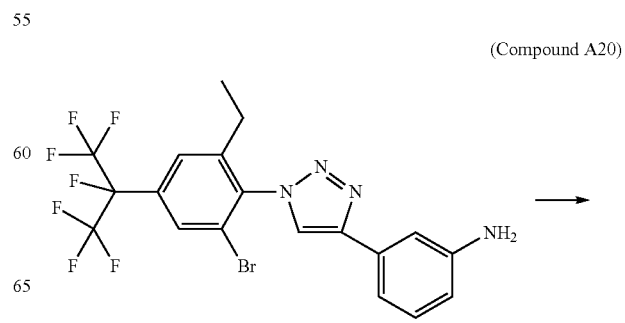

(Compound A20)

-continued

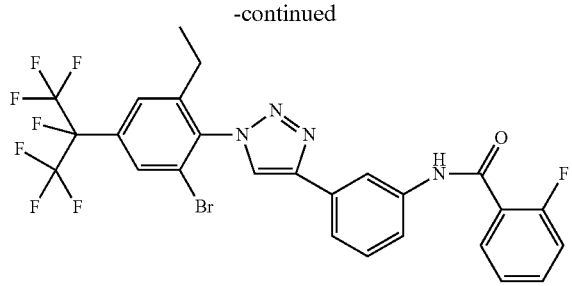

Solution A was prepared by dissolving an amino-benzamide (0.78 mmol), e.g. 3-{1-[2-Bromo-6-ethyl-4-(1,2,2,2-tetrafluoro-1-trifluoromethyl-ethyl)-phenyl]-1H-[1,2,3]triazol-4-yl}-phenylamine in the case of compound A20 of Table A, in toluene (15.6 ml). Solution B was prepared by dissolving the acid chloride (1.0 mol), e.g. 2-fluoro-benzoyl chloride in the case of compound No. A20 of Table A in toluene (8 ml).

Solution A (0.6 ml, 30 μmol) was put in a well and solution B (0.3 ml, 36 μmol) and diisopropylethylamine (Hunig's Base) (30 μl, 150 μmol) were added successively. The mixture was stirred at 70° C. for 16 hours. The mixture was diluted with a mixture of acetonitrile (0.6 ml) and N,N-dimethylacetamide (0.2 ml) and then purified by HPLC to give the desired compound.

This general method or an analogue method was used to prepare a number of compounds (Compound No. A21 to A213 of Table A, Compound No. C1 to C23 of Table C)

Method A:
LC-MS Method (positive or negative) for compounds A1 to A19, A224, A225 and B1 to B13:
ZQ Mass Spectrometer from Waters (Single quadrupole mass spectrometer) Instrument Parameter Ionisation method: Electrospray, Polarity: positive ions
Capillary (kV) 3.00, Cone (V) 30.00 (AIDA: 45V), Extractor (V) 2.00, Source Temperature (° C.) 100, Desolvation Temperature (° C.) 250, Cone Gas Flow (L/Hr) 50, Desolvation Gas Flow (L/Hr) 400, Mass range: 100 to 900 Da
HP 1100 HPLC from Agilent: solvent degasser, quaternary pump (ZCQ)/binary pump (ZDQ), heated column compartment and diode-array detector.
Column: Phenomenex Gemini C18, 3 μm particle size, 110 Angström, 30×3 mm,
Temp: 60° C., DAD Wavelength range (nm): 200 to 500
Solvent Gradient: A=water+0.05% HCOOH, B=Acetonitrile/Methanol (4:1, v:v)+0.04% HCOOH

| Time | A % | B % | Flow (ml/min) |
| --- | --- | --- | --- |
| 0.00 | 95.0 | 5.0 | 1.700 |
| 2.00 | 0.0 | 100.0 | 1.700 |
| 2.80 | 0.0 | 100.0 | 1.700 |
| 2.90 | 95.0 | 5.0 | 1.700 |
| 3.00 | 95.0 | 5.0 | 1.700 |

Method B:
LC-MS Method (positive) for compounds A20 to A42, A125 to A166:
ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150,
Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400
Method Waters ACQUITY HPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
| --- | --- | --- | --- |
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY HPLC HSS T3; Column length: 30 mm; Internal diameter of column: 2.1 mm; Particle Size: 1.8 micron; Temperature: 60° C.

Method C:
LC-MS Method (positive) for compounds A43 to A124:
ZQ Mass Spectrometer from Waters (Single quadrupole mass spectrometer)
Ionisation method: Electrospray
Polarity: positive ions
Capillary (kV) 3.00, Cone (V) 30.00, Extractor (V) 3.00, Source Temperature (° C.) 100,
Desolvation Temperature (° C.) 200, Cone Gas Flow (L/Hr) 200, Desolvation Gas Flow (L/Hr) 250
Mass range: 150 to 800 Da
DAD Wavelength range (nm): 200 to 500
The following method B was used for HPLC-MS analysis:
Method (Agilent 1100er Series) with the following HPLC gradient conditions (Solvent A: 0.1% of formic acid in water; Solvent B: 0.1% of formic acid in acetonitrile).

| Time (minutes) | A (%) | B (%) | Flow rate (ml/min) |
| --- | --- | --- | --- |
| 0 | 90 | 10 | 1.7 |
| 5.5 | 0 | 100 | 1.7 |
| 5.8 | 0 | 100 | 1.7 |
| 5.9 | 90 | 10 | 1.7 |

Type of column: Waters Atlantis dc18; Column length: 20 mm; Internal diameter of column: 3 mm; Particle Size: 3 micron; Temperature: 40° C.

Method D:
LC-MS Method (positive) for compounds C1 to C23, A167 to A212
ACQUITY SQD Mass Spectrometer from Waters (Single quadrupole mass spectrometer)
Ionisation method: Electrospray
Polarity: positive ions
Capillary (kV) 3.00, Cone (V) 20.00, Extractor (V) 3.00, Source Temperature (° C.) 150,
Desolvation Temperature (° C.) 400, Cone Gas Flow (L/Hr) 60, Desolvation Gas Flow (L/Hr) 700
Mass range: 100 to 800 Da
DAD Wavelength range (nm): 210 to 400

Method Waters ACQUITY HPLC with the following HPLC gradient conditions
(Solvent A: Water/Methanol 9:1, 0.1% formic acid and Solvent B: Acetonitrile, 0.1% formic acid)

| Time (minutes) | A (%) | B (%) | Flow rate (ml/min) |
|---|---|---|---|
| 0 | 100 | 0 | 0.75 |
| 2.5 | 0 | 100 | 0.75 |

-continued

| Time (minutes) | A (%) | B (%) | Flow rate (ml/min) |
|---|---|---|---|
| 2.8 | 0 | 100 | 0.75 |
| 3.0 | 100 | 0 | 0.75 |

Type of column: Waters ACQUITY HPLC BEH C18; Column length: 50 mm; Internal diameter of column: 2.1 mm; Particle Size: 1.7 micron; Temperature: 60° C.

TABLE A

Compounds of formula (Ie): $R^2$ = H and $A^4$ = CH

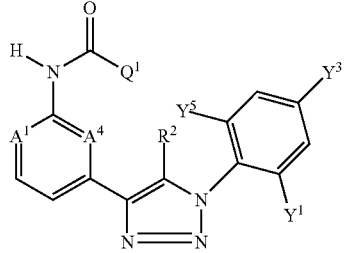

(Ie)

| Ex. | $Q^1$ | $Y^3$ | $Y^1$ | $Y^5$ | $A^1$ | RT (min) | $MH^+$ | $M - H^-$ | MP° C. |
|---|---|---|---|---|---|---|---|---|---|
| A1 | 4-cyanophenyl | nonafluoro-but-2-yl | Cl | Cl | CH | 2.15 | 652 | — | |
| A2 | 2-chloro-4-fluorophenyl | nonafluoro-but-2-yl | Cl | Cl | CH | 2.19 | 680 | — | |
| A3 | 4-fluorophenyl | nonafluoro-but-2-yl | Cl | Cl | CH | 2.18 | 645 | — | |
| A4 | 2-fluorophenyl | nonafluoro-but-2-yl | Cl | Cl | CH | 2.18 | 645 | — | |
| A5 | 2-chloro-pyridin-3-yl | nonafluoro-but-2-yl | Cl | Cl | CH | 2.11 | 663 | — | |
| A6 | 2-methyl-phenyl | nonafluoro-but-2-yl | Cl | Cl | CH | 2.18 | 643 | — | |
| A7 | 2-methyl-4-fluorophenyl | nonafluoro-but-2-yl | Cl | Cl | CH | 2.19 | 661 | — | |
| A8 | 2-methyl-3-nitrophenyl | nonafluoro-but-2-yl | Cl | Cl | CH | 2.17 | 688 | — | |
| A9 | 2-fluorophenyl | nonafluoro-but-2-yl | Me | Et | CH | 2.2 | 619 | — | |
| A10 | 4-fluorophenyl | nonafluoro-but-2-yl | Me | Et | CH | 2.22 | 619 | — | |
| A11 | 2-chloro-4-fluorophenyl | nonafluoro-but-2-yl | Me | Et | CH | 2.22 | 653 | — | |
| A12 | 2-methyl-phenyl | nonafluoro-but-2-yl | Me | Et | CH | 2.22 | 615 | — | |
| A13 | 2-fluorophenyl | heptafluoro-prop-2-yl | Me | Br | CH | 2.14 | 621 | — | |
| A14 | 4-fluorophenyl | heptafluoro-prop-2-yl | Me | Br | CH | 2.14 | 621 | — | |
| A15 | 2-chloro-4-fluorophenyl | heptafluoro-prop-2-yl | Me | Br | CH | 2.15 | 655 | — | |
| A16 | 2-methyl-phenyl | heptafluoro-prop-2-yl | Me | Br | CH | 2.15 | 617 | — | |
| A17 | 2-chloro-4-fluorophenyl | heptafluoro-prop-2-yl | Cl | Cl | CH | 2.15 | 631 | — | |
| A18 | 1,4,6-trifluoro-phenyl | heptafluoro-prop-2-yl | Cl | Cl | C—F | 2.18 | — | 697 | |
| A19 | 2-methyl-4-cyanophenyl | heptafluoro-prop-2-yl | Cl | Cl | C—CN | 2.16 | — | 689 | |
| A20 | 2-fluorophenyl | heptafluoro-prop 2-yl | Et | Br | CH | 2.14 | 633.14 | | |
| A21 | 2-methylphenyl | heptafluoro-prop 2-yl | Et | Br | CH | 2.15 | 629.19 | | |
| A22 | 2-chloro-phenyl | heptafluoro-prop 2-yl | Et | Br | CH | 2.13 | 649.13 | | |
| A23 | 4-cyanophenyl | heptafluoro-prop 2-yl | Et | Br | CH | 2.07 | 640.22 | | |

TABLE A-continued

Compounds of formula (Ie): $R^2$ = H and $A^4$ = CH (Ie)

| Ex. | $Q^1$ | $Y^3$ | $Y^1$ | $Y^5$ | $A^1$ | RT (min) | $MH^+$ | $M - H^-$ | MP° C. |
|---|---|---|---|---|---|---|---|---|---|
| A24 | 4-nitrophenyl | heptafluoro-prop 2-yl | Et | Br | CH | 2.12 | 660.22 | | |
| A25 | 4-methylphenyl | heptafluoro-prop 2-yl | Et | Br | CH | 2.17 | 628.66 | | |
| A26 | 2-methyl-4-fluorophenyl | heptafluoro-prop 2-yl | Et | Br | CH | 2.16 | 647.49 | | |
| A27 | 2-fluoro-5-chloro-Phenyl | heptafluoro-prop 2-yl | Et | Br | CH | 2.23 | 667.12 | | |
| A28 | 4-nitro-2-chloro-Phenyl | heptafluoro-prop 2-yl | Et | Br | CH | 2.14 | 694.15 | | |
| A29 | furanyl | heptafluoro-prop 2-yl | Et | Br | CH | 2.02 | 605.16 | | |
| A30 | 4-trifluoromethoxy-Phenyl | heptafluoro-prop 2-yl | Et | Br | CH | 2.26 | 699.13 | | |
| A31 | 3-4-fluoro-Phenyl | heptafluoro-prop-2-yl | Et | Br | CH | 2.26 | 701.22 | | |
| A32 | 3-trifluoromethyl-Phenyl | heptafluoro-prop 2-yl | Et | Br | CH | 2.24 | 683 | | |
| A33 | 2-trifluoromethoxy-Phenyl | heptafluoro-prop 2-yl | Et | Br | CH | 2.19 | 699.23 | | |
| A34 | 2-methoxy-Phenyl | heptafluoro-prop 2-yl | Et | Br | CH | 2.2 | 644.57 | | |
| A35 | Phenyl | heptafluoro-prop 2-yl | Et | Br | CH | 2.11 | 615.11 | | |
| A36 | 4-fluoro-Phenyl | heptafluoro-prop 2-yl | Et | Br | CH | 2.13 | 633.18 | | |
| A37 | 2-trifluoromethyl-Phenyl | heptafluoro-prop 2-yl | Et | Br | CH | 2.13 | 682.95 | | |
| A38 | 4-fluoro-2-chloro-Phenyl | heptafluoro-prop 2-yl | Et | Br | CH | 2.15 | 667.17 | | |
| A39 | 4-Methyl-[1,2,3]thiadiazole | heptafluoro-prop 2-yl | Et | Br | CH | 2.05 | 636.79 | | |
| A40 | 2,3-difluoro-Phenyl | heptafluoro-prop 2-yl | Et | Br | CH | 2.15 | 651.23 | | |
| A41 | 2,4-difluoro-Phenyl | heptafluoro-prop 2-yl | Et | Br | CH | 2.15 | 651.2 | | |
| A42 | 2-fluoro-5-trifluoromethyl-Phenyl | heptafluoro-prop 2-yl | Et | Br | CH | 2.25 | 701.18 | | |
| A43 | 2-chloro-phenyl | nonafluoro-but-2-yl | Cl | Cl | CH | 4.47 | 661.2 | | |
| A44 | 4-nitrophenyl | nonafluoro-but-2-yl | Cl | Cl | CH | 4.45 | 672.2 | | |
| A45 | 4-methylphenyl | nonafluoro-but-2-yl | Cl | Cl | CH | 4.61 | 641.25 | | |
| A46 | 2-fluoro-5-chloro-Phenyl | nonafluoro-but-2-yl | Cl | Cl | CH | 4.8 | 679.15 | | |
| A47 | 4-nitro-2-chloro-Phenyl | nonafluoro-but-2-yl | Cl | Cl | CH | 4.58 | 706.18 | | |
| A48 | furanyl | nonafluoro-but-2-yl | Cl | Cl | CH | 4.27 | 617.2 | | |
| A49 | 4-trifluoromethoxy-Phenyl | nonafluoro-but-2-yl | Cl | Cl | CH | 4.74 | 711.17 | | |
| A50 | 3-trifluoromethyl-4-fluoro-Phenyl | nonafluoro-but-2-yl | Cl | Cl | CH | 4.7 | 713.19 | | |

TABLE A-continued

Compounds of formula (Ie): $R^2$ = H and $A^4$ = CH (Ie)

| Ex. | $Q^1$ | $Y^3$ | $Y^1$ | $Y^5$ | $A^1$ | RT (min) | $MH^+$ | $M - H^-$ | MP° C. |
|---|---|---|---|---|---|---|---|---|---|
| A51 | 3-trifluoromethyl-Phenyl | nonafluoro-but-2-yl | Cl | Cl | CH | 4.72 | 695.2 | | |
| A52 | 2-trifluoromethyl-Phenyl | nonafluoro-but-2-yl | Cl | Cl | CH | 4.64 | 711.2 | | |
| A53 | 2-methoxy-Phenyl | nonafluoro-but-2-yl | Cl | Cl | CH | 4.66 | 657.24 | | |
| A54 | Phenyl | nonafluoro-but-2-yl | Cl | Cl | CH | 4.47 | 627.23 | | |
| A55 | 2-trifluoromethyl-Phenyl | nonafluoro-but-2-yl | Cl | Cl | CH | 4.45 | 695.2 | | |
| A56 | 4-Methyl-[1,2,3]thiadiazole | nonafluoro-but-2-yl | Cl | Cl | CH | 4.31 | 649.2 | | |
| A57 | 2,3-difluoro-Phenyl | nonafluoro-but-2-yl | Cl | Cl | CH | 4.55 | 663.2 | | |
| A58 | 2,4-difluoro-Phenyl | nonafluoro-but-2-yl | Cl | Cl | CH | 4.55 | 663.2 | | |
| A59 | 2-fluoro-5-trifluoromethyl-Phenyl | nonafluoro-but-2-yl | Cl | Cl | CH | 4.74 | 713.2 | | |
| A60 | 2-fluoro-phenyl | nonafluoro-but-2-yl | Et | Br | CH | 4.6 | 683.2 | | |
| A61 | 2-methylphenyl | nonafluoro-but-2-yl | Et | Br | CH | 4.62 | 679.2 | | |
| A62 | 2-chloro-phenyl | nonafluoro-but-2-yl | Et | Br | CH | 4.68 | 699.2 | | |
| A63 | 4-cyanophenyl | nonafluoro-but-2-yl | Et | Br | CH | 4.51 | 690.2 | | |
| A64 | 4-nitrophenyl | nonafluoro-but-2-yl | Et | Br | CH | 4.68 | 710.2 | | |
| A65 | 4-methylphenyl | nonafluoro-but-2-yl | Et | Br | CH | 4.7 | 679.2 | | |
| A66 | 2-methyl-4-fluorophenyl | nonafluoro-but-2-yl | Et | Br | CH | 4.7 | 697.2 | | |
| A67 | 2-fluoro-5-chloro-Phenyl | nonafluoro-but-2-yl | Et | Br | CH | 4.82 | 717.2 | | |
| A68 | 4-nitro-2-chloro-Phenyl | nonafluoro-but-2-yl | Et | Br | CH | 4.72 | 744.2 | | |
| A69 | furanyl | nonafluoro-but-2-yl | Et | Br | CH | 4.41 | 655.2 | | |
| A70 | 4-trifluoromethoxy-Phenyl | nonafluoro-but-2-yl | Et | Br | CH | 4.9 | 749.2 | | |
| A71 | 3-trifluoromethyl-4-fluoro-Phenyl | nonafluoro-but-2-yl | Et | Br | CH | 4.9 | 751.2 | | |
| A72 | 3-trifluoromethyl-Phenyl | nonafluoro-but-2-yl | Et | Br | CH | 4.84 | 733.2 | | |
| A73 | 2-trifluoromethoxy-Phenyl | nonafluoro-but-2-yl | Et | Br | CH | 4.69 | 749.1 | | |
| A74 | 2-methoxy-Phenyl | nonafluoro-but-2-yl | Et | Br | CH | 4.76 | 695.3 | | |
| A75 | Phenyl | nonafluoro-but-2-yl | Et | Br | CH | 4.55 | 664.2 | | |
| A76 | 4-fluoro-Phenyl | nonafluoro-but-2-yl | Et | Br | CH | 4.62 | 683.24 | | |

TABLE A-continued

Compounds of formula (Ie): $R^2$ = H and $A^4$ = CH (Ie)

| Ex. | $Q^1$ | $Y^3$ | $Y^1$ | $Y^5$ | $A^1$ | RT (min) | $MH^+$ | $M - H^-$ | MP° C. |
|---|---|---|---|---|---|---|---|---|---|
| A77 | 2-trifluoromethyl-Phenyl | nonafluoro-but-2-yl | Et | Br | CH | 4.66 | 733.2 | | |
| A78 | 4-fluoro-2-chloro-Phenyl | nonafluoro-but-2-yl | Et | Br | CH | 4.74 | 717.2 | | |
| A79 | 4-Methyl-[1,2,3]thiadiazole | nonafluoro-but-2-yl | Et | Br | CH | 4.49 | 687.2 | | |
| A80 | 2,3-difluoro-Phenyl | nonafluoro-but-2-yl | Et | Br | CH | 4.66 | 701.2 | | |
| A81 | 2,4-difluoro-Phenyl | nonafluoro-but-2-yl | Et | Br | CH | 4.7 | 701.2 | | |
| A82 | 2-fluoro-5-trifluoromethyl-Phenyl | nonafluoro-but-2-yl | Et | Br | CH | 4.88 | 751.2 | | |
| A83 | 2-chloro-phenyl | heptafluoro-prop 2-yl | Me | Br | CH | 4.37 | 635.2 | | |
| A84 | 4-cyanophenyl | heptafluoro-prop 2-yl | Me | Br | CH | 4.29 | 626.2 | | |
| A85 | 4-nitrophenyl | heptafluoro-prop 2-yl | Me | Br | CH | 4.49 | 646.2 | | |
| A86 | 4-methylphenyl | heptafluoro-prop 2-yl | Me | Br | CH | 4.45 | 615.3 | | |
| A87 | 2-methyl-4-fluorophenyl | heptafluoro-prop 2-yl | Me | Br | CH | 4.43 | 633.3 | | |
| A88 | 2-fluoro-5-chloro-Phenyl | heptafluoro-prop 2-yl | Me | Br | CH | 4.61 | 653.1 | | |
| A89 | 4-nitro-2-chloro-Phenyl | heptafluoro-prop 2-yl | Me | Br | CH | 4.44 | 680.2 | | |
| A90 | furanyl | heptafluoro-prop 2-yl | Me | Br | CH | 4.17 | 591.2 | | |
| A91 | 4-trifluoromethoxy-Phenyl | heptafluoro-prop 2-yl | Me | Br | CH | 4.68 | 685.2 | | |
| A92 | 3-trifluoromethyl-4-fluoro-Phenyl | heptafluoro-prop 2-yl | Me | Br | CH | 4.74 | 687.2 | | |
| A93 | 3-trifluoromethyl-Phenyl | heptafluoro-prop 2-yl | Me | Br | CH | 4.6 | 669.2 | | |
| A94 | 2-trifluoromethoxy-Phenyl | heptafluoro-prop 2-yl | Me | Br | CH | 4.49 | 685.2 | | |
| A95 | 2-methoxy-Phenyl | heptafluoro-prop 2-yl | Me | Br | CH | 4.49 | 631.2 | | |
| A96 | Phenyl | heptafluoro-prop 2-yl | Me | Br | CH | 4.29 | 601.2 | | |
| A97 | 2-trifluoromethyl-Phenyl | heptafluoro-prop 2-yl | Me | Br | CH | 4.37 | 669.2 | | |
| A98 | 4-Methyl-[1,2,3]thiadiazole | heptafluoro-prop 2-yl | Me | Br | CH | 4.17 | 623.2 | | |
| A99 | 2,3-difluoro-Phenyl | heptafluoro-prop 2-yl | Me | Br | CH | 4.39 | 637.2 | | |
| A100 | 2,4-difluoro-Phenyl | heptafluoro-prop 2-yl | Me | Br | CH | 4.41 | 637.2 | | |
| A101 | 2-fluoro-5-trifluoromethyl-Phenyl | heptafluoro-prop 2-yl | Me | Br | CH | 4.6 | 687.2 | | |
| A102 | 2-fluorophenyl | nonafluoro-but-2-yl | Me | Br | CH | 4.53 | 669.2 | | |

TABLE A-continued

Compounds of formula (Ie): $R^2$ = H and $A^4$ = CH (Ie)

| Ex. | $Q^1$ | $Y^3$ | $Y^1$ | $Y^5$ | $A^1$ | RT (min) | $MH^+$ | $M - H^-$ | MP° C. |
|---|---|---|---|---|---|---|---|---|---|
| A103 | 2-methylphenyl | nonafluoro-but-2-yl | Me | Br | CH | 4.55 | 665.2 | | |
| A104 | 2-chloro-phenyl | nonafluoro-but-2-yl | Me | Br | CH | 4.49 | 685.16 | | |
| A105 | 4-cyanophenyl | nonafluoro-but-2-yl | Me | Br | CH | 4.41 | 676.2 | | |
| A106 | 4-nitrophenyl | nonafluoro-but-2-yl | Me | Br | CH | 4.47 | 696.2 | | |
| A107 | 4-methylphenyl | nonafluoro-but-2-yl | Me | Br | CH | 4.58 | 665.2 | | |
| A108 | 2-methyl-4-fluorophenyl | nonafluoro-but-2-yl | Me | Br | CH | 4.55 | 683.2 | | |
| A109 | 2-fluoro-5-chloro-Phenyl | nonafluoro-but-2-yl | Me | Br | CH | 4.72 | 703.14 | | |
| A110 | 4-nitro-2-chloro-Phenyl | nonafluoro-but-2-yl | Me | Br | CH | 4.66 | 730.12 | | |
| A111 | furanyl | nonafluoro-but-2-yl | Me | Br | CH | 4.33 | 641.2 | | |
| A112 | 4-trifluoromethoxy-Phenyl | nonafluoro-but-2-yl | Me | Br | CH | 4.78 | 735.2 | | |
| A113 | 3-trifluoromethyl-4-fluoro-Phenyl | nonafluoro-but-2-yl | Me | Br | CH | 4.84 | 737.1 | | |
| A114 | 3-trifluoromethyl-Phenyl | nonafluoro-but-2-yl | Me | Br | CH | 4.74 | 719.2 | | |
| A115 | 2-trifluoromethoxy-Phenyl | nonafluoro-but-2-yl | Me | Br | CH | 4.66 | 735.2 | | |
| A116 | 2-methoxy-Phenyl | nonafluoro-but-2-yl | Me | Br | CH | 4.64 | 681.2 | | |
| A117 | Phenyl | nonafluoro-but-2-yl | Me | Br | CH | 4.45 | 651.2 | | |
| A118 | 4-fluoro-Phenyl | nonafluoro-but-2-yl | Me | Br | CH | 4.51 | 669.2 | | |
| A119 | 2-trifluoromethyl-Phenyl | nonafluoro-but-2-yl | Me | Br | CH | 4.53 | 719.1 | | |
| A120 | 4-fluoro-2-chloro-Phenyl | nonafluoro-but-2-yl | Me | Br | CH | 4.6 | 703.1 | | |
| A121 | 4-Methyl-[1,2,3]thiadiazole | nonafluoro-but-2-yl | Me | Br | CH | 4.37 | 673.1 | | |
| A122 | 2,3-difluoro-Phenyl | nonafluoro-but-2-yl | Me | Br | CH | 4.6 | 687.1 | | |
| A123 | 2,4-difluoro-Phenyl | nonafluoro-but-2-yl | Me | Br | CH | 4.64 | 687.1 | | |
| A124 | 2-fluoro-5-trifluoromethyl-Phenyl | nonafluoro-but-2-yl | Me | Br | CH | 4.86 | 737.2 | | |
| A125 | 2-chloro-phenyl | nonafluoro-but-2-yl | Me | Et | CH | 2.18 | 635.37 | | |
| A126 | 4-cyanophenyl | nonafluoro-but-2-yl | Me | Et | CH | 2.12 | 626.32 | | |
| A127 | 4-nitrophenyl | nonafluoro-but-2-yl | Me | Et | CH | 2.17 | 646.41 | | |
| A128 | 4-methylphenyl | nonafluoro-but-2-yl | Me | Et | CH | 2.22 | 615.4 | | |
| A129 | 2-methyl-4-fluorophenyl | nonafluoro-but-2-yl | Me | Et | CH | 2.21 | 633.33 | | |

TABLE A-continued

Compounds of formula (Ie): $R^2$ = H and $A^4$ = CH

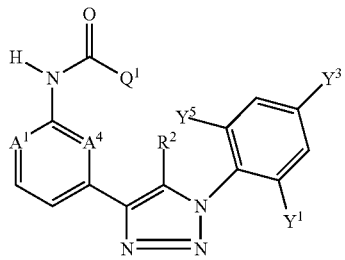

(Ie)

| Ex. | $Q^1$ | $Y^3$ | $Y^1$ | $Y^5$ | $A^1$ | RT (min) | MH+ | M − H− | MP° C. |
|---|---|---|---|---|---|---|---|---|---|
| A130 | 2-fluoro-5-chloro-Phenyl | nonafluoro-but-2-yl | Me | Et | CH | 2.28 | 653.4 | | |
| A131 | 4-nitro-2-chloro-Phenyl | nonafluoro-but-2-yl | Me | Et | CH | 2.19 | 679.63 | | |
| A132 | furanyl | nonafluoro-but-2-yl | Me | Et | CH | 2.08 | 590.75 | | |
| A133 | 4-trifluoromethoxy-Phenyl | nonafluoro-but-2-yl | Me | Et | CH | 2.3 | 685.38 | | |
| A134 | 3-trifluoromethyl-4-fluoro-Phenyl | nonafluoro-but-2-yl | Me | Et | CH | 2.31 | 687.31 | | |
| A135 | 3-trifluoromethyl-Phenyl | nonafluoro-but-2-yl | Me | Et | CH | 2.28 | 669.35 | | |
| A136 | 2-trifluoromethoxy-Phenyl | nonafluoro-but-2-yl | Me | Et | CH | 2.24 | 685.4 | | |
| A137 | 2-methoxy-Phenyl | nonafluoro-but-2-yl | Me | Et | CH | 2.25 | 631.38 | | |
| A138 | Phenyl | nonafluoro-but-2-yl | Me | Et | CH | 2.16 | 601.39 | | |
| A139 | 2-trifluoromethyl-Phenyl | nonafluoro-but-2-yl | Me | Et | CH | 2.19 | 669.34 | | |
| A140 | 4-Methyl-[1,2,3]thiadiazole | nonafluoro-but-2-yl | Me | Et | CH | 2.11 | 623.46 | | |
| A141 | 2,3-difluoro-Phenyl | nonafluoro-but-2-yl | Me | Et | CH | 2.2 | 636.76 | | |
| A142 | 2,4-difluoro-Phenyl | nonafluoro-but-2-yl | Me | Et | CH | 2.21 | 637.43 | | |
| A143 | 2-fluoro-5-trifluoromethyl-Phenyl | nonafluoro-but-2-yl | Me | Et | CH | 2.29 | 686.78 | | |
| A144 | 2-fluorophenyl | heptafluoro-prop 2-yl | Cl | Cl | C—CN | 2.1 | 619.99 | | |
| A145 | 2-methylphenyl | heptafluoro-prop 2-yl | Cl | Cl | C—CN | 2.06 | 616.19 | | |
| A146 | 2-chloro-phenyl | heptafluoro-prop 2-yl | Cl | Cl | C—CN | 2.05 | 636.15 | | |
| A147 | 4-cyanophenyl | heptafluoro-prop 2-yl | Cl | Cl | C—CN | 1.96 | 627.26 | | |
| A148 | 4-nitrophenyl | heptafluoro-prop 2-yl | Cl | Cl | C—CN | 2.01 | 647.27 | | |
| A149 | 4-methylphenyl | heptafluoro-prop 2-yl | Cl | Cl | C—CN | 2.1 | 616.27 | | |
| A150 | 2-methyl-4-fluorophenyl | heptafluoro-prop 2-yl | Cl | Cl | C—CN | 2.07 | 634.2 | | |
| A151 | 2-fluoro-5-chloro-Phenyl | heptafluoro-prop 2-yl | Cl | Cl | C—CN | 2.19 | 654.14 | | |
| A152 | 4-nitro-2-chloro-Phenyl | heptafluoro-prop 2-yl | Cl | Cl | C—CN | 2.05 | 680.72 | | |
| A153 | furanyl | heptafluoro-prop 2-yl | Cl | Cl | C—CN | 1.96 | 592.14 | | |
| A154 | 4-trifluoromethoxy-Phenyl | heptafluoro-prop 2-yl | Cl | Cl | C—CN | 2.16 | 685.62 | | |
| A155 | 3-trifluoromethyl-4-fluoro-Phenyl | heptafluoro-prop 2-yl | Cl | Cl | C—CN | 2.15 | 688.18 | | |

TABLE A-continued

Compounds of formula (Ie): $R^2$ = H and $A^4$ = CH (Ie)

| Ex. | $Q^1$ | $Y^3$ | $Y^1$ | $Y^5$ | $A^1$ | RT (min) | $MH^+$ | $M - H^-$ | MP° C. |
|---|---|---|---|---|---|---|---|---|---|
| A156 | 3-trifluoromethyl-Phenyl | heptafluoro-prop 2-yl | Cl | Cl | C—CN | 2.13 | 670.19 | | |
| A157 | 2-trifluoromethoxy-Phenyl | heptafluoro-prop 2-yl | Cl | Cl | C—CN | 2.12 | 686.19 | | |
| A158 | 2-methoxy-Phenyl | heptafluoro-prop 2-yl | Cl | Cl | C—CN | 2.28 | 632.27 | | |
| A159 | Phenyl | heptafluoro-prop 2-yl | Cl | Cl | C—CN | 2.02 | 602.05 | | |
| A160 | 4-fluoro-Phenyl | heptafluoro-prop 2-yl | Cl | Cl | C—CN | 2.03 | 620.18 | | |
| A161 | 2-trifluoromethyl-Phenyl | heptafluoro-prop 2-yl | Cl | Cl | C—CN | 2.06 | 670.18 | | |
| A162 | 4-fluoro-2-chloro-Phenyl | heptafluoro-prop 2-yl | Cl | Cl | C—CN | 2.08 | 654.2 | | |
| A163 | 4-Methyl-[1,2,3]thiadiazole | heptafluoro-prop 2-yl | Cl | Cl | C—CN | 1.94 | 624.26 | | |
| A164 | 2,3-difluoro-Phenyl | heptafluoro-prop 2-yl | Cl | Cl | C—CN | 2.09 | 638.22 | | |
| A165 | 2,4-difluoro-Phenyl | heptafluoro-prop 2-yl | Cl | Cl | C—CN | 2.12 | 637.79 | | |
| A166 | 2-fluoro-5-trifluoromethyl-Phenyl | heptafluoro-prop 2-yl | Cl | Cl | C—CN | 2.19 | 688.2 | | |
| A167 | 2-fluorophenyl | nonafluoro-but-2-yl | Cl | Cl | C—F | 2.22 | 663.12 | | |
| A168 | 2-methylphenyl | nonafluoro-but-2-yl | Cl | Cl | C—F | 2.18 | 659.13 | | |
| A169 | 2-chloro-phenyl | nonafluoro-but-2-yl | Cl | Cl | C—F | 2.17 | 679.09 | | |
| A170 | 4-cyanophenyl | nonafluoro-but-2-yl | Cl | Cl | C—F | 2.08 | 670.09 | | |
| A171 | 4-nitrophenyl | nonafluoro-but-2-yl | Cl | Cl | C—F | 2.12 | 690.09 | | |
| A172 | 4-methylphenyl | nonafluoro-but-2-yl | Cl | Cl | C—F | 2.2 | 659.13 | | |
| A173 | 2-methyl-4-fluorophenyl | nonafluoro-but-2-yl | Cl | Cl | C—F | 2.19 | 677.13 | | |
| A174 | 2-fluoro-5-chloro-Phenyl | nonafluoro-but-2-yl | Cl | Cl | C—F | 2.3 | 697.07 | | |
| A175 | 2-chloro-4-nitrophenyl | nonafluoro-but-2-yl | Cl | Cl | C—F | 2.17 | 724.05 | | |
| A176 | furanyl | nonafluoro-but-2-yl | Cl | Cl | C—F | 2.08 | 635.14 | | |
| A177 | 4-trifluoromethoxy-Phenyl | nonafluoro-but-2-yl | Cl | Cl | C—F | 2.27 | 728.96 | | |
| A178 | 3-trifluoromethyl-4-fluoro-Phenyl | nonafluoro-but-2-yl | Cl | Cl | C—F | 2.26 | 731.19 | | |
| A179 | 3-trifluoromethyl-Phenyl | nonafluoro-but-2-yl | Cl | Cl | C—F | 2.24 | 713.09 | | |
| A180 | 2-trifluoromethoxy-Phenyl | nonafluoro-but-2-yl | Cl | Cl | C—F | 2.25 | 729.08 | | |
| A181 | 2-methoxy-Phenyl | nonafluoro-but-2-yl | Cl | Cl | C—F | 2.3 | 675.07 | | |

TABLE A-continued

Compounds of formula (Ie): $R^2$ = H and $A^4$ = CH (Ie)

| Ex. | $Q^1$ | $Y^3$ | $Y^1$ | $Y^5$ | $A^1$ | RT (min) | $MH^+$ | $M - H^-$ | MP° C. |
|---|---|---|---|---|---|---|---|---|---|
| A182 | Phenyl | nonafluoro-but-2-yl | Cl | Cl | C—F | 2.13 | 645.11 | | |
| A183 | 4-Fluoro-Phenyl | nonafluoro-but-2-yl | Cl | Cl | C—F | 2.14 | 663 | | |
| A184 | 2-trifluoromethyl-Phenyl | nonafluoro-but-2-yl | Cl | Cl | C—F | 2.17 | 713.02 | | |
| A185 | 4-fluoro-2-chloro-Phenyl | nonafluoro-but-2-yl | Cl | Cl | C—F | 2.2 | 697.26 | | |
| A186 | 4-Methyl-[1,2,3]thiadiazole | nonafluoro-but-2-yl | Cl | Cl | C—F | 2.07 | 667.08 | | |
| A187 | 2,3-difluoro-Phenyl | nonfluoro-but-2-yl | Cl | Cl | C—F | 2.21 | 681.09 | | |
| A188 | 2,4-difluoro-Phenyl | nonafluoro-but-2-yl | Cl | Cl | C—F | 2.23 | 681.26 | | |
| A189 | 2-fluoro-5-trifluoromethyl-Phenyl | nonafluoro-but-2-yl | Cl | Cl | C—F | 2.29 | 731.31 | | |
| A190 | 2-fluorophenyl | nonafluoro-but-2-yl | Cl | Cl | C—CN | 2.17 | 670.14 | | |
| A191 | 2-methylphenyl | nonafluoro-but-2-yl | Cl | Cl | C—CN | 2.14 | 666.14 | | |
| A192 | 2-chloro-phenyl | nonafluoro-but-2-yl | Cl | Cl | C—CN | 2.13 | 686.06 | | |
| A193 | 4-cyanophenyl | nonafluoro-but-2-yl | Cl | Cl | C—CN | 2.04 | 677.15 | | |
| A194 | 4-nitrophenyl | nonfluoro-but-2-yl | Cl | Cl | C—CN | 2.08 | 697.21 | | |
| A195 | 4-methylphenyl | nonafluoro-but-2-yl | Cl | Cl | C—CN | 2.16 | 666.17 | | |
| A196 | 2-methyl-4-fluorophenyl | nonafluoro-but-2-yl | Cl | Cl | C—CN | 2.15 | 684.13 | | |
| A197 | 2-fluoro-5-chloro-Phenyl | nonafluoro-but-2-yl | Cl | Cl | C—CN | 2.25 | 704.05 | | |
| A198 | 2-chloro-4-nitrophenyl | nonafluoro-but-2-yl | Cl | Cl | C—CN | 2.13 | 731.11 | | |
| A199 | furanyl | nonafluoro-but-2-yl | Cl | Cl | C—CN | 2.04 | 642.1 | | |
| A200 | 4-trifluoromethoxy-Phenyl | nonafluoro-but-2-yl | Cl | Cl | C—CN | 2.23 | 736.13 | | |
| A201 | 3-trifluoromethyl-4-fluoro-Phenyl | nonafluoro-but-2-yl | Cl | Cl | C—CN | 2.22 | 738.12 | | |
| A202 | 4-trifluoromethyl-Phenyl | nonafluoro-but-2-yl | Cl | Cl | C—CN | 2.2 | 720.13 | | |
| A203 | 2-trifluoromethoxy-Phenyl | nonafluoro-but-2-yl | Cl | Cl | C—CN | 2.2 | 736.12 | | |
| A204 | 2-methoxy-Phenyl | nonafluoro-but-2-yl | Cl | Cl | C—CN | 2.32 | 682.15 | | |
| A205 | Phenyl | nonafluoro-but-2-yl | Cl | Cl | C—CN | 2.1 | 652.13 | | |
| A206 | 4-fluoro-Phenyl | nonafluoro-but-2-yl | Cl | Cl | C—CN | 2.11 | 670.1 | | |
| A207 | 2-trifluoromethyl-Phenyl | nonafluoro-but-2-yl | Cl | Cl | C—CN | 2.14 | 720.11 | | |
| A208 | 4-fluoro-2-chloro-Phenyl | nonafluoro-but-2-yl | Cl | Cl | C—CN | 2.15 | 704.11 | | |

TABLE A-continued

Compounds of formula (Ie): $R^2$ = H and $A^4$ = CH (Ie)

| Ex. | $Q^1$ | $Y^3$ | $Y^1$ | $Y^5$ | $A^1$ | RT (min) | MH+ | M – H− | MP° C. |
|---|---|---|---|---|---|---|---|---|---|
| A209 | 4-Methyl-[1,2,3]thiadiazole | nonafluoro-but-2-yl | Cl | Cl | C—CN | 2.03 | 674.09 | | |
| A210 | 2,3-difluoro-Phenyl | nonafluoro-but-2-yl | Cl | Cl | C—CN | 2.15 | 688.11 | | |
| A211 | 2,4-difluoro-Phenyl | nonafluoro-but-2-yl | Cl | Cl | C—CN | 2.18 | 688.1 | | |
| A212 | 2-fluoro-5-trifluoromethyl-Phenyl | nonafluoro-but-2-yl | Cl | Cl | C—CN | 2.26 | 738.1 | | |
| A213 | 2,4,6-trifluoro-Phenyl | heptafluoro-prop 2-yl | Cl | Cl | C—F | | | | 206 |
| A214 | 4-fluoro-Phenyl | heptafluoro-prop 2-yl | Cl | Cl | CH | | | | 164 |
| A215 | 2-methyl-Phenyl | heptafluoro-prop 2-yl | Cl | Cl | CH | | | | 119 |
| A216 | 4-cyano-Phenyl | heptafluoro-prop 2-yl | Cl | Cl | CH | | | | 142 |
| A217 | 2-methyl-4-fluoro-Phenyl | heptafluoro-prop 2-yl | Cl | Cl | CH | | | | 115 |
| A218 | 2-methyl-3-nitro-Phenyl | heptafluoro-prop 2-yl | Cl | Cl | CH | | | | 128 |
| A219 | 2-chloro-pyridin-3-yl | heptafluoro-prop 2-yl | Cl | Cl | CH | | | | 228 |
| A220 | 2-methyl-4-cyano-Phenyl | heptafluoro-prop 2-yl | Cl | Cl | C—CN | | | | 213 |
| A221 | 2-methyl-3-nitro Phenyl | nonafluoro-but-2-yl | Et | Br | CH | | | | 207 |
| A222 | 2-methyl-3-nitro-Phenyl | nonafluoro-but-2-yl | Me | Br | CH | | | | 155 |
| A223 | 2-chloro-pyridin-3-yl | nonafluoro-but-2-yl | Me | Br | CH | | | | 191 |
| A224 | 4-fluoro-2-chloro-Phenyl | trifluoromethyl | Cl | Cl | CH | 2.06 | 531 | | |
| A225 | 4-cyano-Phenyl | trifluoromethyl | Cl | Cl | CH | 2.00 | 502 | | |

TABLE B

Compound of formula (Ig): $R^2$ = H (Id)

| Compound No. | $Y^3$ | $Y^1$ | $Y^5$ | $A^1$ | $A^4$ | RT (min) | MH+ | MP° C. |
|---|---|---|---|---|---|---|---|---|
| B1 | nonafluoro-but-2-yl | Cl | Cl | CH | CH | 2.01 | 523 | |
| B2 | heptafluoro-prop-2-yl | Me | Br | CH | CH | 1.94 | 499 | |
| B3 | heptafluoro-prop-2-yl | Cl | Cl | CH | CH | 1.94 | 473 | |
| B4 | nonafluoro-but-2-yl | Me | Et | CH | CH | 2.05 | 497 | |

TABLE B-continued

Compound of formula (Ig): $R^2 = H$ (Id)

| Compound No. | $Y^3$ | $Y^1$ | $Y^5$ | $A^1$ | $A^4$ | RT (min) | MH+ | MP° C. |
|---|---|---|---|---|---|---|---|---|
| B5 | nonafluoro-but-2-yl | Cl | Cl | C—F | CH | 2.09 | 541 | |
| B6 | nonafluoro-but-2-yl | Cl | Cl | C—CN | CH | 2.08 | 548 | |
| B7 | heptafluoro-prop-2-yl | Me | H | CH | CH | | | 124 |
| B8 | heptafluoro-prop-2-yl | Et | Br | CH | CH | 2.02 | 513 | |
| B9 | nonafluoro-but-2-yl | Cl | Cl | C—H | C—F | 2.13 | 541 | |
| B10 | heptafluoro-prop-2-yl | Cl | Cl | C—CN | CH | 2.02 | 498 | |
| B11 | nonafluoro-but-2-yl | Et | Br | CH | CH | 2.06 | 563 | |
| B12 | nonafluoro-but-2-yl | Me | Br | CH | CH | 2.00 | 549 | |
| B13 | trifluoromethyl | Cl | Cl | CH | CH | 1.77 | 414 | |

TABLE C

Compound of formula (Ie): $R^2 = H$ and $A^1 = CH$ (Ie)

| Ex. | $Q^1$ | $Y^3$ | $Y^1$ | $Y^5$ | $A^4$ | RT (min) | MH+ | M − H+ |
|---|---|---|---|---|---|---|---|---|
| C1 | 2-fluoro-phenyl | nonafluoro-but-2-yl | Cl | Cl | C—F | 2.29 | 662.66 | |
| C2 | 2-methyl-phenyl | nonafluoro-but-2-yl | Cl | Cl | C—F | 2.21 | 659.13 | |
| C3 | 2-chloro-phenyl | nonafluoro-but-2-yl | Cl | Cl | C—F | 2.2 | 679.07 | |
| C4 | 4-cyano-phenyl | nonafluoro-but-2-yl | Cl | Cl | C—F | 2.1 | 670.01 | |
| C5 | 4-nitro-phenyl | nonafluoro-but-2-yl | Cl | Cl | C—F | 2.15 | 690.1 | |
| C6 | 4-methyl-phenyl | nonafluoro-but-2-yl | Cl | Cl | C—F | 2.23 | 659.12 | |
| C7 | 2-methyl-4-fluoro-phenyl | nonafluoro-but-2-yl | Cl | Cl | C—F | 2.22 | 677.09 | |
| C8 | 2-fluoro-5-chloro-Phenyl | nonafluoro-but-2-yl | Cl | Cl | C—F | 2.33 | 697.03 | |
| C9 | 4-nitro-2-chloro-Phenyl | nonfluoro-but-2-yl | Cl | Cl | C—F | 2.2 | 724.04 | |
| C10 | furanyl | nonafluoro-but-2-yl | Cl | Cl | C—F | 2.1 | 635.06 | |
| C11 | 4-trifluoro-methoxy-Phenyl | nonafluoro-but-2-yl | Cl | Cl | C—F | 2.3 | 729.08 | |
| C12 | 3-trifluoro-methyl-4-fluoro-Phenyl | nonafluoro-but-2-yl | Cl | Cl | C—F | 2.29 | 731.07 | |
| C13 | 3-trifluoro-methyl-Phenyl | nonafluoro-but-2-yl | Cl | Cl | C—F | 2.27 | 713.7 | |
| C14 | 2-trifluoro-methoxy-Phenyl | nonafluoro-but-2-yl | Cl | Cl | C—F | 2.28 | 729.08 | |
| C15 | 2-methoxy-Phenyl | nonafluoro-but-2-yl | Cl | Cl | C—F | 2.32 | 675.11 | |
| C16 | Phenyl | nonafluoro-but-2-yl | Cl | Cl | C—F | 2.16 | 645.1 | |
| C17 | 4-fluoro-Phenyl | nonafluoro-but-2-yl | Cl | Cl | C—F | 2.17 | 663.17 | |
| C18 | 2-trifluoro-methyl-Phenyl | nonafluoro-but-2-yl | Cl | Cl | C—F | 2.2 | 713.07 | |
| C19 | 4-fluoro-2-chloro-Phenyl | nonafluoro-but-2-yl | Cl | Cl | C—F | 2.23 | 697.05 | |
| C20 | 4-Methyl-[1,2,3]thiadiazole | nonafluoro-but-2-yl | Cl | Cl | C—F | 2.11 | 667.06 | |
| C21 | 2,3-difluoro-Phenyl | nonafluoro-but-2-yl | Cl | Cl | C—F | 2.24 | 681.08 | |
| C22 | 2,4-difluoro-Phenyl | nonafluoro-but-2-yl | Cl | Cl | C—F | 2.26 | 681.07 | |
| C23 | 2-fluoro-5-trifluoro-methyl-Phenyl | nonafluoro-but-2-yl | Cl | Cl | C—F | 2.33 | 731.08 | |

Biological Examples

This illustrates the pesticidal/insecticidal properties of compounds of formula (I). Tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behaviour, and growth regulation 3 days after treatment (DAT).

The following compounds gave at least 80% control of *Spodoptera littoralis*:
A1, A2, A3, A4, A5, A6, A7, A8, A9, A10, A11, A12, A13, A15, A16, A17, A20, A21, A22, A23, A28, A29, A31, A35, A36, A38, A40, A41, A43, A44, A45, A47, A48, A51, A54, A55, A56, A57, A58, A60, A61, A62, A63, A68, A69, A72, A75, A76, A78, A79, A80, A81, A83, A84, A85, A87, A89, A90, A96, A99, A100, A102, A103, A104, A105, A106, A107, A108, A110, A111, A117, A118, A119, A120, A121, A122, A123, A126, A129, A132, A138, A142, A145, A146, A147, A148, A149, A150, A152, A153, A154, A156, A159, A160, A162, A163, A164, A165, A168, A169, A170, A171, A172, A173, A176, A179, A182, A183, A184, A185, A186, A187, A188, A191, A192, A193, A194, A195, A196, A198, A199, A200, A202, A205, A206, A208, A209, A210, A211, A213, A214, A216, A217, A218, A219, A220, A221, A222, A223, C2, C3, C4, C5, C6, C7, C9, C10, C11, C13, C14, C15, C16, C17, C19, C20, C21

*Heliothis virescens* (Tobacco Budworm):
Eggs (0 to 24 h old) were placed in 24-well microtiter plate on artificial diet and treated with test solutions at an application rate of 200 ppm (concentration in well 18 pm) by pipetting. After an incubation period of 4 days, samples were checked for egg mortality, larval mortality, and growth regulation.

The following compounds gave at least 80% control of *Heliothis virescens*:
A1, A2, A3, A4, A5, A6, A7, A8, A9, A10, A11, A12, A13, A15, A16, A17, A20, A23, A24, A29, A35, A36, A37, A38, A39, A40, A41, A43, A44, A45, A46, A47, A48, A49, A51, A54, A55, A56, A57, A58, A60, A61, A62, A63, A64, A65, A66, A67, A68, A69, A72, A75, A76, A77, A78, A79, A80, A81, A83, A84, A85, A86, A87, A88, A89, A90, A91, A93, A96, A97, A98, A99, A100, A102, A103, A104, A105, A106, A107, A108, A109, A110, A111, A112, A114, A117, A118, A119, A120, A121, A122, A123, A125, A126, A127, A128, A129, A131, A132, A133, A138, A139, A140, A141, A142, A144, A145, A146, A147, A148, A149, A150, A153, A154, A155, A156, A159, A160, A162, A163, A164, A165, A167, A168, A169, A170, A171, A172, A173, A175, A176, A177, A182, A183, A184, A185, A186, A187, A190, A191, A192, A193, A194, A195, A196, A198, A199, A200, A201, A202, A205, A206, A207, A208, A209, A210, A211, A213, A214, A215, A216, A217, A218, A219, A220, A221, A222, A223, A225, B6, C2, C3, C4, C5, C6, C7, C9, C10, C12, C13, C16, C17, C18, C19, C20, C21.

*Plutella xylostella* (Diamond Back Moth):
24-well microtiter plate (MTP) with artificial diet was treated with test solutions at an application rate of 200 ppm (concentration in well 18 ppm) by pipetting. After drying, the MTP's were infested with L2 larvae (7 to 12 per well). After an incubation period of 6 days, samples were checked for larval mortality, and growth regulation.

The following compounds gave at least 80% control of *Plutella xylostella*:
A1, A2, A3, A4, A5, A6, A7, A8, A9, A10, A11, A12, A13, A15, A16, A17, A20, A22, A23, A28, A29, A35, A36, A38, A39, A43, A44, A45, A47, A48, A54, A56, A57, A58, A60, A61, A62, A63, A66, A68, A69, A75, A76, A78, A79, A80, A81, A83, A84, A85, A87, A89, A90, A96, A97, A98, A99, A100, A102, A103, A104, A105, A106, A108, A110, A111, A117, A118, A120, A121, A122, A123, A126, A129, A132, A138, A140, A145, A146, A147, A148, A149, A150, A152, A153, A154, A156, A159, A160, A162, A163, A164, A165, A170, A171, A172, A173, A175, A176, A182, A183, A184, A185, A186, A191, A192, A193, A194, A195, A196, A198, A199, A200, A201, A202, A205, A206, A207, A208, A209, A210, A211, A213, A214, A216, A217, A218, A219, A220, A222, A223, B6, C2, C3, C4, C5, C6, C7, C9, C10, C11, C12, C13, C16, C17, C18, C19, C20, C21.

*Diabrotica balteata* (Corn Root Worm):
A 24-well microtiter plate (MTP) with artificial diet was treated with test solutions at an application rate of 200 ppm (concentration in well 18 ppm) by pipetting. After drying, the MTP's were infested with L2 larvae (6 to 10 per well). After an incubation period of 5 days, samples were checked for larval mortality and growth regulation.

The following compound gave at least 80% control of *Diabrotica balteata*:
A1, A8, A10, A11, A13, A14, A23, A43, A44, A45, A58, A63, A65, A76, A84, A89, A90, A96, A99, A100, A102, A104, A105, A106, A107, A111, A117, A118, A120, A126, A147, A148, A149, A150, A159, A160, A161, A162, A163, A170, A171, A183, A193, A194, A195, A196, A198, A205, A206, A208, A209, A211, A214, A220, C4, C5, C11, C12, C13, C17

*Tetranychus urticae* (Two-Spotted Spider Mite):
Bean leaf discs on agar in 24-well microtiter plates were sprayed with test solutions at an application rate of 200 ppm. After drying, the leaf discs were infested with mite populations of mixed ages. 8 Days later, discs were checked for egg mortality, larval mortality, and adult mortality.

The following compounds gave at least 80% control of *Tetranychus urticae*:
A3, A4, A5, A22, A40, A41, A45, A46, A54, A58, A65, A75, A84, A86, A90, A96, A97, A99, A100, A102, A104, A105, A107, A109, A117, A118, A121, A123, A146, A147, A148, A149, A150, A152, A153, A156, A159, A160, A162, A163, A173, A182, A186, A191, A192, A193, A194, A195, A196, A198, A199, A202, A205, A206, A208, A209, A219, A220, A223

*Thrips tabaci* (Onion Thrips):
Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of *Thrips tabaci*:
A1, A3, A4, A5, A41, A44, A54, A62, A63, A76, A80, A81, A96, A100, A102, A117, A118, A123, A138, A145, A146, A147, A148, A149, A150, A152, A153, A154, A156, A159, A160, A162, A163, A164, A170, A171, A172, A173, A175, A182, A183, A191, A192, A193, A194, A195, A196, A198, A199, A202, A205, A206, A208, A209, A210, A211, A214, A220, C3, C13, C16

*Myzus persicae* (Green Peach Aphid):
Sunflower leaf discs are placed on agar in a 24-well microtiter plate and sprayed with test solutions at an application rate of 200 ppm. After drying, the leaf discs are infested with an aphid population of mixed ages. After an incubation period of 6 DAT, samples are checked for mortality.

The following compounds gave at least 80% control of *Myzus persicae*: A160, A129

The invention claimed is:
1. A compound of formula (I)

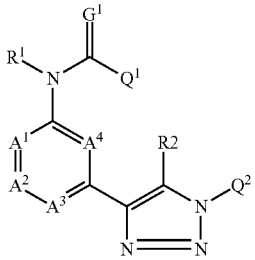

wherein
$A^1$, $A^2$, $A^3$ and $A^4$ are each independently C—X, wherein each X may be the same or different;
$R^1$ is hydrogen, $C_1$-$C_4$alkyl, $C_1$-$C_4$alkyl-C(O)NH$_2$, or $C_1$-$C_4$alkylcarbonyl;
$R^2$ is hydrogen, halogen, $C_1$-$C_4$alkyl, $C_1$-$C_4$alkyl-C(O)NH$_2$, $C_1$-$C_6$ haloalkyl or cyano;
$G^1$ is oxygen or sulfur;
X is hydrogen, halogen, or cyano;
$Q^1$ is phenyl, pyridyl, furanyl, thiophenyl, pyrazolyl or 1,2,3-thiadiazolyl; each optionally substituted by one to four substituents independently selected from cyano, nitro, hydroxy, bromo, chloro, fluoro, methyl, ethyl trifluoromethyl, methoxy, trifluoromethoxy, methylthio, methylsulfinyl, methylsulfonyl and phenyl;
$Q^2$ is a moiety of formula (A)

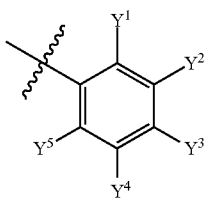

$Y^1$ and $Y^5$ are each independently selected from hydrogen, cyano, halogen, $C_1$-$C_4$alkyl, $C_1$-$C_4$haloalkyl, $C_1$-$C_4$alkoxy-$C_1$-$C_4$alkyl, $C_1$-$C_3$alkylthio, $C_1$-$C_3$haloalkylthio, $C_1$-$C_3$alkylsulfinyl, $C_1$-$C_3$haloalkylsulfinyl, $C_1$-$C_3$alkylsulfonyl and $C_1$-$C_3$haloalkylsulfonyl;
$Y^3$ is $C_1$-$C_6$perfluoroalkyl, $C_1$-$C_6$perfluoroalkylthio, $C_1$-$C_6$perfluoroalkylsulfinyl or $C_1$-$C_6$perfluoroalkylsulfonyl;
$Y^2$ and $Y^4$ are each independently selected from hydrogen, halogen and $C_1$-$C_4$alkyl;
or an agrochemically acceptable salt or N-oxides thereof.

2. A compound according to claim 1 wherein $A^1$ is CH, C—CN or C—F; and $A^2$, $A^3$ and $A^4$ are CH.

3. A compound according to claim 1 wherein $R^1$ is hydrogen, methyl or ethyl.

4. A compound according to claim 1 wherein $R^2$ is hydrogen, trifluoromethyl or halogen.

5. A compound according to claim 1 wherein $G^1$ is oxygen.

6. A compound according claim 1 wherein $Q^1$ is phenyl or pyridyl; each optionally substituted by one, two or three substituents independently selected from cyano, nitro, chloro, fluoro, methyl, ethyl, trifluoromethyl, methoxy and trifluoromethoxy.

7. A compound according to claim 1 wherein $Q^2$ is a moiety of formula (A);
$Y^1$ and $Y^5$ are each independently selected from hydrogen, cyano, fluoro, chloro, bromo, methyl, ethyl, trifluoromethyl and methoxymethyl; and
$Y^2$ and $Y^4$ are each independently selected from hydrogen, fluoro, chloro and methyl.

8. A compound according claim 7 wherein $Y^1$ and $Y^5$ are each chloro; and $Y^2$ and $Y^4$ are each hydrogen.

9. A compound according to claim 7 wherein $Y^3$ is heptafluoropropyl, nonafluorobutyl, heptafluoropropylthio, heptafluoropropylsulfinyl, or heptafluoropropylsulfonyl.

10. A compound according to claim 9 wherein $Y^3$ is heptafluoroprop-2-yl or nonafluorobut-2-yl.

11. An insecticidal, acaricidal, nematicidal or molluscicidal composition comprising an insecticidally, acaricidally, nematicidally or molluscicidally effective amount of a compound of formula (I) as defined in claim 1.

* * * * *